United States Patent
Mo et al.

(10) Patent No.: US 10,729,666 B2
(45) Date of Patent: *Aug. 4, 2020

(54) USE OF GABAA RECEPTOR REINFORCING AGENT IN PREPARATION OF SEDATIVE AND ANESTHETIC MEDICAMENT

(71) Applicant: Sichuan Haisco Pharmaceutical Co., Ltd., Chengdu (CN)

(72) Inventors: Yi Mo, Chengdu (CN); Fangqiong Li, Chengdu (CN); Jianyu Liu, Chengdu (CN); Yan Yu, Chengdu (CN); Honghu Li, Chengdu (CN); Hong Mu, Chengdu (CN); Yuquan Zhang, Chengdu (CN); Qingyang Yu, Chengdu (CN); Fujun Cheng, Chengdu (CN); Pangke Yan, Chengdu (CN); Ziwei Zhao, Chengdu (CN); Linlin Qin, Chengdu (CN)

(73) Assignee: HAISCO CHENGDU PHARMACEUTICAL TECHNOLOGY CO., LTD., Chengdu, Sichuan (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/508,677

(22) PCT Filed: Aug. 28, 2015

(86) PCT No.: PCT/CN2015/088341
§ 371 (c)(1),
(2) Date: Mar. 3, 2017

(87) PCT Pub. No.: WO2016/034079
PCT Pub. Date: Mar. 10, 2016

(65) Prior Publication Data
US 2017/0290781 A1   Oct. 12, 2017

(30) Foreign Application Priority Data

Sep. 4, 2014  (CN) .......................... 2014 1 0449571
Sep. 4, 2014  (CN) .......................... 2014 1 0449723

(51) Int. Cl.
*A61K 31/05*   (2006.01)
*A61P 25/20*   (2006.01)
(Continued)

(52) U.S. Cl.
CPC ................. *A61K 31/05* (2013.01); *A61J 1/18* (2013.01); *A61K 9/0019* (2013.01); *A61K 9/08* (2013.01);
(Continued)

(58) Field of Classification Search
CPC ...... A61K 31/05; A61K 45/06; A61K 9/0019; A61K 9/08; A61K 9/19; A61K 9/107;
(Continued)

(56) References Cited

U.S. PATENT DOCUMENTS 3,816,624 A * 6/1974 Davis et al. ......... A61K 31/573
514/179
9,517,988 B2 * 12/2016 Qin ..................... C07F 9/65744
(Continued)

FOREIGN PATENT DOCUMENTS

CA         911845 A1    11/2014
CA        2911845 A1    11/2014
(Continued)

OTHER PUBLICATIONS

Bundgaard. Design of Prodrugs: Bioreversible derivatives for various functional groups and chemical entities. pp. 1-94. (Year: 1985).*
(Continued)

*Primary Examiner* — Lakshmi S Channavajjala
(74) *Attorney, Agent, or Firm* — Ohlandt, Greeley, Ruggiero & Perle, LLP

(57) ABSTRACT

The present disclosure provides a pharmaceutical preparation of a compound of formula (I) or a stereoisomer, pharmaceutically acceptable salt, or prodrug thereof. The present disclosure further provides a method for general anesthesia or sedation for mammals. Also provided are kits and manufactured products of the medicament and the pharmaceutical composition and a method for using the medicament and the pharmaceutical composition.

(Continued)

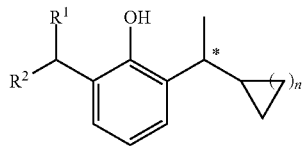

(I)

54 Claims, 1 Drawing Sheet

| | 2012/0029235 A1 | 2/2012 | Leuwer et al. |
| | 2016/0060197 A1 | 3/2016 | Qin et al. |
| | 2017/0290781 A1 | 10/2017 | Mo et al. |

FOREIGN PATENT DOCUMENTS

| CN | 101199480 A | 6/2008 |
| EP | 2995604 A1 | 3/2016 |
| EP | 3189834 A1 | 7/2017 |
| JP | 2002514656 A | 5/2002 |
| JP | 2010540068 A | 12/2010 |
| JP | 2012511558 A | 2/2012 |
| JP | 2016520054 A | 7/2016 |
| WO | 2009140275 A1 | 11/2009 |
| WO | 20090140275 A1 | 11/2009 |
| WO | 2014180305 A1 | 11/2014 |
| WO | 20140180305 A1 | 11/2014 |
| WO | 2016034079 A1 | 3/2016 |
| WO | 20160034079 A1 | 3/2016 |

OTHER PUBLICATIONS

Wolff. Burger's medicinal chemisrty and drug discovery. fifth edition. vol. 1: principles and practice. p. 975-977. (Year: 1995).*
Banker et al. Modern Pharmaceutics. 3rd edition. pp. 451 and 596 (Year: 1996).*
Office Action dated Oct. 25, 2017 for Eurasian patent application No. 201790525.
Chinese Office Action (with English translation) dated Sep. 1, 2017 for Chinese application No. 201580001777.2.
Office Action with Search Report dated Apr. 11, 2018 for Taiwan patent application No. 104129138.
Extended European Search Report dated May 8, 2018 for European patent application No. 15837862.0.
Linlin Qin et al: "Design, Synthesis, and Evaluation of Novel 2, 6-Disubstituted Phenol Derivatives as General Anesthetics", Journal of Medicinal Chemistry, vol. 60, No. 9, Apr. 28, 2017 (Apr. 28, 2017), pp. 3606-3617.
Chinese Office Action dated May 3, 2017 for Chinese application No. 201580001777.2.
Chinese Search Report dated May 3, 2017 for Chinese application No. 201580001777.2.
Picard et al; "Prevention of Pain on Injection with Propfol: A Quantitative Systematic Review"; International Anesthesia Research Society; Dec. 14, 1999; pp. 1-7.
Richards et al; "Epidural Anaesthesia as a Method of Pre-Emptive Analgesia for Abdonminal Hysterectomy"; Blackwell Science Ltd; Jul. 8, 1997; pp. 296-307.
Lingamaneni et al; "Anesthetic Properties of 4-Iodopropofor"; Anesthesiology vol. 94, No. 6; Jun. 2001; pp. 1-9.
International Search Report dated Nov. 24, 2015 for PCT application No. PCT/CN2015/088341.
Japanese Office Action dated Sep. 30, 2018 for Japanese application No. 2017-512737.
Office Action dated Jun. 29, 2018 for Eurasian patent application No. 201790525.
Office Action dated Jul. 27, 2018 for Australian patent application No. 2015311394.
Examination Report dated May 27, 2019 for counterpart Indian patent application No. 201727009711.
Second Office Action and search report dated Aug. 20, 2019 for counterpart Canadian patent application No. 2,959,812.
First Office Action and search report dated Jan. 28, 2019 for Canadian patent application No. 2,959,812.
Third Office Action (with English translation) dated Mar. 6, 2019 for Eurasian patent application No. 201790525.
First Office Action dated Apr. 25, 2019 for Korean patent application No. 10-2017-7009061,with the English translation.

* cited by examiner

(51) Int. Cl.
| A61K 9/08 | (2006.01) |
| A61K 9/107 | (2006.01) |
| A61K 9/19 | (2006.01) |
| A61P 1/08 | (2006.01) |
| A61P 25/08 | (2006.01) |
| A61K 45/06 | (2006.01) |
| A61P 25/24 | (2006.01) |
| A61P 25/22 | (2006.01) |
| A61P 25/18 | (2006.01) |
| A61P 25/06 | (2006.01) |
| C07F 9/09 | (2006.01) |
| A61K 31/661 | (2006.01) |
| A61J 1/18 | (2006.01) |
| A61K 9/00 | (2006.01) |
| A61K 47/02 | (2006.01) |
| A61K 47/10 | (2017.01) |
| A61K 47/12 | (2006.01) |
| A61K 47/14 | (2017.01) |
| A61K 47/18 | (2017.01) |
| A61K 47/24 | (2006.01) |
| A61K 47/26 | (2006.01) |
| A61K 47/44 | (2017.01) |

(52) U.S. Cl.
CPC .............. *A61K 9/107* (2013.01); *A61K 9/19* (2013.01); *A61K 31/661* (2013.01); *A61K 45/06* (2013.01); *A61K 47/02* (2013.01); *A61K 47/10* (2013.01); *A61K 47/12* (2013.01); *A61K 47/14* (2013.01); *A61K 47/18* (2013.01); *A61K 47/183* (2013.01); *A61K 47/24* (2013.01); *A61K 47/26* (2013.01); *A61K 47/44* (2013.01); *A61P 1/08* (2018.01); *A61P 25/06* (2018.01); *A61P 25/08* (2018.01); *A61P 25/18* (2018.01); *A61P 25/20* (2018.01); *A61P 25/22* (2018.01); *A61P 25/24* (2018.01); *C07F 9/091* (2013.01)

(58) Field of Classification Search
CPC .......... A61P 25/00; A61P 25/06; A61P 25/08; A61P 25/20; A61P 25/22; A61P 25/28; A61P 25/24
See application file for complete search history.

(56) References Cited

U.S. PATENT DOCUMENTS

| 2005/0059654 A1* | 3/2005 | Americ .............. A61K 31/135 |
| | | 514/220 |
| 2010/0228155 A1 | 9/2010 | Yang | |

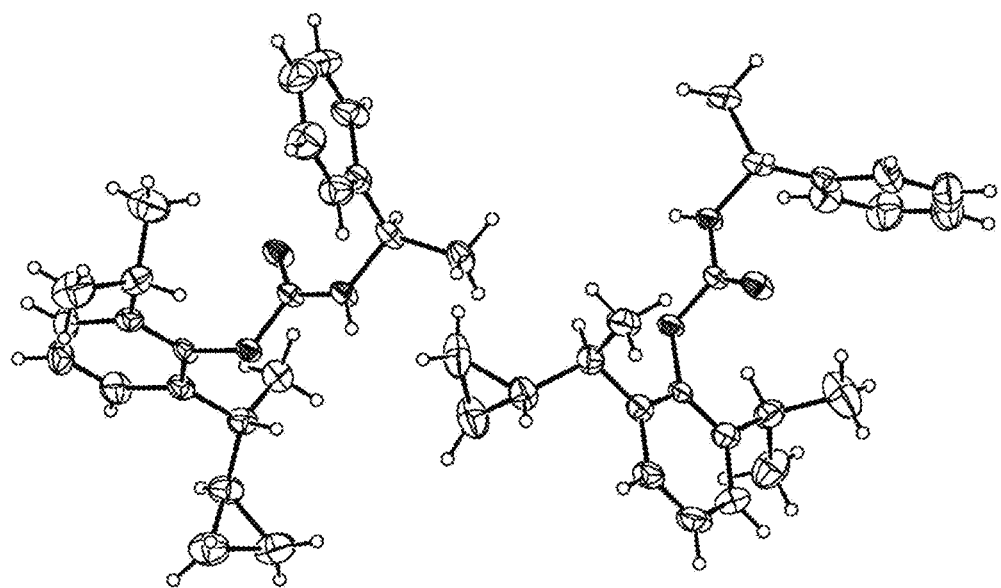

USE OF GABAA RECEPTOR REINFORCING AGENT IN PREPARATION OF SEDATIVE AND ANESTHETIC MEDICAMENT

CROSS-REFERENCE TO RELATED APPLICATIONS

The present application is a national stage application of PCT Patent Application No. PCT/CN2015/088341, filed Aug. 28, 2015, which claims priority to Chinese Patent Application No. 2014104495713, filed Sep. 4, 2014, and to Chinese Patent Application No. 201410449723X, filed Sep. 4, 2014, the contents of each of which are hereby incorporated by reference in their entireties.

BACKGROUND OF THE DISCLOSURE

1. Field of the Disclosure

The present invention relates to a phenol derivative-containing pharmaceutical formulation, a pharmaceutical composition, and their use in the field related to the central nervous system, in particular for use in sedation and anesthetization. The present invention also relates to a method for sedation and anesthetization by using a phenol derivative.

2. Description of Related Art

The $GABA_A$ receptor (γ-aminobutyric acid type A receptor) is a receptor of the chief inhibitory neurotransmitter in the central nervous system. The $GABA_A$ receptor is involved in pathogenesis, diagnosis, and treatment of various conditions such as anesthesia, depression, anxiety, epilepsy, memory disorders, and drug dependence, and has accordingly become a pharmacologically and clinically important target for drugs. Propofol is a $GABA_A$-targeting compound, and is a relatively new, short-acting intravenous anesthetic rapidly taking effect, useful for anesthetic induction, anesthesia maintenance, or sedation of critically ill patients in ICU.

Propofol can enhance activation of many $GABA_A$ receptor subtypes, and is a clinically sophisticated intravenous anesthetic widely used for induction and maintenance of general anesthesia. Propofol is advantageous in that it rapidly induces anesthesia in a subject who then regains consciousness in a short time and fully recovers with a low incidence of post-operation nausea and vomiting. However, its application in various clinical scenarios has been restricted by its adverse side effects caused by a therapeutic dose or a similar dose, such as respiratory depression, propofol infusion syndrome, injection pain, and haemodynamic effects. With particular regards to haemodynamic effects, administration of propofol, especially in a bolus, often lowers the blood pressure, while the heart rate does not increase for compensation. Because of these adverse effects and possibly adverse haemodynamic effects of propofol, its application is incompatible to various clinical conditions, including cardiovascular diseases (e.g., coronary artery disease, cardiomyopathy, ischemic heart disease, valvular heart disease and congenital heart disease), chronic hypertension, brain injury, hemorrhagic shock, and the like.

Intravenous anesthetics currently used to induce and maintain general anesthesia or sedation in clinical settings include propofol, midazolam, ketamine, thiopental sodium, sodium oxybate, and etomidate. However, there is still a demand for new intravenous anesthetics and the methods for administering such intravenous anesthetics for induction and maintenance of anesthesia or sedation.

Propofol has obvious limitations and disadvantages. It has been reported that approximately 70% of patients on propofol injections feel certain pain or discomfort (Pascale Picard (2000) *Anesthesia & Analgesia*, 90, 963-969). Although it has also been reported that pre-treatment with other drugs or combined administration of drugs may reduce the incidence and severity of pain caused by propofol injections (C. H. Tan, et al., (1998) *Anaesthesia*, 53, 302-305), such pain is still unavoidable. Propofol is generally administered in a dosage of 2.0 to 2.5 mg/kg, often in combination with an anodyne. Propofol injections for anesthesia induction may be mixed with a 0.5% or 1% lidocaine injection in a ratio greater than 20:1 for pain relief during injection. Propofol has proven to lower the systolic pressure, the diastolic pressure, and the mean arterial pressure, and thus may clinically cause hypotension. Furthermore, respiratory depression is also an unneglectable risk upon use of propofol. These adverse effects have considerably impeded application of propofol in certain clinical cases, such as cardiovascular diseases, a brain injury, and chronic hypotension.

Embodiments of the present invention relate to a propofol analog, which is a highly liposoluble substance, may be administered directly into the blood stream, and rapidly induces anesthesia.

An objective of the present invention is to provide a stable, efficacious, dose-efficient, safe, cost-effective pharmaceutical formulation containing a phenol derivative, which reduces pain during injection, allows good patient compliance, and does not need other drug agents to be used in combination; and to provide use of the pharmaceutical formulation in the manufacture of a medicament for inducing and maintaining anesthesia in an animal or human, for promoting sedative hypnosis of an animal or human, or for treating and/or preventing anxiety, depression, insomnia, nausea, vomiting, migraine, schizophrenia, convulsion, and epilepsy.

Embodiments of the present invention also provide a method for sedation and anesthetization, a pharmaceutical composition, and its use for sedation and anesthetization.

Compound (I) has higher $GABA_A$-enhancing activity than propofol, shows a greater therapeutic index, higher safety, and a broader therapeutic window in animal experiments, has a low free concentration in the aqueous phase of a corresponding formulation, and is expected to have an effect of avoiding pain during injection, being promising in clinical applications.

SUMMARY OF THE DISCLOSURE

The present invention relates to a pharmaceutical formulation comprising, as the active ingredient, a compound of general formula (I), or a stereoisomer, a pharmaceutically acceptable salt, or a prodrug thereof,

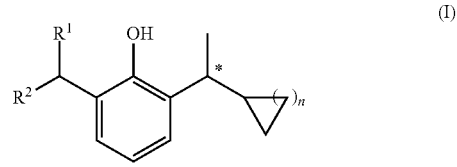

(I)

wherein $R^1$ and $R^2$ are each independently selected from a $C_{1-4}$ alkyl or a $C_{3-6}$ cycloalkyl; and n is 1 or 2.

In a preferred embodiment of the pharmaceutical formulation according to the present invention, the active ingredient is a compound of general formula (I), or a stereoisomer, a pharmaceutically acceptable salt, or a prodrug thereof, wherein $R^1$ is selected from methyl, ethyl or isopropyl; $R^2$ is selected from methyl, ethyl, isopropyl or cyclopropyl; n is 1 or 2.

In a preferred embodiment of the present invention, the compound of general formula (I) is selected from

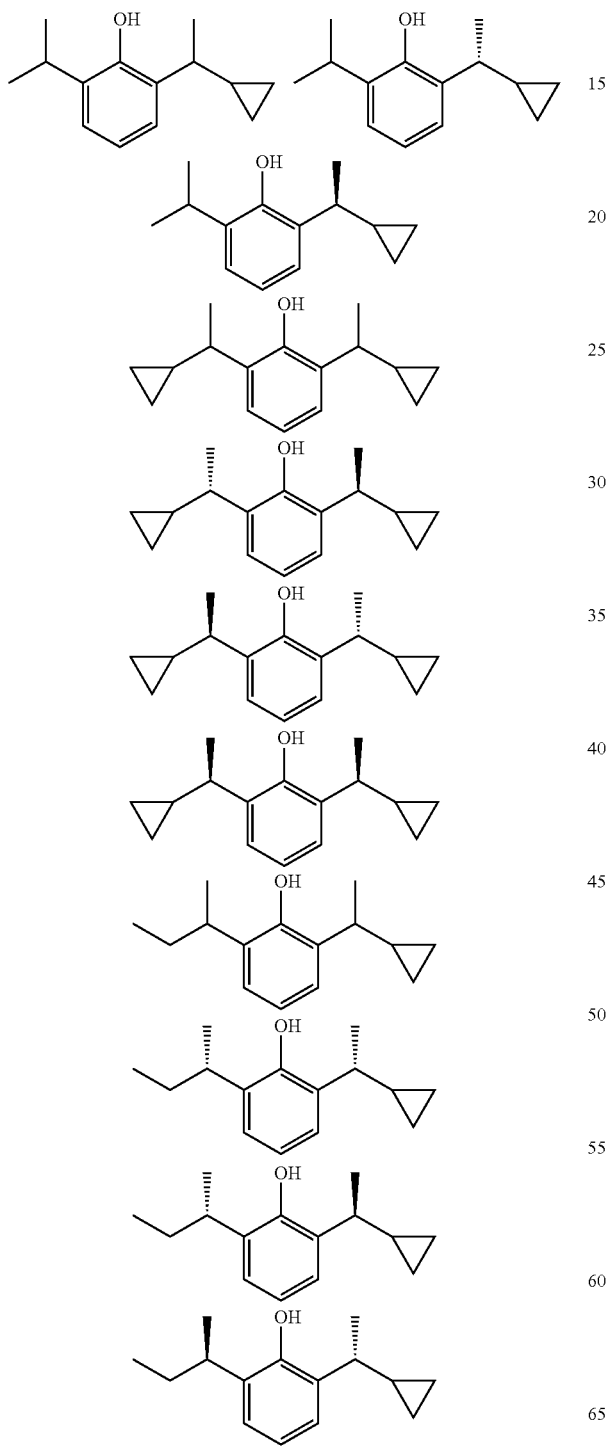

-continued

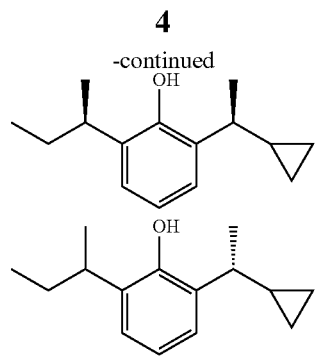

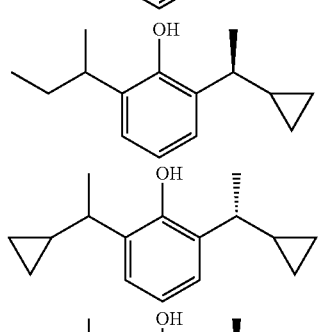

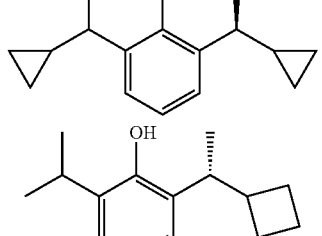

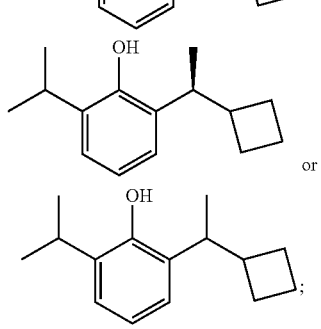

or preferably

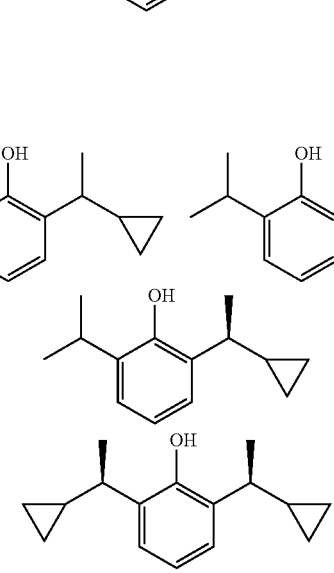

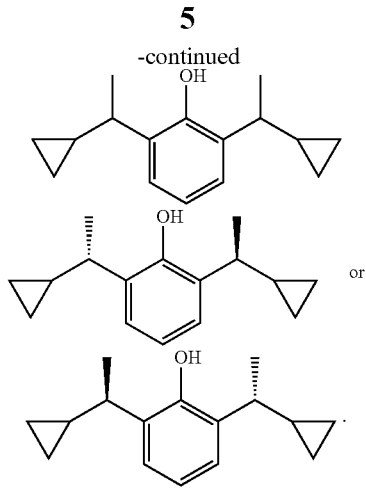

Embodiments of the present invention provides a pharmaceutical formulation, comprising 0.01 w/v % to 5 w/v % active ingredient which is a compound of general formula (I), or a stereoisomer, a pharmaceutically acceptable salt, or a prodrug thereof.

In a preferred embodiment of the pharmaceutical formulation according to the present invention, the pharmaceutical formulation is an aqueous solution, comprising:

1) a compound of general formula (I), or a stereoisomer, a pharmaceutically acceptable salt, or a prodrug thereof, in an amount of 0.01 w/v % to 5 w/v %, preferably 0.05 w/v % to 3 w/v %, more preferably 0.1 w/v % to 2 w/v %;

2) a solubilizing agent, in an amount of 0.1 w/v % to 20 w/v %, preferably 0.1 w/v % to 15 w/v %, more preferably 0.2 w/v % to 10 w/v %; and 3) a co-solvent, in an amount of 0 w/v % to 30 w/v %, preferably 0.1 w/v % to 20 w/v %, more preferably 0.1 w/v % to 10 w/v %.

In a preferred embodiment of the pharmaceutical formulation according to the present invention, the solubilizing agent is one of, or a mixture of more (in any ratio) of, Tween-80, Tween-20, PEG-35 castor oil, PEG-40 hydrogenated castor oil, PEG-15 hydroxystearate (i.e. solutol HS15) or poloxamer; preferably Tween-80, Tween-20 or PEG-15 hydroxystearate (i.e. solutol HS15); the co-solvent is one of, or a mixture of more (in any ratio) of, ethanol, glycerol, propylene glycol or PEG.

In a preferred embodiment of the pharmaceutical formulation according to the present invention, the pharmaceutical formulation is a lyophilized formulation, comprising:

1) a compound of general formula (I), or a stereoisomer, a pharmaceutically acceptable salt, or a prodrug thereof;
2) a solubilizing agent;
3) a co-solvent; and
4) a filler.

In a preferred embodiment of the pharmaceutical formulation according to the present invention, the pharmaceutical formulation is a lyophilized formulation obtained by lyophilizing a solution comprising:

1) a compound of general formula (I), or a stereoisomer, a pharmaceutically acceptable salt, or a prodrug thereof, in an amount of 0.01 w/v % to 5 w/v %, preferably 0.05 w/v % to 3 w/v %, more preferably 0.1 w/v % to 2 w/v %;

2) a solubilizing agent, in an amount of 0.1 w/v % to 20 w/v %, preferably 0.1 w/v % to 15 w/v %, more preferably 0.2 w/v % to 10 w/v %;

3) a co-solvent, in an amount of 0 w/v % to 30 w/v %, preferably 0.1 w/v % to 20 w/v %, more preferably 0.1 w/v % to 10 w/v %; and 4) a filler, in an amount of 1 w/v % to 30 w/v %, preferably 3 w/v % to 15 w/v %, more preferably 5 w/v % to 10 w/v %.

In a preferred embodiment of the pharmaceutical formulation according to the present invention, the pharmaceutical formulation comprises:

1) a compound of general formula (I), or a stereoisomer, a pharmaceutically acceptable salt, or a prodrug thereof, in an amount of 0.01 w/v % to 5 w/v %, preferably 0.05 w/v % to 3 w/v %, more preferably 0.1 w/v % to 2 w/v %;

2) a solubilizing agent, in an amount of 0.1 w/v % to 20 w/v %, preferably 0.1 w/v % to 15 w/v %, more preferably 0.2 w/v % to 10 w/v %;

3) a co-solvent, in an amount of 0 w/v % to 30 w/v %, preferably 0.1 w/v % to 20 w/v %, more preferably 0.1 w/v % to 10 w/v %; and 4) a filler, in an amount of 1 w/v % to 30 w/v %, preferably 3 w/v % to 15 w/v %, more preferably 5 w/v % to 10 w/v %.

In a preferred embodiment of the pharmaceutical formulation according to the present invention, the solution for the pharmaceutical formulation is lyophilized after being prepared.

In a preferred embodiment of the pharmaceutical formulation according to the present invention, the solubilizing agent is one of, or a mixture of more (in any ratio) of, Tween-80, Tween-20, PEG-35 castor oil, PEG-40 hydrogenated castor oil, PEG-15 hydroxystearate or poloxamer; the co-solvent is one of, or a mixture of more (in any ratio) of, ethanol, glycerol, propylene glycol or PEG; and the filler is one of, or a mixture of more (in any ratio) of, lactose, sucrose, glucose, mannitol, sodium dihydrophosphate, sodium phosphate, sodium chloride, disodium hydrogen phosphate, cysteine, glycine, sorbitol, calcium lactobionate, dextran or polyvinylpyrrolidone.

In a preferred embodiment of the pharmaceutical formulation according to the present invention, the lyophilized formulation or the aqueous solution formulation further contains at least a pH-adjusting agent in an amount of 0 w/v % to 10 w/v %, preferably 0 w/v % to 5 w/v %.

In a preferred embodiment of the pharmaceutical formulation according to the present invention, the pH-adjusting agent is one or any of sodium hydroxide, potassium hydroxide, triethanolamine, hydrochloric acid, phosphoric acid, citric acid, acetic acid, and malic acid; preferably one of, or a mixture of more (in any ratio) of, sodium hydroxide, potassium hydroxide, triethanolamine, phosphoric acid, citric acid, or hydrochloric acid; more preferably one of, or a mixture of more (in any ratio) of, sodium hydroxide or hydrochloric acid.

In a preferred embodiment of the pharmaceutical formulation according to the present invention, the lyophilized formulation or the aqueous solution formulation further contains at least an iso-osmotic adjusting agent in an amount of 0 w/v % to 5 w/v %, preferably 0 w/v % to 2 w/v %.

In a preferred embodiment of the pharmaceutical formulation according to the present invention, the iso-osmotic adjusting agent is one of, or a mixture of more (in any ratio) of, glycerol, saccharides, or sugar alcohols; preferably one of, or a mixture of more (in any ratio) of, glycerol, glucose, fructose, maltose, polyethylene glycol, sorbitol, propylene glycol, xylitol or mannitol; more preferably one of, or a mixture of more (in any ratio) of, glycerol, sorbitol, propylene glycol, polyethylene glycol or mannitol; even more preferably one of, or a mixture of more (in any ratio) of, glycerol, polyethylene glycol or mannitol; and further preferably glycerol.

In a preferred embodiment of the pharmaceutical formulation according to the present invention, the pharmaceutical formulation is a fat emulsion, comprising
1) a compound of general formula (I), or a stereoisomer, a pharmaceutically acceptable salt, or a prodrug thereof, and
2) an oily component.

In a preferred embodiment of the pharmaceutical formulation according to the present invention, the oily component is one of, or a mixture of more (in any ratio) of, natural and/or synthetic biocompatible fats that can be metabolized in human bodies; preferably one of, or a mixture of more (in any ratio) of, soybean oil, linseed oil, medium chain triglycerides, structural triglycerides, olive oil, corn oil, cottonseed oil, rapeseed oil, peanut oil, safflower oil, coconut oil, castor oil, fish oil, sesame oil or tea-seed oil; more preferably one of, or a mixture of more (in any ratio) of, soybean oil, olive oil, fish oil, structural triglycerides, linseed oil, or medium chain triglycerides; even more one of, or a mixture of both (in any ratio) of, soybean oil and medium chain triglycerides.

In a preferred embodiment of the pharmaceutical formulation according to the present invention, the fat emulsion further contains at least an emulsifying agent.

In a preferred embodiment of the pharmaceutical formulation according to the present invention, the emulsifying agent is one of, or a mixture of more (in any ratio) of, glycerol monooleate, Tween-80, Tween-20, poloxamer, PEG-35 castor oil, PEG-40 hydrogenated castor oil, polyethylene glycol glycerol, PEG-15 hydroxyl stearate, egg-yolk lecithin, egg yolk phosphatidylcholine, soybean lecithin, soybean phosphatidylcholine, hydrogenated egg-yolk lecithin, hydrogenated egg yolk phosphatidylcholine, hydrogenated soybean lecithin, hydrogenated soybean phosphatidylcholine, dipalmitoyl phosphatidylcholine, dimyristoyl phosphatidylcholine, distearoyl phosphatidylcholine, dioleoyl phosphatidylcholine, dipalmitoyl phosphatidylglycerol, dimyristoyl phosphatidylglycerol, distearoyl phosphatidylglycerol, dipalmitoyl phosphatidylethanolamine, dimyristoyl phosphatidylethanolamine, distearoyl phosphatidylethanolamine, or dioleoyl phosphatidylethanolamine; preferably one of, or a mixture of more (in any ratio) of, poloxamer, Tween-80, PEG-15 hydroxyl stearate, PEG-35 castor oil, PEG-40 hydrogenated castor oil, egg-yolk lecithin, or soybean lecithin; more preferably one of, or a mixture of both (in any ratio) of, egg-yolk lecithin and soybean lecithin.

In a preferred embodiment of the pharmaceutical formulation according to the present invention, the fat emulsion comprises:
1) a compound of general formula (I), or a stereoisomer, a pharmaceutically acceptable salt, or a prodrug thereof, in an amount of 0.01 w/v % to 5 w/v %, preferably 0.05 w/v % to 3 w/v %, more preferably 0.1 w/v % to 2 w/v %;
2) an oily component, in an amount of 5 w/v % to 30 w/v %, preferably 5 w/v % to 20 w/v %, more preferably 5 w/v % to 15 w/v %; and
3) an emulsifying agent, in an amount of 0.5 w/v % to 5 w/v %, preferably 0.5 w/v % to 3 w/v %, more preferably 0.5 w/v % to 2 w/v %.

In a preferred embodiment of the pharmaceutical formulation according to the present invention, the fat emulsion further contains at least a co-emulsifying agent in an amount of 0 to 0.2 w/v %.

In a preferred embodiment of the pharmaceutical formulation according to the present invention, the co-emulsifying agent is one of, or a mixture of more (in any ratio) of, sodium oleate, sodium cholate, sodium deoxycholate, oleic acid, cholic acid, deoxycholic acid or cholesterol; preferably one of, or a mixture of both (in any ratio) of, oleic acid or sodium oleate.

In a preferred embodiment of the pharmaceutical formulation according to the present invention, the fat emulsion further contains at least an iso-osmotic adjusting agent in an amount of 0 w/v % to 5 w/v %.

In a preferred embodiment of the pharmaceutical formulation according to the present invention, the iso-osmotic adjusting agent is one of, or a mixture of more (in any ratio) of, glycerol, saccharides, or sugar alcohols; preferably one of, or a mixture of more (in any ratio) of, glycerol, glucose, fructose, maltose, polyethylene glycol, sorbitol, propylene glycol, xylitol or mannitol; more preferably one of, or a mixture of more (in any ratio) of, glycerol, sorbitol, propylene glycol, polyethylene glycol or mannitol; even more preferably one of, or a mixture of more (in any ratio) of, glycerol, polyethylene glycol or mannitol; and further preferably glycerol.

In a preferred embodiment of the pharmaceutical formulation according to the present invention, the fat emulsion further contains at least a pH-adjusting agent in an amount of 0 w/v % to 10 w/v %, and the pH-adjusting agent is one or any of sodium hydroxide, potassium hydroxide, triethanolamine, hydrochloric acid, phosphoric acid, phosphate, citric acid, citrate, acetic acid, acetate, and malic acid; preferably one of, or a mixture of more (in any ratio) of, sodium hydroxide, potassium hydroxide, triethanolamine, or hydrochloric acid; more preferably one of, or a mixture of both (in any ratio) of, sodium hydroxide and hydrochloric acid.

In a preferred embodiment of the pharmaceutical formulation according to the present invention, the fat emulsion comprises:
1) a compound of general formula (I), or a stereoisomer, a pharmaceutically acceptable salt, or a prodrug thereof, in an amount of 0.1 w/v % to 2 w/v %;
2) one of, or a mixture in any ratio of two of, soybean oil and medium chain triglycerides, in an amount of 5 w/v % to 15 w/v %;
3) egg-yolk lecithin, in an amount of 0.5 w/v % to 2 w/v %;
4) glycerol in an amount of 0 w/v % to 5 w/v %; and
5) sodium oleate, in an amount of 0 w/v % to 0.2 w/v %.

In a preferred embodiment of the pharmaceutical formulation according to the present invention, the fat emulsion has a pH of 3.0 to 10.0, preferably 4.0 to 9.0, more preferably 6.0 to 9.0.

In a preferred embodiment of the pharmaceutical formulation according to the present invention, the pharmaceutical formulation may further contain other additives including, but not limited to, any one of or a mixture of more (in any ratio) of antioxidants and antibacterials.

The antibacterials include, but are not limited to, any one or more of methyl benzoate, sodium pyrosulfite, disodium edetate, and calcium sodium edetate.

The antioxidants include, but are not limited to, any one or more of sodium pyrosulfite, sodium sulfite, sodium bisulfite, potassium pyrosulfite, sodium thiosulfate, dibutylphenol, butylhydroxyanisole (BHA), t-butyl hydroquinone (TBHQ), dibutylhydroxytoluene (BHT), disodium edetate or calcium sodium edetate.

An embodiment of the present invention relates to use of the pharmaceutical formulation according to the present invention in the manufacture of a medicament for inducing and maintaining anesthesia in an animal or human, promoting sedative hypnosis of an animal or human, or treating and/or preventing anxiety, depression, insomnia, nausea, vomiting, migraine, schizophrenia, convulsion, and epilepsy, wherein the active ingredient is a compound of general formula (I), or a stereoisomer, a pharmaceutically acceptable salt, or a prodrug thereof.

Method for Preparing the Formulation According to the Present Invention

Method 1: Method for Preparing the Fat Emulsion

Preparation of oil phase: weighing out the oily component, adding an emulsifying agent and the compound of general formula (I) to the oily component under high-speed stirring and an inert gas atmosphere, thoroughly stirring the mixture to obtain an oil phase, controlling the temperature of the oil phase at 50° C. to 80° C.

Preparation of aqueous phase: under an inert gas atmosphere, adding an iso-osmotic adjusting agent and a stabilizing agent to an appropriate amount of water for injection, thoroughly stirring the mixture to obtain an aqueous phase, controlling the temperature of the aqueous phase at 50° C. to 80° C.

Preparation of emulsion: under an inert gas atmosphere and high-speed stirring, slowly adding the oil phase to the aqueous phase, followed by mixing to obtain an initial emulsion at a temperature which may be 50° C. to 80° C., homogenizing the initial emulsion in a high-pressure homogenizer until the emulsion particles are acceptable, followed by filtration, sealing in a container, sterilization, and cooling, to obtain an emulsion for injection of the compound of general formula (I).

The pharmaceutical formulation according to the present invention may have its pH generally adjusted to 6.0 to 9.0. In the preparation method described above, the manner, rotation speed, and duration of stirring are controlled according to requirements. In the preparation of the initial emulsion, a high-shear mixing emulsifier is preferred, but may be selected according to needs. In homogenization by a high-speed homogenizer, the condition and duration of the homogenization are well known to a person skilled in the art, and are selected as long as the average particle size of homogenized emulsion particles is not greater than 350 nm, 95% of the particles have a particle size not greater than 1.5 μm, and no particles have a particle size greater than 5 μm. The sterilization may be carried out by autoclaving, hot water bath, spraying, or the like, preferably by autoclaving (for example, at 121° C. for 12 min) as an example of sterilizing processes.

In the preparation method according to the present invention, the inert gas may be, but is not limited to, nitrogen.

The preparation method used according to the present invention comprises: uniformly dispersing the compound of general formula (I) in oil for injection and an emulsifying agent such that it is wrapped in an oil phase, and then adding an aqueous phase thereto. The prepared oil-in-water fat emulsion has good stability and less clinical side effects, and shows a stable quality after an accelerated and long-term stability test, suitable for large-scale production.

Method 2: Method for Preparing the Aqueous Solution

The method for mixing the components is not limited and may be carried out following general processes, as long as a clear liquid formulation can be obtained. For example, the compound according to the present invention, a solubilizing agent, and other oil-soluble additional components are weighed out and thoroughly mixed at a controlled temperature of 20° C. to 80° C., to obtain a mixed solution (1); an iso-osmotic adjusting agent and other water-soluble additional components are weighed out, and dissolved in a volume of water for rejection which is 50% to 80% of the total water volume required for the formulation, to obtain a mixed solution (2); a co-solvent may be added to (1) or (2) when necessary, and (1) and (2) are mixed under stirring until uniform, to obtain a clear liquid; an appropriate amount of injection needle-compatible activated carbon is added to the liquid, followed by stirring for 5 to 30 min to allow adsorption, then the carbon is removed by filtration, the pH is adjusted to 4 to 9, a volume of water for injection is added to make up the total water volume required for the formulation, followed by thorough stirring, filtration through a 0.22 μm filter, sealing in a container, and autoclaving, to obtain the formulation as an aqueous solution.

Method 3: Method for Preparing the Lyophilized Formulation

The method for formulation the solution to be lyophilized and the method for lyophilization are not limited and may be carried out following general processes, as long as an acceptable lyophilized formulation can be obtained. For example, the compound according to the present invention, a solubilizing agent, and other oil-soluble additional components are weighed out and thoroughly mixed at a controlled temperature of 20° C. to 80° C., to obtain a mixed solution (1); an iso-osmotic adjusting agent, a filler, and other water-soluble additional components are weighed out, and dissolved in a volume of water for rejection which is 50% to 80% of the total water volume required for the formulation, to obtain a mixed solution (2); a co-solvent may be added to (1) or (2) when necessary, and (1) and (2) are mixed under stirring until uniform, to obtain a clear liquid; an appropriate amount of injection needle-compatible activated carbon is added to the liquid, followed by stirring for 5 to 30 min to allow adsorption, then the carbon is removed by filtration, the pH is adjusted to 4 to 9, a volume of water for injection is added to make up the total water volume required for the formulation, followed by thorough stirring and filtration through a 0.22 μm filter; the resultant solution is fed into a penicillin bottle in a prescribed amount, and the bottle is loosely plugged, pre-frozen in a lyophilizer, and then lyophilized; the plug is tightened up in a vacuum or a suitable amount of inert gas, and the bottle is taken out of the lyophilizer and capped by pressing.

The method for preparing the lyophilized formulation according to the present invention is characterized in that it is easy to carry out, more suitable for long-term storage and convenient transportation of the product, and suitable for large-scale production.

An embodiment of the present invention relates to a method for general anesthetization or sedation in a mammal, comprising administering to the mammal an effective dose of a compound of general formula (I), or a stereoisomer, a pharmaceutically acceptable salt, or a prodrug thereof,

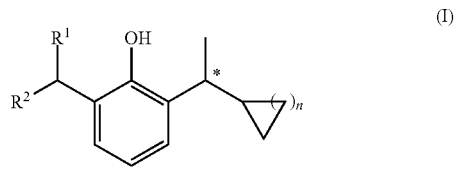

wherein $R^1$ and $R^2$ are each independently selected from a $C_{1-4}$ alkyl or a $C_{3-6}$ cycloalkyl; and n is 1 or 2.

In a preferred embodiment of the method for general anesthetization or sedation in a mammal according to the present invention, in the compound of general formula (I), $R^1$ is selected from methyl, ethyl or isopropyl; $R^2$ is selected from methyl, ethyl, isopropyl or cyclopropyl; n is 1 or 2.

In a preferred embodiment of the method for general anesthetization or sedation in a mammal according to the present invention, the compound of general formula (I) is selected from

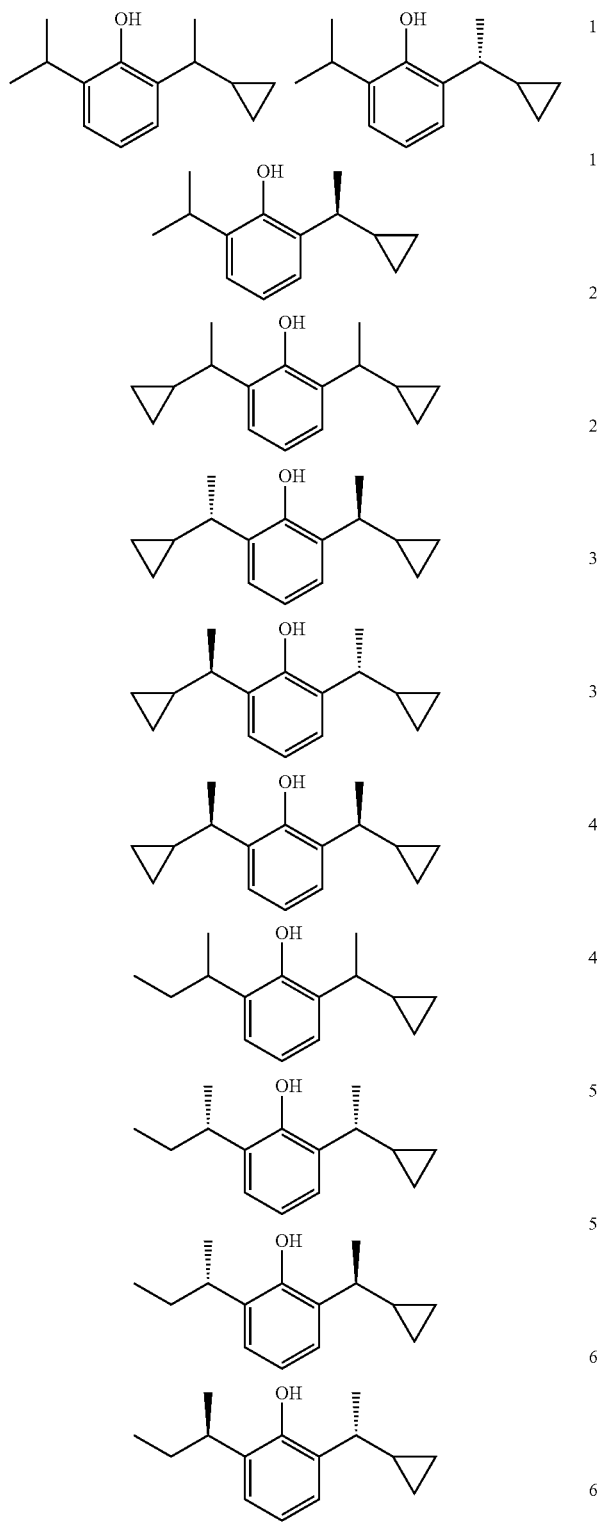

-continued

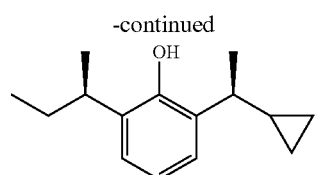

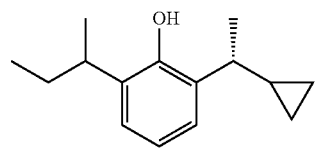

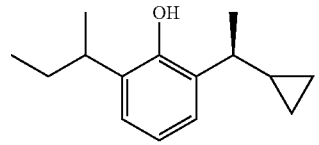

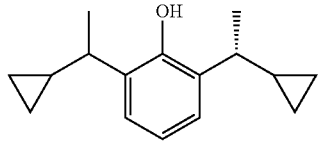

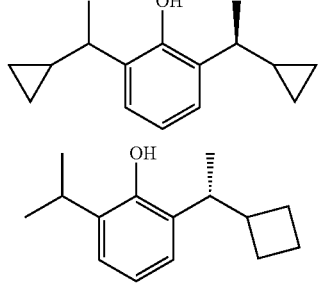

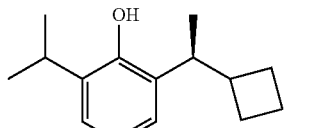

or

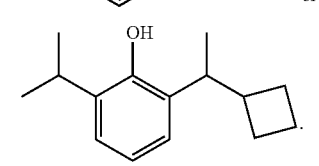

In a preferred embodiment of the method for general anesthetization or sedation in a mammal according to the present invention, the compound of general formula (I) is selected from -continued

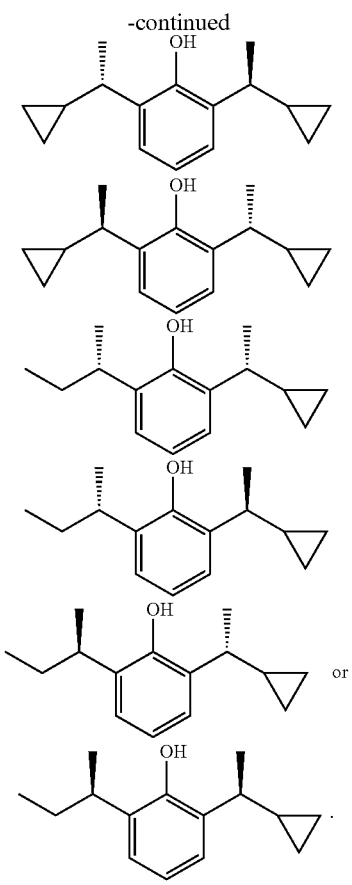

An embodiment of the present invention relates to a method for inducing or maintaining general anesthesia or sedation in a mammal, comprising administering to the mammal an effective dose of a compound of general formula (I), or a stereoisomer, a pharmaceutically acceptable salt, or a prodrug thereof, wherein the effective dose is a loading dose and/or a maintenance dose, the loading dose of the compound of general formula (I) is 0.01 mg/kg to 15.0 mg/kg, and the maintenance dose of the compound of general formula (I) is 0.01 mg/(kgh) to 20.0 mg/(kg·h); the loading dose of a prodrug of the compound of general formula (I) is 0.1 mg/kg to 30.0 mg/kg.

In a preferred embodiment of the method for general anesthetization or sedation in a mammal according to the present invention, the prodrug of the compound of general formula (I) is selected from compounds of general formula (II) below:

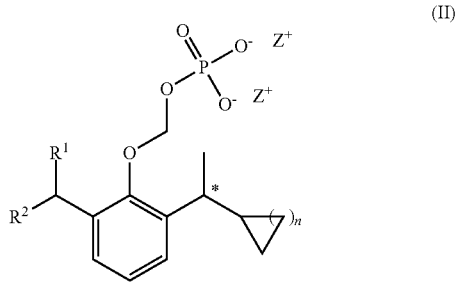

(II)

wherein $R^1$, $R^2$ and n have the same definitions as those in general formula (I);

$Z^+$ is each independently selected from $H^+$, an alkali metal ion or an ammonium ion;

wherein the alkali metal ion is selected from $Na^+$ or $K^+$, preferably $Na^+$.

In a preferred embodiment of the present invention, the effective dose includes a loading dose and/or a maintenance dose.

It is to be understood by a person skilled in the art that a loading dose and/or a maintenance dose for drug administration depends on many factors. For example, a dose for induction or maintenance of general anesthesia or sedation in a subject may be related to whether the subject is a human or a non-human mammal, and also related to the age, body weight, gender, diet, health status, or mental status of the subject. In practice, the loading dose and/or the maintenance dose is selected and adjusted by anesthetists, veterinarians, or other practitioners in medicine or health care according to the above factors and the response of subjects, in order to achieve a relatively stable blood drug level, stable depth and good controllability of anesthesia, good waking-up quality from anesthesia, and a stable body sign after anesthesia.

The dose may be selected from a series of doses, largely depending on the level and depth of general anesthesia or sedation to be achieved.

In a modified embodiment of the method for general anesthetization or sedation in a mammal according to the present invention, the loading dose of the compound of general formula (I) for general anesthetization or sedation is optionally selected from a range of 0.01 mg/kg to 15.0 mg/kg, a range of 0.05 mg/kg to 15.0 mg/kg, a range of 0.05 mg/kg to 10.0 mg/kg, a range of 0.1 mg/kg to 12.0 mg/kg, a range of 0.1 mg/kg to 10.0 mg/kg, a range of 0.1 mg/kg to 8.0 mg/kg, a range of 0.1 mg/kg to 6.0 mg/kg, a range of 0.1 mg/kg to 5.0 mg/kg, a range of 0.1 mg/kg to 4.0 mg/kg, a range of 0.1 mg/kg to 3.0 mg/kg, a range of 0.1 mg/kg to 2.0 mg/kg, a range of 0.1 mg/kg to 1.0 mg/kg, a range of 0.1 mg/kg to 0.8 mg/kg, a range of 0.1 mg/kg to 0.6 mg/kg, a range of 0.1 mg/kg to 0.5 mg/kg, a range of 0.1 mg/kg to 0.3 mg/kg, or a range of 0.1 mg/kg to 0.2 mg/kg.

In a modified embodiment of the method for general anesthetization or sedation in a mammal according to the present invention, the loading dose of a prodrug of the compound of general formula (I) for general anesthetization or sedation is optionally selected from a range of 0.1 mg/kg to 30.0 mg/kg, a range of 0.5 mg/kg to 15.0 mg/kg, a range of 1.0 mg/kg to 12.0 mg/kg, a range of 1.0 mg/kg to 10.0 mg/kg, a range of 1.0 mg/kg to 8.0 mg/kg, a range of 1.0 mg/kg to 7.0 mg/kg, a range of 1.0 mg/kg to 6.0 mg/kg, or a range of 1.0 mg/kg to 5.0 mg/kg.

In a modified embodiment of the method for general anesthetization or sedation in a mammal according to the present invention, the maintenance dose of the compound of general formula (I) for general anesthetization or sedation is optionally selected from a range of 0.01 mg/(kg·h) to 20.0 mg/(kg·h), a range of 0.01 mg/(kg·h) to 15.0 mg/(kg·h), a range of 0.01 mg/(kg·h) to 10.0 mg/(kg·h), a range of 0.02 mg/(kg·h) to 6.0 mg/(kg·h), a range of 0.05 mg/(kg·h) to 6.0 mg/(kg·h), a range of 0.05 mg/(kg·h) to 5.0 mg/(kg·h), a range of 0.05 mg/(kg·h) to 4.0 mg/(kg·h), a range of 0.1 mg/(kg·h) to 4.0 mg/(kg·h), a range of 0.1 mg/(kg·h) to 3.0 mg/(kg·h), a range of 0.1 mg/(kg·h) to 2.0 mg/(kg·h), or a range of 0.1 mg/(kg·h) to 1.0 mg/(kg·h).

In a modified embodiment of the method for general anesthetization or sedation in a mammal according to the present invention, a loading dose of the compound of general formula (I) or a prodrug thereof is administered over a period not longer than 10 min, preferably not longer than 2 min. The period over which a maintenance dose is administered depends on the period required to maintain general anesthesia or sedation in a mammal. Furthermore, a compound of general formula (I), or a stereoisomer, a pharmaceutically acceptable salt, or a prodrug thereof, is optionally administered in a manner selected from one or more of single administration, multiple administrations, continuous administration, and target-controlled infusion, preferably target-controlled infusion.

Based on the nature of clinical medication, a loading dose for inducing general anesthesia or sedation is often administered by single injection. A maintenance dose for maintaining general anesthesia or sedation may be administered by multiple injections, which may however result in a zig-zag fluctuation in the blood drug level and therefore the fluctuation in the depth of anesthesia in the subject. Hence, in clinical practice, a maintenance dose is often administered by continuous infusion or target-controlled infusion, to avoid considerable fluctuation between peaks and troughs of the blood drug level resulting from discrete administrations, so that the depth of anesthesia is easily controlled and the anesthesia course is stable.

The compound of general formula (I), or a stereoisomer, a pharmaceutically acceptable salt, or a prodrug thereof is used in a method for inducing or maintaining general anesthesia or sedation in a mammal, and may be administered by a variety of administration routes, including but not limited to those selected from intravenous injection, intra-arterial injection, intramuscular injection, transdermal, buccal, parenteral intraperitoneal, rectal, transbuccal, intranasal, inhalation, topical, subcutaneous, intra-adipose, intra-articular, intraperitoneal, and intrathecal administrations. In a particular modified embodiment, it is administered by intravenous injection.

The compound of general formula (I) is a $GABA_A$ receptor agonist. When activated, the $GABA_A$ receptor undergoes conformational changes on a cell membrane and opens the receptor channel, through which chloride anions can pass along a voltage and concentration gradient and hyperpolarize the cell, so that the depolarizing effect of excitatory neurotransmitters and the possibility of producing an action potential are reduced. Therefore, this receptor mainly exerts an inhibitory effect and reduces the activity of neurons. A $GABA_A$ receptor agonist can generally produce anxiolytic, anticonvulsant, amnesic, sedative, hypnotic, anesthetic, euphoric, and muscle relaxing effects, and the like. In a particular modified embodiment, it is administered for inducing or maintaining general anesthesia or sedation in a mammal.

An embodiment of the present invention relates to a method for inducing or maintaining general anesthesia or sedation in a mammal, comprising: concomitantly administering to the mammal an effective dose of a compound of general formula (I) and one or more additional active ingredients other than the compound of general formula (I), wherein the additional active ingredients are selected from drugs having sedative hypnotic activity or anesthetic adjuvant drugs, wherein the effective dose includes a loading dose and/or a maintenance dose. In a modified embodiment, the loading dose of the compound of general formula (I) is optionally selected from a range of 0.01 mg/kg to 15.0 mg/kg, a range of 0.05 mg/kg to 15.0 mg/kg, a range of 0.05 mg/kg to 10.0 mg/kg, a range of 0.1 mg/kg to 12.0 mg/kg, a range of 0.1 mg/kg to 10.0 mg/kg, a range of 0.1 mg/kg to 8.0 mg/kg, a range of 0.1 mg/kg to 6.0 mg/kg, a range of 0.1 mg/kg to 5.0 mg/kg, a range of 0.1 mg/kg to 4.0 mg/kg, a range of 0.1 mg/kg to 3.0 mg/kg, a range of 0.1 mg/kg to 2.0 mg/kg, a range of 0.1 mg/kg to 1.0 mg/kg, a range of 0.1 mg/kg to 0.8 mg/kg, a range of 0.1 mg/kg to 0.6 mg/kg, a range of 0.1 mg/kg to 0.5 mg/kg, a range of 0.1 mg/kg to 0.3 mg/kg, or a range of 0.1 mg/kg to 0.2 mg/kg; and the maintenance dose of the compound of general formula (I) is optionally selected from a range of 0.01 mg/(kg·h) to 20.0 mg/(kg·h), a range of 0.01 mg/(kg·h) to 15.0 mg/(kg·h), a range of 0.01 mg/(kg·h) to 10.0 mg/(kg·h), a range of 0.02 mg/(kg·h) to 6.0 mg/(kg·h), a range of 0.05 mg/(kg·h) to 6.0 mg/(kg·h), a range of 0.05 mg/(kg·h) to 5.0 mg/(kg·h), a range of 0.05 mg/(kg·h) to 4.0 mg/(kg·h), a range of 0.1 mg/(kg·h) to 4.0 mg/(kg·h), a range of 0.1 mg/(kg·h) to 3.0 mg/(kg·h), a range of 0.1 mg/(kg·h) to 2.0 mg/(kg·h), or a range of 0.1 mg/(kg·h) to 1.0 mg/(kg·h).

In a modified embodiment of the method for general anesthetization or sedation in a mammal according to the present invention, the method further comprises administering to the mammal one or more additional active ingredients other than the compound of general formula (I), wherein the additional active ingredients are selected from drugs having sedative hypnotic activity or anesthetic adjuvant drugs.

In a modified embodiment of the method for general anesthetization or sedation in a mammal according to the present invention, the additional active ingredients are selected from a γ-aminobutyric acid receptor agonist, a γ-aminobutyric acid receptor activator, an M-receptor antagonist, a $N_2$-receptor antagonist, 5-hydroxytryptophan-3 ($5-HT_3$) receptor antagonist, a $Na^+$ channel antagonist, or an opioid receptor agonist.

In a modified embodiment of the method for general anesthetization or sedation in a mammal according to the present invention, the additional active ingredients are selected from intravenous anesthetics, inhalation anesthetics, or anesthetic adjuvant agents.

In a particular modified embodiment of the method for general anesthetization or sedation in a mammal according to the present invention, the intravenous anesthetics are optionally selected from propofol, fospropofol sodium, midazolam, ketamine, thiopental sodium, sodium oxybate, or etomidate, including their pharmaceutically acceptable salts;

the inhalation anesthetics are optionally selected from sevoflurane, isoflurane, enflurane, desflurane, methoxyflurane, or nitrous oxide;

the anesthetic adjuvant agents are optionally selected from sedative hypnotics, anticholinergics, muscle relaxants, antiemetics, local anesthetics or analgesics.

In a particular modified embodiment of the method for general anesthetization or sedation in a mammal according to the present invention, the sedative hypnotics are optionally selected form diazepam, fluazepam, chlordiazepoxide, estazolam, clonazepam, glutethimide, meprobamate, buspirone, midazolam, dexmedetomidine, droperidol, promethazine, chlorpromazine, barbital, phenobarbital, pentobarbital, amobarbital, secobarbital or thiopental sodium, including their pharmaceutically acceptable salts; preferably diazepam, fluazepam, midazolam, dexmedetomidine, promethazine or chlorpromazine, including their pharmaceutically acceptable salts;

the anticholinergics are optionally selected from atropine or scopolamine, including their pharmaceutically acceptable salts;

the muscle relaxants are optionally selected from vecuronium bromide, rocuronium bromide, pancuronium bromide, pipecuronium bromide, mivacurium chloride, atracurium or succinylcholine, including their pharmaceutically acceptable salts;

preferably vecuronium bromide, rocuronium bromide, pancuronium bromide, or pipuronium, including their pharmaceutically acceptable salts;

the antiemetics are optionally selected from tropisetron, palonosetron, granisetron, dolasetron, scopolamine, cyclizine or metoclopramide, including their pharmaceutically acceptable salts; preferably tropisetron or scopolamine, including their pharmaceutically acceptable salts;

the local anesthetics are optionally selected from lidocaine, ropivacaine, prilocaine, bupivacaine, articaine or dyclonine, including their pharmaceutically acceptable salts;

preferably lidocaine or ropivacaine, including their pharmaceutically acceptable salts;

the analgesics are selected from fentanyl, remifentanil, sufentanil, alfentanil, morphine, pethidine, dezocine, butorphanol, oxycodone or nefopam, including their pharmaceutically acceptable salts; preferably fentanyl, remifentanil, sufentanil, alfentanil, or pethidine, including their pharmaceutically acceptable salts; more preferably fentanyl or remifentanil, including their pharmaceutically acceptable salts.

In a modified embodiment of the method for general anesthetization or sedation in a mammal according to the present invention, the compound of general formula (I) is administered in combination with alfentanil, fentanyl, or remifentanil, including their pharmaceutically acceptable salts.

In each of the above embodiments, preferred embodiments, or modified embodiments about the method for general anesthetization or sedation in a mammal, the pharmaceutically acceptable salts of the compound of general formula (I) are selected from alkali metal salts or alkali earth metal salts, wherein the alkali metal is selected from Na, K or Li, and the alkali earth metal is selected from Ca.

An embodiment of the present invention relates to a pharmaceutical composition provided as a liquid formulation or a lyophilized formulation, wherein the liquid formulation or lyophilized formulation comprises a compound of general formula (I), or a stereoisomer, a pharmaceutically acceptable salt, or a prodrug thereof, at a concentration in the liquid formulation or in a solution to be lyophilized into the lyophilized formulation of 0.1 mg/mL to 50.0 mg/mL, optionally 0.1 mg/mL to 40.0 mg/mL, optionally 0.5 mg/mL to 40.0 mg/mL, optionally 0.5 mg/mL to 30.0 mg/mL, optionally 1.0 mg/mL to 20.0 mg/mL, optionally 2.0 mg/mL to 20.0 mg/mL, optionally 3.0 mg/mL to 20.0 mg/mL, optionally 4.0 mg/mL to 20.0 mg/mL, optionally 5.0 mg/mL to 20.0 mg/mL, optionally 5.0 mg/mL to 15.0 mg/mL, and optionally 5.0 mg/mL to 10.0 mg/mL.

In a particular embodiment, a pharmaceutical composition is provided as a liquid formulation or a lyophilized formulation, and the liquid formulation or lyophilized formulation comprises a compound of general formula (I), or a stereoisomer, a pharmaceutically acceptable salt, or a prodrug thereof, at a concentration in the liquid formulation or in a solution to be lyophilized into the lyophilized formulation of any of 1.0 mg/mL, 2.0 mg/mL, 3.0 mg/mL, 4.0 mg/mL, 5.0 mg/mL, 6.0 mg/mL, 7.0 mg/mL, 8.0 mg/mL, 9.0 mg/mL, 10.0 mg/mL, 11.0 mg/mL, 12.0 mg/mL, 13.0 mg/mL, 14.0 mg/mL, 15.0 mg/mL, 16.0 mg/mL, 17.0 mg/mL, 18.0 mg/mL, 19.0 mg/mL, or 20.0 mg/mL.

The compound of general formula (I) in combination with one or more intravenous anesthetics and/or anesthetic adjuvant agents other than the compound of formula (I) produces excellent effects such as improved anesthetic quality, a reduced dose of the compound of formula (I) in the peroperative period, improved safety, good compliance of patients, reduced adverse effects, a reduced number of administrations of anesthetics, and more convenient induction of anesthesia.

In a modified embodiment, a pharmaceutical composition is provided as a liquid formulation or a lyophilized formulation, and the liquid formulation or lyophilized formulation further comprises one or more additional active ingredients other than the compound of general formula (I), wherein the additional active ingredients are selected from drugs having sedative hypnotic activity or anesthetic adjuvant drugs.

In an embodiment, in the pharmaceutical composition provided as a liquid formulation or a lyophilized formulation, the additional active ingredients are selected from a γ-aminobutyric acid receptor agonist, a γ-aminobutyric acid receptor activator, an M-receptor antagonist, a $N_2$-receptor antagonist, 5-hydroxytryptophan-3 receptor antagonist, a $Na^+$ channel antagonist, or an opium receptor agonist.

In an embodiment, in the pharmaceutical composition provided as a liquid formulation or a lyophilized formulation, the additional active ingredients are selected from intravenous anesthetics, and/or anesthetic adjuvant agents.

In an embodiment, the pharmaceutical composition provided as a liquid formulation or a lyophilized formulation comprises the compound of general formula (I) and one or more intravenous anesthetics and/or anesthetic adjuvant agents other than the compound of general formula (I). In the liquid formulation or in a solution to be lyophilized into the lyophilized formulation, the compound of general formula (I) is contained at a concentration of 0.1 mg/mL to 50.0 mg/mL, optionally 0.1 mg/mL to 40.0 mg/mL, optionally 0.5 mg/mL to 40.0 mg/mL, optionally 0.5 mg/mL to 30.0 mg/mL, optionally 1.0 mg/mL to 20.0 mg/mL, optionally 2.0 mg/mL to 20.0 mg/mL, optionally 3.0 mg/mL to 20.0 mg/mL, optionally 4.0 mg/mL to 20.0 mg/mL, optionally 5.0 mg/mL to 20.0 mg/mL, optionally 5.0 mg/mL to 15.0 mg/mL, and optionally 5.0 mg/mL to 10.0 mg/mL. In a particular embodiment of the pharmaceutical composition provided as a liquid formulation or a lyophilized formulation, in the liquid formulation or in a solution to be lyophilized into the lyophilized formulation, the compound of general formula (I) is contained at a concentration of any of 1.0 mg/mL, 2.0 mg/mL, 3.0 mg/mL, 4.0 mg/mL, 5.0 mg/mL, 6.0 mg/mL, 7.0 mg/mL, 8.0 mg/mL, 9.0 mg/mL, 10.0 mg/mL, 11.0 mg/mL, 12.0 mg/mL, 13.0 mg/mL, 14.0 mg/mL, 15.0 mg/mL, 16.0 mg/mL, 17.0 mg/mL, 18.0 mg/mL, 19.0 mg/mL, or 20.0 mg/mL.

In a modified embodiment, in each of the above embodiments about the pharmaceutical composition, the intravenous anesthetics are optionally selected from propofol, fospropofol sodium, midazolam, ketamine, thiopental sodium, sodium oxybate, or etomidate, including their pharmaceutically acceptable salts; preferably midazolam or etomidate, including their pharmaceutically acceptable salts.

In a modified embodiment, in each of the above embodiments about the pharmaceutical composition, the anesthetic adjuvant agents are optionally selected from sedative hypnotics, anticholinergics, muscle relaxants, antiemetics, local anesthetics or analgesics.

In a modified embodiment, in each of the above embodiments about the pharmaceutical composition, the sedative hypnotics are optionally selected form diazepam, fluazepam, chlordiazepoxide, estazolam, clonazepam, glutethimide, meprobamate, buspirone, midazolam, dexmedetomidine, droperidol, promethazine, chlorpromazine, barbital, phenobarbital, pentobarbital, amobarbital, secobarbital or thiopental sodium, including their pharmaceutically acceptable salts; preferably diazepam, fluazepam, midazolam, dexmedetomidine, promethazine or chlorpromazine, including their pharmaceutically acceptable salts;

the anticholinergics are optionally selected from atropine or scopolamine, including their pharmaceutically acceptable salts;

the muscle relaxants are optionally selected from vecuronium bromide, rocuronium bromide, pancuronium bromide, pipecuronium bromide, mivacurium chloride, atracurium or succinylcholine, including their pharmaceutically acceptable salts;

preferably vecuronium bromide, rocuronium bromide, pancuronium bromide, or pipecuronium bromide, including their pharmaceutically acceptable salts;

the antiemetics are optionally selected from tropisetron, palonosetron, granisetron, dolasetron, scopolamine, cyclizine or metoclopramide, including their pharmaceutically acceptable salts; preferably tropisetron or scopolamine, including their pharmaceutically acceptable salts;

the local anesthetics are optionally selected from lidocaine, ropivacaine, prilocaine, bupivacaine, articaine or dyclonine, including their pharmaceutically acceptable salts; preferably lidocaine or ropivacaine, including their pharmaceutically acceptable salts; and the analgesics are selected from fentanyl, remifentanil, sufentanil, alfentanil, morphine, pethidine, dezocine, butorphanol, oxycodone and nefopam, including their pharmaceutically acceptable salts; preferably fentanyl, remifentanil, sufentanil, alfentanil, or pethidine, including their pharmaceutically acceptable salts; more preferably fentanyl or remifentanil, including their pharmaceutically acceptable salts.

In a particular embodiment, the pharmaceutical composition contains local anesthetic(s) and the compound of general formula (I), wherein the local anesthetic(s) is/are optionally selected from one or more of lidocaine, ropivacaine, prilocaine, bupivacaine, articaine or dyclonine, including their pharmaceutically acceptable salts, and preferably lidocaine or ropivacaine, including their pharmaceutically acceptable salts; and the compound of general formula (I) includes its stereoisomer, pharmaceutically acceptable salt, or prodrug.

In a particular embodiment, the pharmaceutical composition contains opioid analgesic(s) and the compound of general formula (I), wherein the opioid analgesic(s) is/are optionally selected from one or more of fentanyl, remifentanil, sufentanil, alfentanil, morphine, dezocine, butorphanol and oxycodone, including their pharmaceutically acceptable salts; preferably fentanyl, remifentanil, sufentanil, alfentanil, or pethidine, including their pharmaceutically acceptable salts; more preferably fentanyl or remifentanil, including their pharmaceutically acceptable salts; and the compound of general formula (I) includes its stereoisomer, pharmaceutically acceptable salt, or prodrug.

In each of the above embodiments and their modified embodiments about the pharmaceutical composition, the liquid formulation or lyophilized formulation is optionally suitable for administration by intravenous injection.

In each of the above embodiments and their modified embodiments about the pharmaceutical composition, the liquid formulation is optionally an aqueous solution suitable for intravenous injection, or a fat emulsion suitable for intravenous injection.

Also, in each of the above embodiments and their modified embodiments about the pharmaceutical composition, the pharmaceutical composition contains a compound of general formula (I), or a stereoisomer, a pharmaceutically acceptable salt, or a prodrug thereof. In a particular modified embodiment, the pharmaceutically acceptable salts of the compound of general formula (I) are selected from alkali metal salts or alkali earth metal salts, wherein the alkali metal is selected from Na, K or Li, and the alkali earth metal is selected from Ca. In another particular modified embodiment, the prodrug of the compound of general formula (I) is a compound of general formula (II) below:

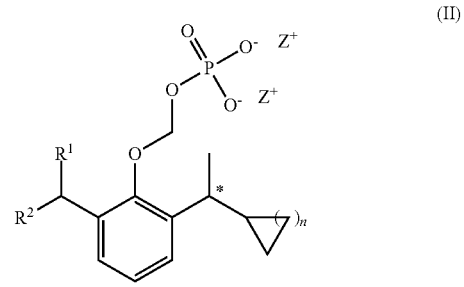

wherein $R^1$, $R^2$ and n have the same definitions as those in general formula (I);

$Z^+$ is each independently selected from $H^+$, an alkali metal ion or an ammonium ion;

wherein the alkali metal ion is selected from $Na^+$ or $K^+$, preferably $Na^+$.

Also, in each of the above embodiments and their modified embodiments about the pharmaceutical composition, the pharmaceutical composition may be used for pharmacologic action performed by $GABA_A$ receptor agonists, for example, for inducing or maintaining general anesthesia or sedation in a mammal, and/or for producing an anxiolytic, anticonvulsant, amnesic, sedative, hypnotic, anesthetic, euphoric, and/or muscle relaxing effect. In a particular modified embodiment, the pharmaceutical composition may be used for inducing or maintaining general anesthesia or sedation in a mammal.

Also, in each of the above embodiments and their modified embodiments about the pharmaceutical composition, the pharmaceutical composition may be administered by administration routes including but not limited to those selected from intravenous injection, intra-arterial injection, intramuscular injection, transdermal, buccal, parenteral intraperitoneal, rectal, transbuccal, intranasal, inhalation, topical, subcutaneous, intra-adipose, intra-articular, intraperitoneal, and intrathecal administrations. In a particular modified embodiment, it is administered by intravenous injection.

An embodiment of the present invention provides a kit comprising: a single dose or multiple doses of the pharmaceutical composition according to the present invention, and a package insert showing information in one or more forms, wherein the information is selected from indication(s) for administration of the pharmaceutical composition, storage information and dosing information of the pharmaceutical composition, and instruction about how to administer the pharmaceutical composition.

An embodiment of the present invention provides an article comprising: a single dose or multiple doses of the pharmaceutical composition according to the present invention, and a packaging material.

In a modified embodiment, the article further comprises a packaging material, such as container(s) for accommodating the single dose or multiple doses of the pharmaceutical composition and/or tag(s), wherein the tag(s) show one or more of: indication(s) for administration of the pharmaceutical composition, storage information, dosing information, and/or instruction about how to administer the pharmaceutical composition.

An embodiment of the present invention provides use of a compound of general formula (I), or a stereoisomer, a pharmaceutically acceptable salt, or a prodrug thereof, in the manufacture of a medicament for producing an anxiolytic, anticonvulsant, amnesic, sedative, hypnotic, anesthetic, euphoric, and/or muscle relaxing effect. A modified embodiment provides use of a compound of general formula (I), or a stereoisomer, a pharmaceutically acceptable salt, or a prodrug thereof, in the manufacture of a medicament for inducing or maintaining general anesthesia or sedation in a mammal.

An embodiment of the present invention provides use of a compound of general formula (I), in combination with one or more additional active ingredients other than the compound of general formula (I), in the manufacture of a medicament for producing an anxiolytic, anticonvulsant, amnesic, sedative, hypnotic, anesthetic, euphoric, and/or muscle relaxing effect, wherein the additional active ingredients have a sedative hypnotic effect or an anesthetic adjuvant effect. A modified embodiment provides use of a compound of general formula (I), in combination with one or more intravenous anesthetics and/or anesthetic adjuvant agents other than the compound of general formula (I), in the manufacture of a medicament for inducing or maintaining general anesthesia or analgesia in a mammal.

An embodiment of the present invention provides use of a compound of general formula (I) in the manufacture of a pharmaceutical composition for inducing or maintaining general anesthesia or analgesia in a mammal, wherein the pharmaceutical composition comprises the compound of general formula (I) and one or more additional active ingredients other than the compound of general formula (I) having a sedative hypnotic effect or an anesthetic adjuvant effect.

An embodiment of the present invention provides use of one or more additional active ingredients other than the compound of general formula (I) in the manufacture of a medicament for general anesthetization or analgesia in a mammal, wherein the medicament comprises the compound of general formula (I) in combination with the one or more additional active ingredients.

In each of the above embodiments or modified embodiments about the use, the additional active ingredients are selected from intravenous anesthetics and/or anesthetic adjuvant agents.

In a modified embodiment about the above use, the pharmaceutically acceptable salts of the compound of general formula (I) are selected from alkali metal salts or alkali earth metal salts, wherein the alkali metal is selected from Na, K or Li, and the alkali earth metal is selected from Ca.

In a modified embodiment about the above use, the prodrug of the compound of general formula (I) is a compound of general formula (II) below:

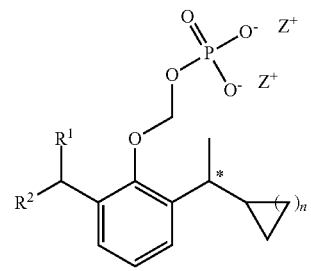

wherein $R^1$, $R^2$ and n have the same definitions as those in general formula (I);

$Z^+$ is each independently selected from $H^+$, an alkali metal ion or an ammonium ion;

wherein the alkali metal ion is selected from $Na^+$ or $K^+$, preferably $Na^+$.

About all of the above embodiments and modified embodiments, it should be understood that these embodiments and modified embodiments are to be construed as open-ended, for example, the method may include further steps other than those described, including administering to the patient other pharmaceutically active substances. Similarly, unless otherwise indicated, the pharmaceutical composition, kit and article may further comprise other materials, including other pharmaceutically active substances.

Hereinafter is a detailed description of embodiments of the present invention.

Unless otherwise indicated, the compound of general formula (I) according to the present invention is

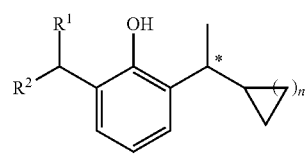

wherein $R^1$ and $R^2$ are each independently selected from a $C_{1-4}$ alkyl or a $C_{3-6}$ cycloalkyl; and n is 1 or 2.

In a more preferred embodiment of the compound of general formula (I), $R^1$ is selected from methyl, ethyl or isopropyl; $R^2$ is selected from methyl, ethyl, isopropyl or cyclopropyl; n is 1 or 2.

The compound of general formula (I) is more preferably selected from

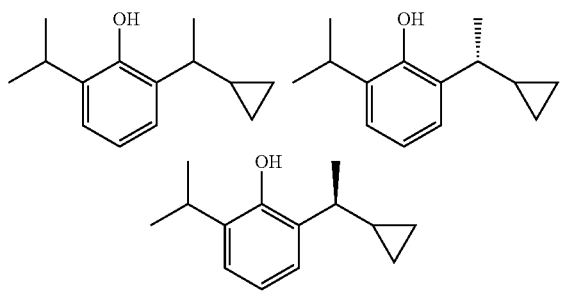

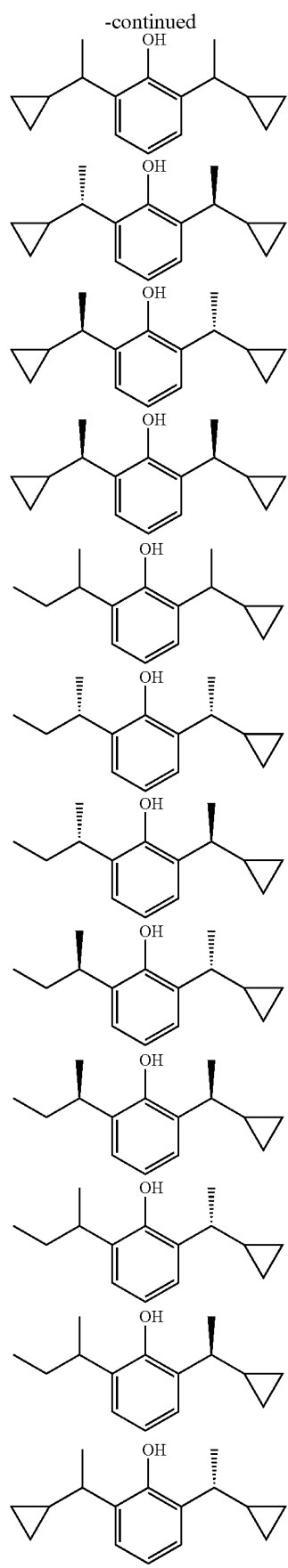
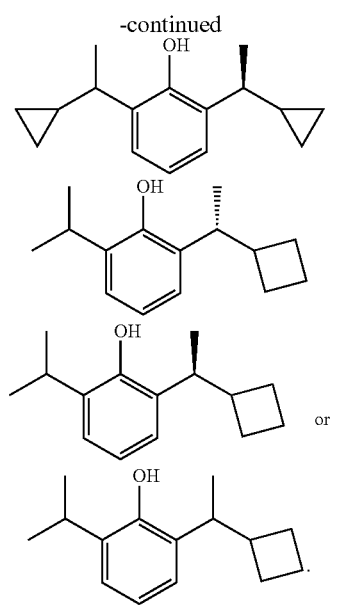
The compound of general formula (I) is particularly preferably selected from
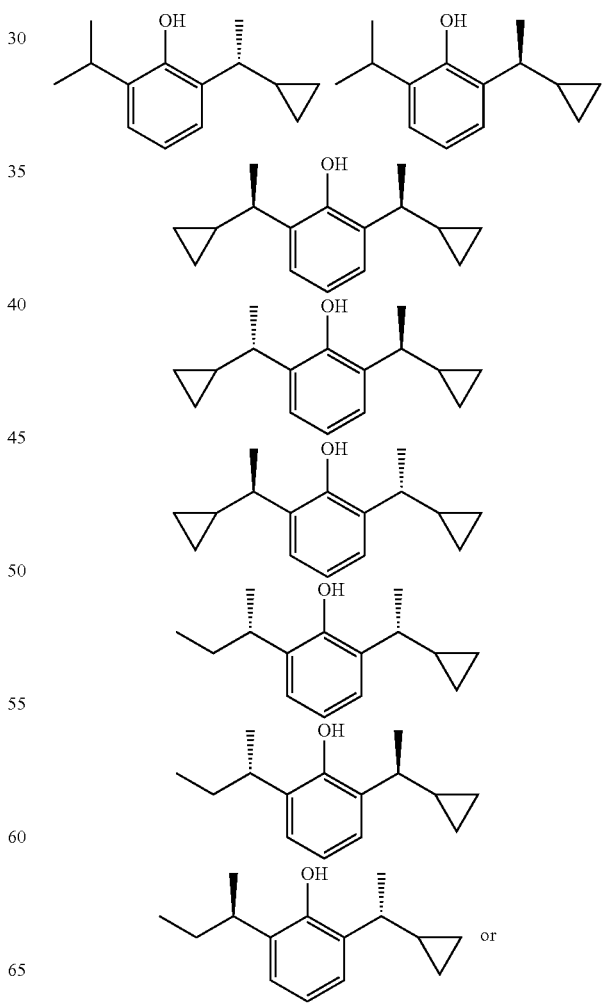

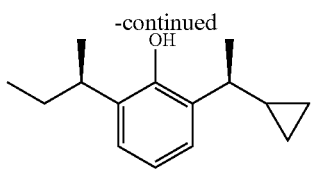

Unless otherwise indicated, the terms used throughout the specification and claims have the following definitions.

"General anesthesia" refers to temporary inhibition of the central nervous system after a drug enters the body through the respiratory tract or by intravenous or intramuscular injection, and is clinically manifested as unconsciousness, general analgesia, amnesia, reflex inhibition, and skeletal muscle relaxation. The degree of inhibition of the central nervous system is associated with the blood drug level and can be controlled and adjusted. Such inhibition is completely reversible. After the drug is metabolized or excreted by the body, the consciousness and various reflexes of the subject recover gradually.

"Sedation" refers to settlement of mental excitement and reduction in physiological functions after administration of a drug.

A "mammal" refers to body furred, relatively agile, homeothermal, and viviparous vertebrates having a diaphragm, represents the highest animal species with the most complex anatomic structure, functions, and behaviors among vertebrates, and is named after their ability to breastfeeding young off-springs with milk secreted from their mammary glands. Mammals include, but are not limited to, mice, rats, cows, pigs, sheep, buffalo, dogs, cats, horses, apes, monkeys, gorillas and humans, preferably humans.

An "effective dose" refers to a drug dose which is sufficient to induce or maintain anesthesia or sedation when administered.

A "loading dose" refers to a drug dose that allows, after a single administration, an anesthesia or sedation effect to rapidly reach its peak value.

A "maintenance dose" refers to a drug dose required to maintain an anesthetized or sedated state, and is expressed as an administering rate in mg/(kg·h) or mg/(m²·h).

"Single administration" refers to administration of a certain dose of drug at one time so that an appropriate depth of anesthesia or sedation is rapidly reached, and is generally used for inducing anesthesia or sedation and in small and short surgeries.

"Multiple administrations" refer to an initial administration of a certain dose of drug by intravenous injection such that an appropriate depth of anesthesia or sedation is reached, followed by additional administration(s) of the drug according to the response of the subject under anesthesia or sedation and the requirements of surgeries, to maintain a certain anesthetic or sedative depth.

"Continuous administration" refers to continuous dripping or pumping of a drug at various rates after anesthesia or sedation is induced in a subject, to maintain the depth of the anesthesia or sedation. The rate of the administration may be set manually or by a computer. By models and theories in pharmacokinetics, one can calculate the drug dose to be administered as required to reach a satisfactory and desirable blood drug level over a certain period.

"Target-controlled infusion" refers to intravenous infusion of a drug, in which the course and effects of the drug in the body are simulated in a computer based on pharmacokinetic and pharmacodynamics theories, to find the most reasonable dosing regime and in turn to control the drug injection pump such that the blood drug level or the drug concentration at the effecting site is stabilized at an expected value (target concentration), and the depth of anesthesia or sedation can be controlled and the administering system may be adjusted at any time according to clinical needs.

"Intravenous anesthetics" refer to drugs that are intravenously injected into a body and act on the central nervous system through blood circulation to produce general anesthesia. Non-limiting examples thereof include propofol, fospropofol sodium, midazolam, ketamine, thiopental sodium, propofol, sodium oxybate, and etomidate, including their pharmaceutically acceptable salts.

"Inhalation anesthetics" refer to drugs that are inhaled through the respiratory tract and suppress the central nervous system through blood circulation to produce general anesthesia. Non-limiting examples thereof include sevoflurane, isoflurane, enflurane, desflurane, methoxyflurane, and nitrous oxide.

"Anesthetic adjuvant agents" are drugs used for composite anesthetization to assist general anesthetics in exerting a better effect. Non-limiting examples thereof include sedative hypnotics, anticholinergics, muscle relaxants, antiemetics, local anesthetics and analgesics.

"Sedative hypnotics" refer to drugs capable of causing sedation or similar physiologic sleep. With a small dose, it causes sedation, while with a large dose, it may cause hypnosis. Non-limiting examples thereof include diazepam, fluazepam, chlordiazepoxide, estazolam, clonazepam, glutethimide, meprobamate, buspirone, midazolam, dexmedetomidine, droperidol, barbital, phenobarbital, pentobarbital, amobarbital, secobarbital, or thiopental sodium, including their pharmaceutically acceptable salts.

"Anticholinergics" refer to drugs that block cholinoceptors from binding the transmitter acetylcholine, thereby exhibiting an opposite effect to cholinomimetics. Non-limiting examples thereof include atropine, scopolamine, penehyclidine and glycopyrrolate, including their pharmaceutically acceptable salts.

"Muscle relaxants" refer to drugs capable of selectively acting on $N_2$ receptors on the telolemma of motor nerves to cause reversible relaxation of skeletal muscles. Non-limiting examples thereof include vecuronium bromide, rocuronium bromide, pancuronium bromide, pipecuronium bromide, mivacurium chloride, atracurium and succinylcholine, including their pharmaceutically acceptable salts.

"Antiemetics" refer to drugs preventing or alleviating nausea or vomiting. Non-limiting examples thereof include tropisetron, palonosetron, granisetron, dolasetron, scopolamine, cyclizine and metoclopramide, including their pharmaceutically acceptable salts.

"Local anesthetics" refer to drugs that reversibly block production and transmission of sensory nerve impulses at a drugged local site. Non-limiting examples thereof include procaine, chloroprocaine, tetracaine, benzocaine, lidocaine, ropivacaine, prilocaine, bupivacaine, icticaine, mepivacaine, and articaine, including their pharmaceutically acceptable salts.

"Analgesics" refer to drugs that act mainly on the central nervous system, selectively eliminate or relieve pain, do not significantly influence other senses (for example auditory perception, vision, and touch sensation), and keep consciousness. Non-limiting examples thereof are selected from fentanyl, remifentanil, sufentanil, alfentanil, morphine, pethidine, dezocine, butorphanol, oxycodone and nefopam, including their pharmaceutically acceptable salts.

"Opioid analgesics" refer to drugs capable of activating opioid receptors to eliminate or alleviate pain and change the emotional reaction to pain. Non-limiting examples thereof are selected from alphaprodine, fentanyl, remifentanil, sufentanil, alfentanil, pethidine, morphine, dezocine, butorphanol, oxycodone, allylprodine, anileridine, benzyl morphine, buprenorphine, butorphanol, clonitazene, cyclazocine, desomorphine, dextromoramide, dezocine, diampromide, diamorphine, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethyl morphine, etonitazene, heroin, hydromorphone, hydroxypethidine, meptazinol, metazocine, methadone, metopon, myrophine, nalbuphine, nicomorphine, norlevorphanol, normethadone, nalorphine, normorphine, oxymorphone, pentazocine, phenazocine, tramadol, tilidine, dextropropoxyphene, and properidine, including their pharmaceutically acceptable salts.

A "pharmaceutical composition" refers to a mixture formed by compound(s) of general formula (I), or a stereoisomer, a pharmaceutically acceptable salt, or a prodrug thereof according to the present invention and additional chemical components, wherein the "additional chemical components" refer to pharmaceutically acceptable carriers, excipients and/or one or more other drugs.

"Carrier" means a material that does not cause significant stimulation to an organism and does not eliminate the biological activity and characteristics of an administered compound.

"Excipient" means an inert substance added into a pharmaceutical composition to facilitate administration of a compound. Non-limiting examples thereof include calcium carbonate, calcium phosphate, sugar, starch, cellulose derivatives (including microcrystalline cellulose), gelatin, vegetable oils, polyethylene glycols, diluent, a granulating agent, lubricant, binder and disintegrant.

A "pharmaceutically acceptable salt" refers to a safe, nontoxic salt which is not undesirable in biology or other aspects, and includes salts which are acceptable for medication in veterinary medicine or human medicine and have expected pharmaceutical activity. Such salts include, but are not limited to, acid-adduct salts formed with inorganic acids such as hydrochloric acid, hydrobromic acid, sulfuric acid, nitric acid, and phosphoric acid; or acid-adduct salts formed with organic acids such as acetic acid, trifluoroacetic acid, propionic acid, caproic acid, heptanoic acid, cyclopentane-propionic acid, pyruvic acid, lactic acid, malonic acid, succinic acid, malic acid, maleic acid, fumaric acid, tartaric acid, citric acid, benzoic acid, O-(4-hydroxybenzoyl)benzoic acid, cinnamic acid, mandelic acid, methanesulfonic acid, ethanesulfonic acid, trifluoromethanesulfonic acid, 1,2-ethanedisulfonic acid, benzenesulfonic acid, p-chlorobenzenesulfonic acid, 2-naphthalenesulfonic acid, p-toluenesulfonic acid, camphor sulfonic acid, 4-methylbicyclo[2.2.2]oct-2-ene-1-carboxylic acid, glucuronic acid, glucoheptonic acid, 3-phenylpropionic acid, trimethylacetic acid, t-butylacetic acid, dodecylsulfuric acid, glutamic acid, hydroxynaphthoic acid, salicylic acid, stearic acid, citric acid, lysine, arginine, aspartic acid, 2-hydroxypropionic acid, oxalic acid, and muconic acid.

Pharmaceutically acceptable salts also include, but are not limited to, alkali-adduct salts which may be formed when available acidic protons can react with an organic or inorganic base, and may be selected from salts of Al, Ca, Li, Mg, K, Na and Zn. Acceptable inorganic bases include, but are not limited to, sodium hydroxide, sodium bicarbonate, sodium carbonate, potassium hydroxide, potassium bicarbonate, potassium carbonate, lithium hydroxide, lithium carbonate, potassium phosphate, sodium phosphate, disodium hydrophosphate, dipotassium hydrophosphate, calcium hydroxide and aluminum hydroxide. Acceptable organic bases include, but are not limited to, ammonia, isopropylamine, trimethylamine, diethylamine, triethylamine, tripropylamine, tetramethylamine, diethanolamine, ethanolamine, dimethylethanolamine, 2-dimethylaminoethanol, 2-diethylaminoethanol, dicyclohexylamine, caffeine, procaine, choline, betaine, benethamine penicillin, ethylenediamine, glucosamine, N-methylglucamine, theobromine, triethanolamine, tromethamine, purine, piperazine, piperidine, N-ethylpiperidine, and polyamine resins.

A "prodrug" means a compound that can be converted upon in vivo metabolism into a biologically active form of the compound according to the present invention. A prodrug according to the present invention is prepared by modification of the phenol group(s) of the compound according to the present invention. Such a modification can be removed in vivo or by conventional operations, so as to produce the parent compound. When a prodrug according to the present invention is administered to a mammalian individual, it is cleaved to expose free hydroxyl(s).

A "stereoisomer" refers to an isomer of a molecule having its atoms in a different spatial arrangement, including cis-trans-isomer, enantiomer, and conformer.

The term "optional" or "optionally" means the event or situation modified by this term may but does not certainly happen, including both the case where the event or situation happens and the case not. For example, "a heterocyclic group optionally substituted with an alkyl" means that the alkyl may be present but is not necessarily present, including both the case where the heterocyclic group is substituted with an alkyl and the case where the heterocyclic group is not substituted with an alkyl.

$ED_{50}$ (median effective dose): dose required to cause 50% of animals to lose their righting reflex in a test.

$ED_{95}$ (95% effective dose): dose required to cause 95% of animals to lose their righting reflex in a test.

$LD_{50}$ (median lethal dose): dose required to cause 50% of animals to die in a test.

$LD_5$ (5% lethal dose): dose required to cause 5% of animals to die in a test.

Anesthesia induction time and anesthesia maintenance time: time recording was started from drug administration, and general symptoms and changes in administration sites and respiration of animals were closely observed. If a normal animal was able to immediately body-right after being pushed over or made lying on its back, such a reflex was determined as the righting reflex. Otherwise, loss of the righting reflex and the time of loss were recorded, and a reflex recovery time was recorded when the animal restored the righting reflex. The period from finishing of drug administration until loss of the righting reflex was recorded as the anesthesia induction time, and the period from loss of the righting reflex until recovery of the righting reflex was recorded as the anesthesia maintenance time.

TI (therapeutic index, i.e. $LD_{50}/ED_{50}$), SI (safety index, i.e. $LD_5/ED_{95}$).

MTD (maximum tolerated dose): the maximum dose able to cause 100% of animals to loss the righting index without death.

"w/v %" refers to the weight of each component (g)/the volume of formulation (100 ml).

BRIEF DESCRIPTION OF THE DRAWINGS

FIG. 1 is the X-ray single-crystal diffraction spectrum of compound 7C.

DETAILED DESCRIPTION OF THE DISCLOSURE

The technical solutions of the present invention will be described below in detail in conjunction with the Drawings and Examples. However, the scope of protection of the present invention includes but is not limited to this.

Structures of compounds were determined by nuclear magnetic resonance (NMR) and/or mass spectrometry (MS). NMR shifts (δ) are shown in the unit of $10^{-6}$ (ppm). For NMR measurement, NMR spectrometers (Bruker Avance III 400 and Bruker Avance 300) were used, deuterium-substituted dimethyl sulfoxide (DMSO-$d_6$), deuterium-substituted chloroform (CDCl$_3$) and deuterium-substituted methanol (CD$_3$OD) were used as solvents, and tetramethylsilane (TMS) was used as the internal standard.

For MS measurement, Agilent 6120B(ESI) and Agilent 6120B(APCI) were used.

For HPLC measurement, an Agilent 1260DA high pressure liquid phase chromatographer (Zorbax SB-C18 100× 4.6 mm, 3.5 μM) was used.

For the silica gel plate for thin-layer chromatography (TLC), HSGF254 (Yantai Yellow sea) or GF254 (Qingdao) silica gel plate was used. The silica gel plate used for TLC had the specification of 0.15 mm to 0.20 mm, while TLC for product separation and purification used a specification of 0.4 mm to 0.5 mm.

For column chromatography, generally employed was a 200 to 300-mesh silica gel from Yantai Yellow sea silica gels as a carrier.

Known starting materials in connection with the present invention can be synthesized following or using methods known in the art, or can be purchased from companies such as Titansci, Energy Chemical, Demochem (Shanghai), Kelong Chemical (Chengdu), Accela ChemBio, and J&K Scientific.

A N$_2$ atmosphere means that the reaction vessel is connected to a N$_2$ balloon of about 1 L in volume.

A H$_2$ atmosphere means that the reaction vessel is connected to a H$_2$ balloon of about 1 L in volume.

Hydrogenation reactions generally involve a vacuuming and H$_2$-charging operation repeating 3 times.

In the Example, unless particularly specified, reactions were carried out under a N$_2$ atmosphere.

In the Example, unless particularly specified, solutions refer to aqueous solutions.

In the Example, unless particularly specified, reaction temperatures are room temperature, most suitable room temperature as a reaction temperature is 20° C. to 30° C.

BHA: butylhydroxyanisole;
BHT: dibutylhydroxytoluene;
EDTA-2Na: disodium ethylenediaminetetraacetate Intermediate 1:
2-(1-cyclopropyl-1-hydroxyethyl)phenol (1b)

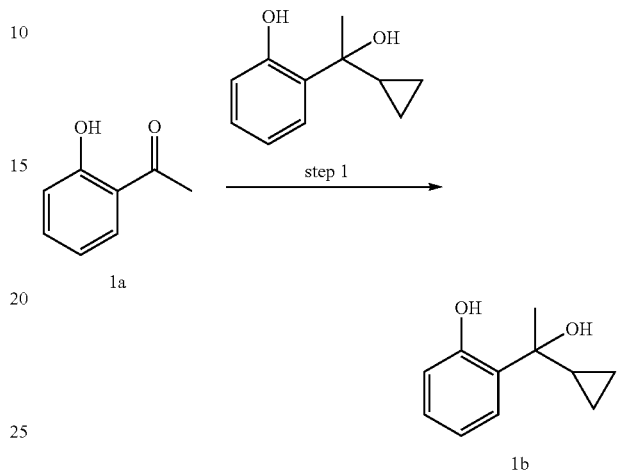

Under nitrogen protection, 2-hydroxy acetophenone 1a (15.00 g, 0.11 mole, Energy) and tetrahydrofuran (200 mL) were sequentially added to a reaction flask, then a 1M solution of cyclopropyl magnesium bromide in tetrahydrofuran (440 mL, 0.44 mol) was slowly added dropwise, followed by stirring at room temperature for 3 h, and the reaction was quenched with a saturated solution of ammonium chloride (50 mL) while in an ice bath. The reaction mixture was extracted twice with dichloromethane (125 mL×2). The organic phases were combined, washed with saturated brine (100 mL×3), dried over anhydrous sodium sulfate, filtered, and the filtrate was concentrated under reduced pressure. The residue was purified by silica gel column chromatography (n-hexane/ethyl acetate (v/v)=50:1) to give brown oily 2-(1-cyclopropyl-1-hydroxyethyl) phenol (1 b) (18.10 g, yield: 92%).

MS m/z (ESI): 177.1 [M−1].

$^1$H NMR (400 MHz, CDCl$_3$): δ 9.10 (s, 1H, Ar—OH), 7.22-7.14 (m, 2H, Ar—H), 6.91-6.80 (m, 2H, Ar—H), 1.50 (s, 3H, CH$_3$), 1.36-1.45 (m, 1H, CH), 0.36-0.68 (m, 4H, 2CH$_2$).

Intermediate 2:
2-bromo-6-(1-cyclopropyl-1-hydroxyethyl)phenol (1c)

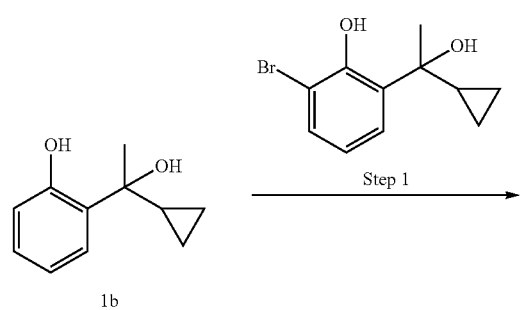

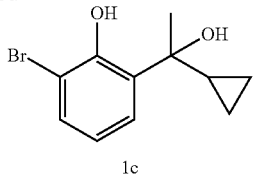

1c 2-(1-cyclopropyl-1-hydroxyethyl)phenol (1b) (12.72 g, 71.37 mmol, Intermediate 1), dichloromethane (125 mL), and diisopropylamine (0.73 g, 7.14 mmol) were sequentially added into a reaction flask in an ice bath, then N-bromosuccinimide (12.70 g, 71.37 mmol) was added thereto, followed by stirring for 15 h in an ice bath, and the reaction was stopped. The reaction mixture was washed with saturated brine (100 mL×3), and the organic phase was dried over anhydrous sodium sulfate, filtered, and the filtrate was concentrated under reduced pressure. The residue was purified by silica gel column chromatography (n-hexane/ethyl acetate (v/v)=50:1) to give white solid 2-bromo-6-(1-cyclopropyl-1-hydroxyethyl)phenol (1c) (7.52 g, yield: 41%, HPLC: 98.26%).

MS m/z (ESI): 254.9 [M−1], 257.9[M+1].

$^1$H NMR (400 MHz, CDCl$_3$): δ 9.53 (s, 1H, Ar—OH), 7.43 (dd, 1H, Ar—H), 7.20 (dd, 1H, Ar—H), 6.72 (t, 1H, Ar—H), 1.48 (s, 3H, CH$_3$), 1.41-1.38 (m, 1H, CH), 0.67 (m, 2H, CH$_2$), 0.54-0.42 (m, 2H, CH$_2$).

Intermediate 3:
2-bromo-6-(1-cyclopropylethyl)phenol (1d)

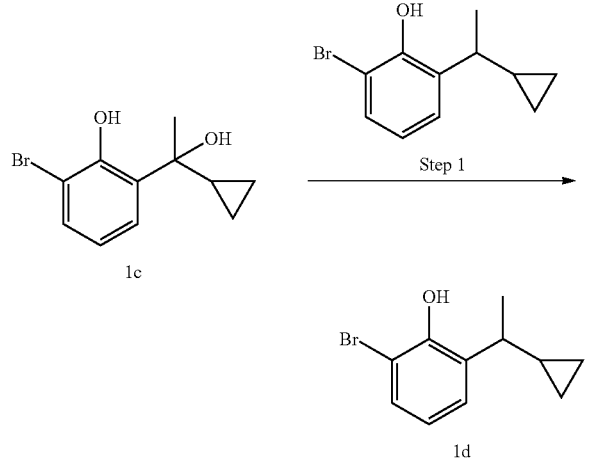

Under nitrogen protection, 2-bromo-6-(1-cyclopropyl-1-hydroxyethyl)phenol (1c) (0.25 g, 0.97 mmol), dichloromethane (15 mL) and triethylsilane (0.57 g, 4.86 mmol) were sequentially added to a reaction flask. In an ice bath, trifluoroacetic acid (1.11 g, 9.72 mmol) was added dropwise to the flask, followed by stirring for 15 h at room temperature, and then the reaction was stopped. The reaction solution was washed with a saturated sodium bicarbonate solution (30 mL×1) and then with saturated brine (30 mL×3), and the organic phase was dried over anhydrous sodium sulfate, filtered, and the filtrate was concentrated under reduced pressure. The residue was purified by silica gel column chromatography (n-hexane/ethyl acetate (v/v)=50: 1) to give colorless oily 2-bromo-6-(1-cyclopropylethyl)phenol (1d) (0.16 g, yield: 69%, HPLC: 96.89%).

MS m/z (ESI): 240.9 [M−1], 241.9[M+1].

$^1$H NMR (400 MHz, CDCl$_3$): δ 7.29 (dd, 1H, Ar—H), 7.25 (dd, 1H, Ar—H), 6.79 (t, 1H, Ar—H), 5.58 (s, 1H, OH), 2.48-2.40 (m, 1H, CH), 1.29 (d, 3H, CH$_3$), 1.07-0.98 (m, 1H, CH), 0.61-0.43 (m, 2H, CH$_2$), 0.26-0.16 (m, 2H, CH$_2$).

Intermediate 4:
S-2-bromo-6-(1-cyclopropylethyl)phenol (1e)

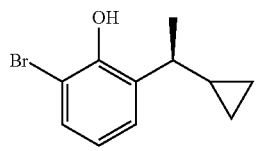

Intermediate 5:
R-2-bromo-6-(1-cyclopropylethyl)phenol (1f)

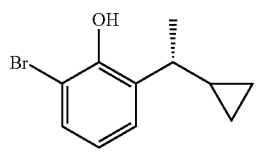

Preparation of Intermediates 4 and 5: Compound 1d (600 mg) was used for separation under the following conditions: Apparatus: Agilent 1260/LH-Y-J0371(4-1); Chromatography column: CHIRALPAK AD-H (4.6 mm×250 mmL, 5 μm), No.: AD-H-44B; Mobile phase: n-hexane; Flow rate: 1.0 ml/min; Back pressure: 100 bar; Column temperature: 35° C.; Wavelength: 210 nm; Duration: 10 min.

Two optical isomers were obtained after separation: Peak 1 (retention time: 5.57 min, 300 mg, a light yellow liquid, ee %=99%), Peak 2 (retention time: 5.83 min, 270 mg, a light yellow liquid, ee %=99%).

Peak 1: MS m/z (ESI): 240.9 [M−1], 241.9[M+1].

$^1$H NMR (400 MHz, CDCl$_3$): δ 7.29 (dd, 1H, Ar—H), 7.25 (dd, 1H, Ar—H), 6.79 (t, 1H, Ar—H), 5.58 (s, 1H, OH), 2.48-2.40 (m, 1H, CH), 1.29 (d, 3H, CH$_3$), 1.07-0.98 (m, 1H, CH), 0.61-0.43 (m, 2H, CH$_2$), 0.26-0.16 (m, 2H, CH$_2$).

Peak 2: MS m/z (ESI): 240.9 [M−1], 241.9[M+1].

$^1$H NMR (400 MHz, CDCl$_3$): δ 7.29 (dd, 1H, Ar—H), 7.25 (dd, 1H, Ar—H), 6.79 (t, 1H, Ar—H), 5.58 (s, 1H, OH), 2.48-2.40 (m, 1H, CH), 1.29 (d, 3H, CH$_3$), 1.07-0.98 (m, 1H, CH), 0.61-0.43 (m, 2H, CH$_2$), 0.26-0.16 (m, 2H, CH$_2$).

Example 1

2-(1-cyclopropylethyl)-6-isopropylphenol
(Compound 1)

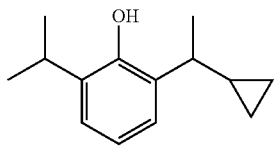

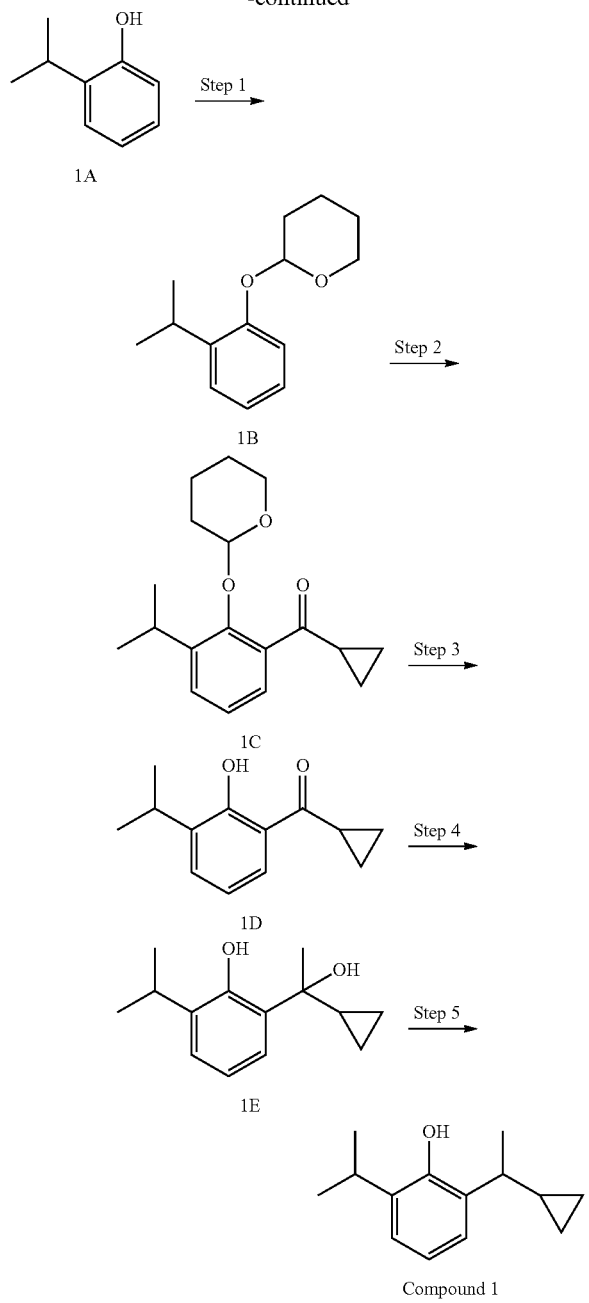

Step 1: 2-(2-isopropylphenoxy)tetrahydropyran (1B)

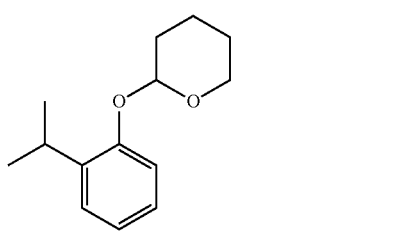 [SMILES: CC(C)c1ccccc1OC1CCCCO1]

2-isopropylphenol (1A) (10.00 g, 73.40 mmol), 3,4-2H-dihydropyran (18.60 g, 220.20 mmol) and dichloromethane (50 mL) were added to a reaction flask and mixed thoroughly, and then pyridinium p-toluenesulfonate (1.86 g, 7.40 mmol) was added thereto, following by stirring at room temperature for 20 h. Water (30 ml) was added thereto, and the reaction solution was extracted with dichloromethane (30 ml×3). The organic phases were combined, washed with saturated brine (30 ml×3), dried over anhydrous sodium sulfate, filtered, and the filtrate was concentrated under reduced pressure. The residue was purified by silica gel column chromatography (petroleum ether/ethyl acetate (v/v)=500:1) to give colorless liquid 2-(2-isopropylphenoxy)tetrahydropyran (1B) (13.4 g, yield: 82.71%, HPLC: 99.15%).

$^1$HNMR (400 MHz, CDCl$_3$): δ 7.25-7.20 (m, 1H), δ 7.15-7.09 (m, 2H), δ 6.97-6.93 (m, 1H), δ 5.44-5.42 (m, 1H), δ 3.94-3.88 (m, 1H), δ 3.65-3.62 (m, 1H), S 3.39-3.22 (m, 1H), S 1.90-1.86 (m, 1H), δ 1.73-1.67 (m, 2H), δ 1.60-1.54 (m, 3H), δ 1.25 (t, 6H).

Step 2: cyclopropyl-(3-isopropyl-2-tetrahydropyran-2-yloxy-phenyl)methanone (1C)

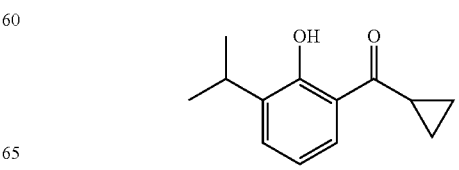

Under nitrogen protection, 2-(2-isopropylphenoxy)tetrahydropyran (1B) (10.00 g, 45.40 mmol) and dry tetrahydrofuran (30 mL) were added to a reaction flask and cooled to −20° C. with a dry-ice bath. 2.5 M n-butyllithium (20.00 mL, 50.00 mmol) was added, followed by warming-up to room temperature, stirring for 1 h, and cooling to −20° C. with a dry-ice bath. N-methoxy-N-methylcyclopropionamide (7.00 g, 54.20 mmol) was added, followed by warming-up to room temperature and stirring for 2 h.

The reaction was quenched by addition of saturated ammonium chloride (30 mL) and stirring for several minutes. The reaction mixture was extracted with ethyl acetate (30 mL×3) and washed with saturated brine (30 mL×3), dried over anhydrous sodium sulfate, filtered, and the filtrate was concentrated under reduced pressure, to obtain red liquid cyclopropyl-(3-isopropyl-2-tetrahydropyran-2-yloxy-phenyl)methanone (1C) (17.4 g, a crude product, HPLC: 68.00%) which was directly used for the next reaction step.

Step 3: cyclopropyl-(2-hydroxy-3-isopropyl-phenyl)methanone (1D)

(3-isopropyl-2-tetrahydropyran-2-yloxy-phenyl)methanone (1C) (17.4 g, the crude product) and methanol (50 ml) were added to a reaction flask, cooled to 0° C. in an ice bath. A 2M aqueous solution of hydrochloric acid (35 mL, 70.00 mmol) was added, following by warming-up to room temperature and stirring for half an hour. A saturated aqueous solution of sodium bicarbonate was added to adjust pH=6, and methanol was removed by rotary drying. The reaction mixture was extracted with ethyl acetate (50 mL×3) and washed with saturated brine (50 mL×3), dried over anhydrous sodium sulfate, filtered, and the filtrate was concentrated under reduced pressure. The residue was purified by silica gel column chromatography (petroleum ether/ethyl acetate (v/v)=300:1) to give colorless liquid cyclopropyl-(2-hydroxy-3-isopropyl-phenyl)methanone (1D) (7.23 g, yield over two steps: 78.26%, HPLC: 96.29%).

MS m/z(ESI): 205.1 (M−1).

$^1$HNMR (400 MHz, DMSO-d6): δ 12.98 (s, 1H), δ 8.08 (dd, 1H), δ 7.51 (dd, 1H), δ 6.98 (t, 1H), δ 3.34-3.26 (m, 1H), δ 3.04-3.01 (m, 1H), δ 2.52-2.50 (m, 1H), δ 1.19-1.12 (m, 11H).

Step 4: 2-(1-cyclopropyl-1-hydroxy-ethyl)-6-isopropyl-phenol (1E)

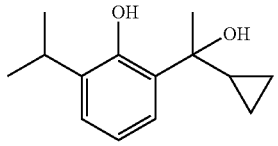 [SMILES: CC(C)c1cccc(C(C)(O)C2CC2)c1O]

Under nitrogen protection, cyclopropyl-(2-hydroxy-3-isopropyl-phenyl)methanone (1D) (10 g, 48.80 mmol) and dry toluene (50 mL) were added to a reaction flask and cooled to −30° C. with a dry-ice bath. A 3M solution of methylmagnesium bromide in n-hexane (49.00 mL, 146.30 mmol) was added, followed by warming-up to room temperature and stirring for 2 h. The reaction was quenched by addition of saturated ammonium chloride (100 mL). The reaction mixture was extracted with ethyl acetate (100 mL×3) and washed with saturated brine (100 mL×3), dried over anhydrous sodium sulfate, filtered, and the filtrate was concentrated under reduced pressure. The residue was purified by silica gel column chromatography (n-hexane/ethyl acetate (v/v)=50:1) to give light yellow liquid 2-(1-cyclopropyl-1-hydroxy-ethyl)-6-isopropyl-phenol (1E) (10.2 g, yield: 95.17%, HPLC: 97.96%).

MS m/z(ESI): 219.1 (M−1).

$^1$HNMR (400 MHz, CDCl$_3$): δ 7.32 (dd, 1H), δ 7.24 (dd, 1H), δ 7.13 (t, 1H), δ 4.64 (s, 1H), δ 3.43-3.36 (m, 1H), δ 1.56 (s, 3H), δ 1.37-1.31 (m, 1H), δ 1.27 (d, 6H), δ 0.54-0.39 (m, 4H).

Step 5: 2-(1-cyclopropylethyl)-6-isopropylphenol (Compound 1)

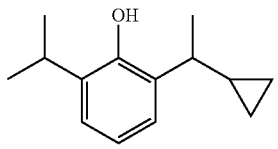

2-(1-cyclopropyl-1-hydroxy-ethyl)-6-isopropyl-phenol (1E) (3 g, 13.80 mmol), triethylsilane (6.42 g, 55.21 mmol) and dichloromethane (25 mL) were added to a reaction flask and cooled to −30° C. with a dry-ice bath. Trifluoroacetic acid (12.59 g, 110.40 mmol) was slowly added, and stirred for 2 h at a temperature controlled below 0° C. for reaction, and then the reaction was stopped. The reaction mixture was extracted with dichloromethane (100 mL×3) and washed with saturated brine (100 mL×3), dried over anhydrous sodium sulfate, filtered, and the filtrate was concentrated under reduced pressure. The residue was purified by silica gel column chromatography (petroleum ether/ethyl acetate (v/v)=100:1) to give colorless liquid 2-(1-cyclopropylethyl)-6-isopropylphenol (Compound 1) (2.02 g, yield: 71.63%, HPLC: 98.58%).

MS m/z(ESI): 203.1 (M−1).

$^1$HNMR (400 MHz, CDCl$_3$): δ 7.13 (dd, 1H), δ 7.08 (dd, 1H), δ 6.90 (t, 1H), δ 4.93 (s, 1H), δ 3.20-3.13 (m, 1H), δ 2.53-2.46 (m, 1H), δ 1.29 (d, 3H), δ 1.26 (d, 6H), δ 1.07-1.05 (m, 1H), δ 0.58-0.45 (m, 2H), δ 0.24-0.16 (m, 2H).

Example 2

2-sec-butyl-6-(1-cyclopropylethyl)phenol (Compound 2)

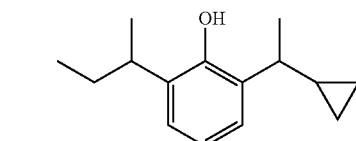

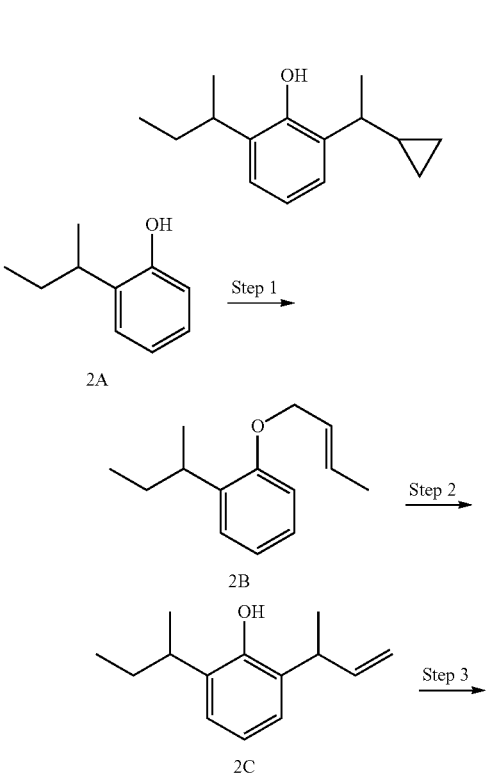

Compound 2

Step 1: 1-(but-2-enyloxy)-2-sec-butylbenzene (2B)

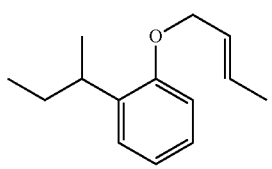

2-sec-butylphenol (2A) (20.00 g, 0.13 mol), dry diethyl ether (100 mL), crotonyl alcohol (14.42 g, 0.20 mol) and triphenyl phosphine (52.46 g, 0.20 mol) were sequentially added to a reaction flask, and diisopropyl azodicarboxylate (40.44 g, 0.20 mol) was added dropwise slowly while in an ice bath, followed by stirring at room temperature overnight. The reaction mixture was filtered and concentrated at reduced pressure. The residue was purified by silica gel column chromatography (n-hexane/ethyl acetate (v/v)=300:1) to give light yellow, oily 1-(but-2-enyloxy)-2-sec-butylbenzene (2B) (20.40 g, yield: 76.8%).

MS m/z (ESI): 205.1 [M+1].

$^1$H NMR (300 MHz, CDCl$_3$): δ7.16 (dd, 1H, Ar—H), 7.11 (dd, 1H, Ar—H), 6.94-6.90 (m, 1H, Ar—H), 6.84 (d, 1H, Ar—H), 5.90-5.69 (m, 3H, 2CH=), 4.44 (t, 2H, OCH$_2$), 3.15-3.00 (m, 1H, CH), 1.75 (dd, 3H, =CHCH$_3$), 1.68-1.50 (m, 2H, CH$_2$), 1.17 (d, 3H, CHCH$_3$), 0.85 (t, 3H, CH$_2$CH$_3$).

Step 2: 2-(but-3-en-2-yl)-6-sec-butylphenol (2C)

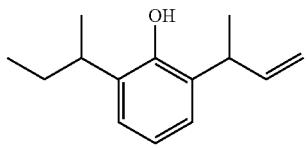

To the reaction flask, 1-(but-2-enyloxy)-2-sec-butylbenzene (2B) (10.00 g, 0.05 mol) was added, and heated at 200° C. to allow reaction for 4 h. The mixture was purified by silica gel column chromatography (n-hexane) to give light yellow, oily 2-(but-3-en-2-yl)-6-sec-butylphenol (2C) (1.74 g, 17.4%, HPLC: 96.50%).

MS m/z (ESI): 203.1 [M×1].

$^1$H NMR (400 MHz, CDCl$_3$): δ7.06 (dd, 1H, Ar—H), 6.99 (dd, 1H, Ar—H), 6.89 (t, 1H, Ar—H), 6.14-6.02 (m, 1H, CH=), 5.30-5.16 (m, 2H, =CH$_2$ and OH), 3.70-3.57 (m, 1H, CHCH=), 3.05-2.92 (m, 1H, CHCH$_2$), 1.72-1.50 (m, 2H, CH$_2$), 1.42 (d, 3H, CH$_3$), 1.22 (d, 3H, CH$_3$CH), 0.87 (t, 3H, CH$_2$CH$_3$).

Step 3: 2-sec-butyl-6-(1-cyclopropylethyl)phenol (Compound 2)

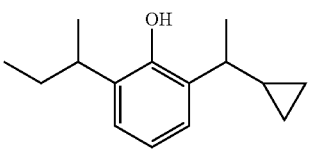 [SMILES: CCC(C)c1cccc(C(C)C2CC2)c1O]

Under nitrogen protection, dichloromethane (10 mL) was added to a reaction flask, and diethylzinc (1.21 g, 9.80 mmol) and trifluoroacetic acid (1.12 g, 9.80 mmol) were slowly added dropwise while in an ice bath, followed by stirring for 30 min. In an ice bath, diiodomethane (2.63 g, 9.80 mmol) was added, followed by stirring for 30 min, then 2-(but-3-en-2-yl)-6-sec-butylphenol (2C) (1.00 g, 4.90 mmol) was added, followed by stirring at room temperature for 4 h, and 1M hydrochloric acid (30 ml) was added to stop the reaction. The reaction mixture was extracted with dichloromethane (30 mL×2) and washed with saturated brine (30 mL×3). The organic phases were combined, dried over anhydrous sodium sulfate, filtered, and the filtrate was concentrated under reduced pressure. The residue was purified by silica gel column chromatography (n-hexane) to give light yellow oily 2-sec-butyl-6-(1-cyclopropylethyl)phenol (Compound 2) (0.60 g, yield: 56.6%, HPLC: 96.87%).

MS m/z (ESI): 217.1 [M+1].

$^1$H NMR (400 MHz, CDCl$_3$): δ7.14-7.08 (m, 1H, Ar—H), 7.02 (dd, 1H, Ar—H), 6.89 (t, 1H, Ar—H), 2.97-2.84 (m, 1H, CHCH$_2$), 2.57-2.44 (m, 1H, CH), 1.74-1.51 (m, 2H, CH$_2$), 1.30 (d, 3H, CH$_3$), 1.24 (d, 3H, CH$_3$), 1.10-1.00 (m, 1H, CH), 0.89 (t, 3H, CH$_3$), 0.62-0.40 (m, 2H, CH$_2$), 0.27-0.10 (m, 2H, CH$_2$).

Example 3

2-(1-cyclobutylethyl)-6-isopropylphenol (Compound 3)

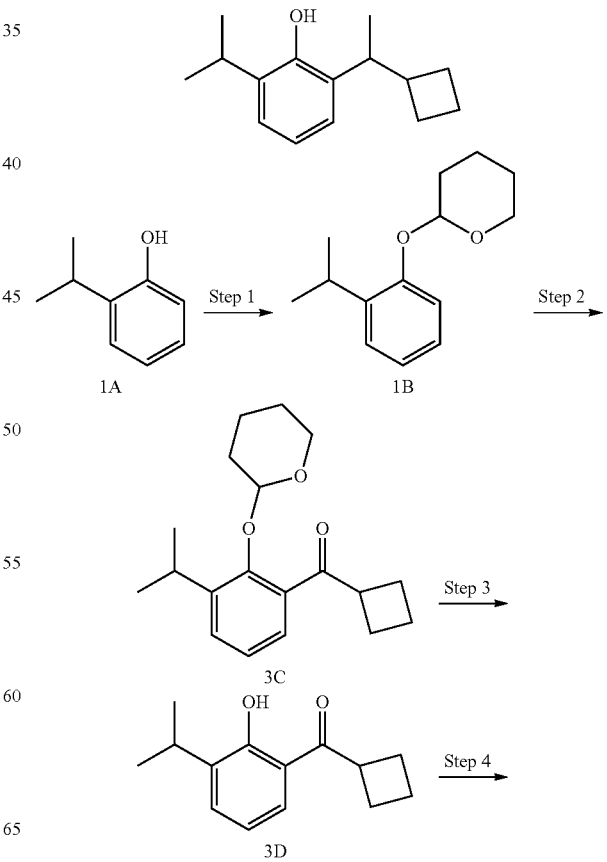

-continued

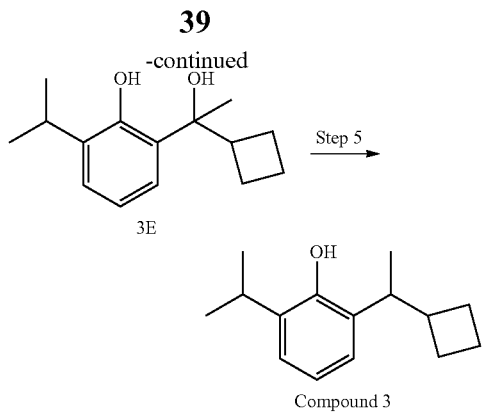

Step 5

Compound 3

Step 1: 2-(2-isopropylphenoxy)tetrahydropyran (1B)

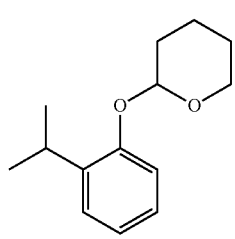 [SMILES: CC(C)c1ccccc1OC1CCCCO1]

2-isopropylphenol (1A) (1.5 Kg, 11.01 mol) and dichloromethane (6 L) were added to a reaction flask and mixed thoroughly, then pyridinium p-toluenesulfonate (276.78 g, 1.10 mol) was added thereto, then in an ice bath 3,4-2H-dihydropyran (1.39 Kg, 16.52 mol) was added dropwise, following by warming-up to room temperature and stirring overnight. The reaction solution was washed with water (2 L×3), with a sodium hydroxide solution (2 L×4), with water (2 L×2), and then with saturated brine (2 L×2), dried over anhydrous sodium sulfate, suction-filtered, and concentrated under reduced pressure, to obtain a crude product of 2-(2-isopropylphenoxy)tetrahydropyran (1B), which was directly used for the next reaction step.

Step 2: cyclobutyl(3-isopropyl-2-((tetrahydro-2H-pyran-2-yl)oxy)phenyl)methanone (3C)

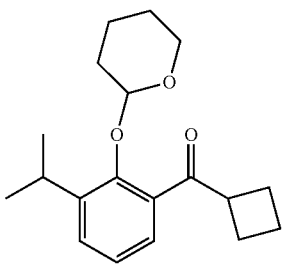 [SMILES: CC(C)c1cccc(C(=O)C2CCC2)c1OC1CCCCO1]

Under nitrogen protection, 2-(2-isopropylphenoxy)tetrahydropyran (1B) (33.00 g, the crude product) and tetrahydrofuran (150 mL) were added to a reaction flask, mixed thoroughly, and cooled to −35° C. with dry ice. N-butyllithium (72 mL, 2.5 M) was added dropwise slowly, followed by stirring at room temperature for 2 h. N-methoxy-N-methylcyclobutanecarboxamide (30.00 g, 210.00 mmol) was added slowly at −35° C., followed by stirring at room temperature for 4 h. In an ice bath, the reaction was quenched with a saturated solution of ammonium chloride. The reaction solution was extracted with ethyl acetate (150 mL×2) and washed with saturated brine (100 mL×2), dried over anhydrous sodium sulfate, filtered, and the filtrate was concentrated under reduced pressure, to obtain red oily liquid cyclobutyl(3-isopropyl-2-((tetrahydro-2H-pyran-2-yl)oxy)phenyl)methanone (3C) as a crude product, which was directly used for the next reaction step.

Step 3: cyclobutyl(2-hydroxy-3-isopropylphenyl)methanone (3D)

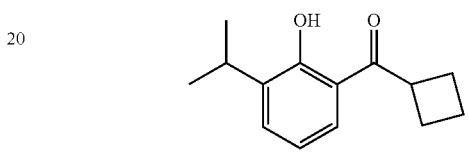

Cyclobutyl(3-isopropyl-2-((tetrahydro-2H-pyran-2-yl)oxy)phenyl)methanone (3C) (50.00 g, the crude product) was added to a reaction flask, and in an ice bath 1M hydrochloric acid solution in methanol (120 ml) was added thereto, followed by stirring for 30 min to allow the reaction to proceed. The reaction solution was adjusted to a pH between 6 and 7 with saturated sodium bicarbonate (50 ml), and concentrated under reduced pressure. The residual solution was extracted with ethyl acetate (120 mL×2) and washed with saturated brine (100 mL×2), dried over anhydrous sodium sulfate, filtered, and the filtrate was concentrated under reduced pressure. The residue was purified by silica gel column chromatography (petroleum ether) to give yellow oily cyclobutyl(2-hydroxy-3-isopropylphenyl)methanone (3D) (15.00 g, yield: 45.9%).

MS m/z (ESI): 217.1 [M−1].

1H NMR (300 MHz, CDCl$_3$): δ 12.84 (s, 1H), 7.45 (dd, 1H), 7.39 (dd, 1H), 6.83 (t, 1H), 4.09-4.00 (m, 1H), 3.42-3.36 (m, 1H), 2.51-2.42 (m, 2H), 2.34-2.26 (m, 2H), 2.15-2.03 (m, 1H), 1.96-1.87 (m, 1H), 1.24 (d, 6H).

Step 4: 2-(1-cyclobutyl-1-hydroxyethyl)-6-isopropylphenol (3E)

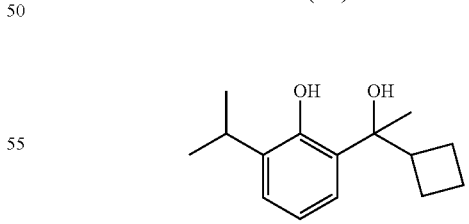

Under nitrogen protection, cyclobutyl(2-hydroxy-3-isopropylphenyl)methanone (3D) (12.00 g, 54.97 mmol) and tetrahydrofuran (36 mL) were added to a reaction flask, and while in an ice bath, methylmagnesium bromide (46 mL, 3M) was slowly added, followed by stirring at room temperature for 4 h. Then the reaction was quenched with a saturated solution of ammonium chloride (50 mL). The reaction solution was extracted with ethyl acetate (120 mL×2) and washed with saturated brine (100 mL×2), dried over anhydrous sodium sulfate, filtered, and the filtrate was concentrated under reduced pressure. The residue was purified by silica gel column chromatography (petroleum ether/ethyl acetate (v/v)=50:1) to give white solid 2-(1-cyclobutyl-1-hydroxyethyl)-6-isopropylphenol (3E) (11.20 g, yield: 86.8%).

MS m/z (ESI): 233.2 [M−1].

1H NMR (300 MHz, CDCl$_3$): δ 7.11 (dd, 1H), 6.84 (dd, 1H), 6.77 (t, 1H), 3.40-3.33 (m, 1H), 2.99-2.91 (m, 1H), 1.99-1.89 (m, 6H), 1.70-1.63 (m, 1H), 1.53 (s, 3H), 1.23 (d, 6H).

Step 5: 2-(1-cyclobutylethyl)-6-isopropylphenol (Compound 3)

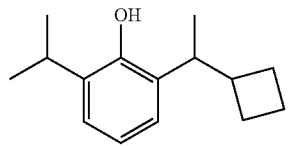 [SMILES: CC(C)c1cccc(C(C)C2CCC2)c1O]

2-(1-cyclobutyl-1-hydroxyethyl)-6-isopropylphenol (3E) (10.40 g, 44.40 mmol) and dichloromethane (100 mL) were added to a reaction flask and stirred until uniform. Triethylsilane (10.30 g, 88.80 mmol) was added, followed by stirring for 10 min. Upon cooling to −35° C. with dry ice, trifluoroacetic acid (40.50 g, 355.20 mmol) was added slowly, followed by stirring for 40 min to allow the reaction to proceed. Then the pH was adjusted to 7 with a saturated sodium bicarbonate solution. The organic layer was collected, tetrabutylammonium fluoride (11.60 g, 44.40 mmol) was added thereto, and the reaction was allowed to proceed at room temperature for 2 h. The reaction solution was washed with saturated brine, dried over anhydrous sodium sulfate, filtered, and the filtrate was concentrated under reduced pressure. The residue was purified by silica gel column chromatography (petroleum ether) to give light yellow liquid 2-(1-cyclobutylethyl)-6-isopropylphenol (Compound 3) (8.20 g, yield: 84.5%, HPLC: 98%).

MS m/z (ESI): 217.2 [M−1].

1H NMR (300 MHz, CDCl$_3$): δ 7.03 (dd, 1H), 6.94 (dd, 1H), 6.86 (t, 1H), 4.74 (s, 1H), 3.18-3.11 (m, 1H), 2.97-2.89 (m, 1H), 2.57-2.52 (m, 1H), 2.16-2.13 (m, 1H), 1.82-1.75 (m, 4H), 1.70-1.49 (m, 1H), 1.26 (d, 6H), 1.14 (d, 3H).

Example 4

2,6-bis(1-cyclopropylethyl)phenol (Compound 4)

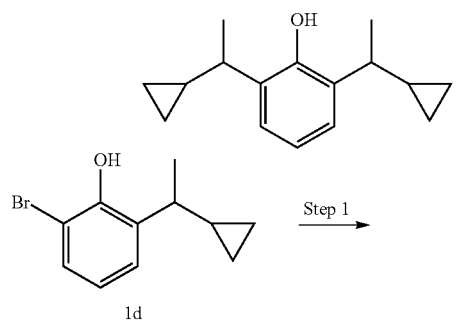

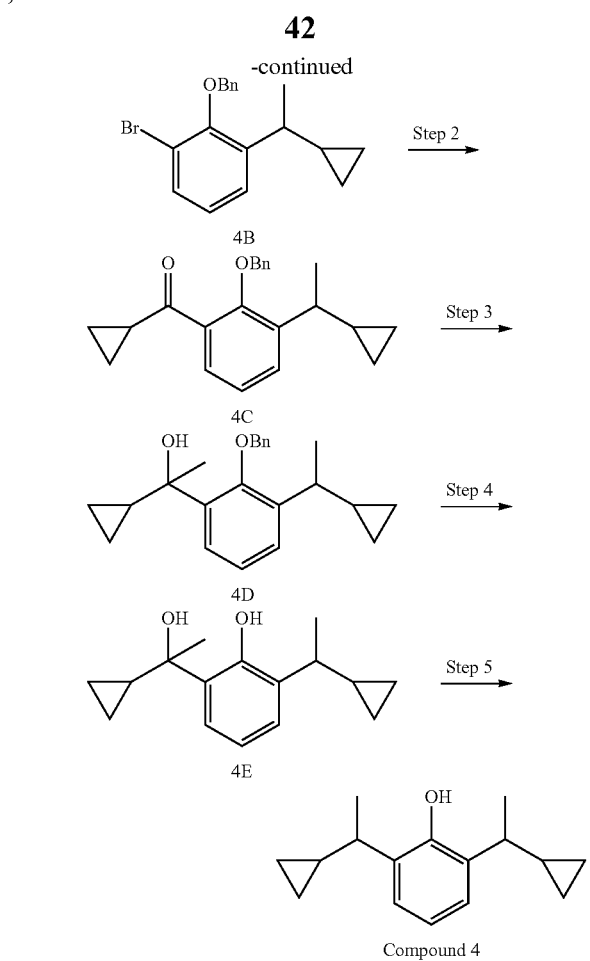

Step 1:
2-benzyloxy-1-bromo-3-(1-cyclopropylethyl)benzene (4B)

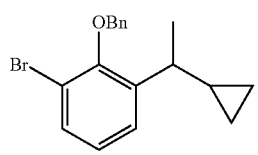 [SMILES: CC(c1cccc(Br)c1OCc1ccccc1)C1CC1]

2-bromo-6-(1-cyclopropylethyl)phenol (1d) (100 g, 414.72 mmol) and acetone (500 mL) were added to a reaction flask and stirred until uniform. Then potassium carbonate (57.32 g, 414.72 mmol) and benzyl bromide (57.75 g, 456.20 mmol) were added successively. The reaction mixture was heated to reflux for 12 h, filtered, and the filtrate was concentrated under reduced pressure. The residue was purified by silica gel column chromatography (petroleum ether/ethyl acetate (v/v)=100:1) to give yellow oily 2-benzyloxy-1-bromo-3-(1-cyclopropylethyl)benzene (4B) as a crude product (128 g, yield: 92.2%), which was directly used for the next reaction step.

$^1$H NMR (400 MHz, CDCl$_3$): δ7.44-7.34 (m, 7H) 7.03-6.99 (t, 1H), 4.95-4.85 (m, 2H), 2.49-2.41 (m, 1H), 1.24 (d, 3H), 0.95-0.90 (m, 1H), 0.54-0.51 (m, 1H), 0.35-0.32 (m, 1H), 0.17-0.07 (m, 2H).

Step 2: [2-benzyloxy-3-(1-cyclopropylethyl)phenyl]-cyclopropyl-methanone (4C)

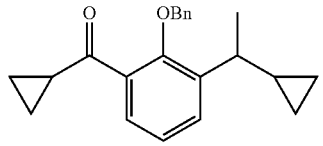 [SMILES: CC(c1cccc(C(=O)C2CC2)c1OCc1ccccc1)C1CC1]

Under nitrogen protection, the crude product of 2-benzyloxy-1-bromo-3-(1-cyclopropylethyl)benzene (4B) (128 g, 386.42 mmol) and tetrahydrofuran (500 mL) were added to a reaction flask, the temperature was controlled at −78° C. in a dry ice-acetone bath. N-butyllithium (37.13 g, 579.63 mmol) was slowly added dropwise, followed by stirring for 1 h at −78° C. N-methoxy-N-methyl cyclopropanecarboxamide (74.86 g, 579.63 mmol, from Asta Tech) was added, followed by reaction under stirring for 4 h at −78° C. The reaction was quenched with a saturated ammonium chloride solution (20 mL). The reaction mixture was extracted with ethyl acetate (500 mL×4), and the organic phases were combined, washed with saturated brine (200 mL×2), dried over anhydrous sodium sulfate, filtered, and the filtrate was concentrated under reduced pressure, to give yellow oily [2-benzyloxy-3-(1-cyclopropylethyl)phenyl]-cyclopropyl-methanone (4C) as a crude product (144 g), which was directly used for the next reaction step.

Step 3: 1-[2-benzyloxy-3-(1-cyclopropylethyl)phenyl]-1-cyclopropyl-ethanol (4D)

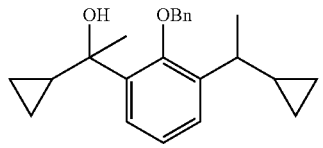 [SMILES: CC(c1cccc(C(C)(O)C2CC2)c1OCc1ccccc1)C1CC1]

Under nitrogen protection, the crude product of [2-benzyloxy-3-(1-cyclopropylethyl)phenyl]-cyclopropyl-methanone (4C) (144 g, 449.4 mmol) and tetrahydrofuran (500 mL) were added to a reaction flask. In an ice bath, methylmagnesium bromide (69.66 g, 584.22 mmol) was added dropwise, then the temperature was allowed to spontaneously rise to room temperature, at which the reaction was allowed to proceed for 3 h. The reaction was quenched with a saturated ammonium chloride solution (20 mL). The reaction mixture was extracted with ethyl acetate (500 mL×3), and the organic phases were combined, washed with saturated brine (100 mL×3), dried over anhydrous sodium sulfate, filtered, and the filtrate was concentrated under reduced pressure, The residue was purified by silica gel column chromatography (petroleum ether/ethyl acetate (v/v)=10:1) to give yellow oily 1-[2-benzyloxy-3-(1-cyclopropylethyl)phenyl]-1-cyclopropyl-ethanol (4D) (80 g, yield: 57%, HPLC: 95.7%).

$^1$H NMR (400 MHz, CDCl$_3$): δ 7.43-7.13 (m, 8H), 4.99-4.89 (m, 2H), 4.6 (d, 1H), 2.53-2.49 (m, 1H), 1.59-1.56 (m, 3H), 1.36-1.24 (m. 3H), 0.95-0.96 (m, 1H), 0.35-0.18 (m, 8H).

Step 4: 2-(1-cyclopropylethyl)-6-(1-cyclopropyl-1-hydroxy-ethyl)phenol (4E)

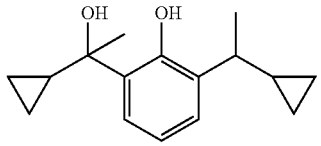 [SMILES: CC(c1cccc(C(C)(O)C2CC2)c1O)C1CC1]

1-[2-benzyloxy-3-(1-cyclopropylethyl)phenyl]-1-cyclopropyl-ethanol (4D) (80 g, 237 mmol), ethanol (200 mL), and Pd/C (4 g, 10% Pd (w/w)) were added to a reaction flask. The flask was purged with nitrogen three times, and with hydrogen three times. The reaction mixture was heated to 50° C. to allow reaction to proceed for 12 h, filtered, and the filtrate was concentrated under reduced pressure. The residue was purified by silica gel column chromatography (petroleum ether/ethyl acetate (v/v)=50:1) to give colorless oily 2-(1-cyclopropylethyl)-6-(1-cyclopropyl-1-hydroxyethyl)phenol (4E) (3.6 g, yield: 71.43%, HPLC: 97.8%).

MS m/z (ESI): 245 [M−1].

$^1$H NMR (400 MHz, d$^6$-DMSO): δ 10.24 (d, 1H), 7.15-7.12 (m, 1H), 7.02-7.00 (dd, 1H), 6.72 (t, 1H), 6.50 (d, 1H), 2.43-2.27 (m, 1H), 1.46 (s, 3H), 1.28-1.19 (m, 1H), 1.19 (d, 3H), 1.03-1.01 (m. 1H), 0.37-0.05 (m, 8H).

Step 5: 2,6-bis(1-cyclopropylethyl)phenol (Compound 4)

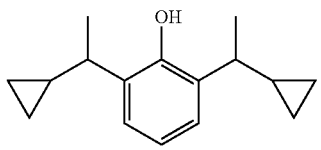 [SMILES: CC(c1cccc(C(C)C2CC2)c1O)C1CC1]

2-(1-cyclopropylethyl)-6-(1-cyclopropyl-1-hydroxyethyl)phenol (4E) (120 g, 407.12 mmol) and dichloromethane (500 mL) were added to a reaction flask, and triethylsilane (113.28 g, 974.24 mmol) was added dropwise at 0° C., followed by stirring for 15 min. Trifluoroacetic acid (222.17 g, 1.95 mol) was added dropwise in batches in an ice-water bath. After the dropwise addition, the reaction was allowed to warm up to room temperature and stirred for 2 h. Water (500 mL) was added, followed by stirring for 5 minutes. The mixture was allowed to settle and partition. The organic phase was collected, washed with a saturated sodium bicarbonate solution (500 mL×3). The organic phase was collected and transferred to a reaction flask, to which tetrabutylammonium fluoride (127.16 g, 487.12 mmol) was added, followed by stirring for 12 h at room temperature. Water (300 mL) was added, and the mixture was allowed to settle and partition. The organic phase was washed with water (100 mL×3) and with saturated brine (100 mL×2), dried over anhydrous sodium sulfate, filtered, and the filtrate was concentrated under reduced pressure. The residue was purified by silica gel column chromatography (n-hexane) to give light yellow oily 2,6-bis(1-cyclopropylethyl)phenol (Compound 4) (70 g, yield: 62.5%, HPLC: 96.78%).

$^1$H NMR (400 MHz, CDCl$_3$): δ 7.15 (t, 2H), 6.91 (t, 1H), 4.85 (s, 1H), 2.54-2.19 (m, 2H), 1.31 (d, 6H), 1.08-1.04 (m, 2H), 0.53-0.43 (m. 4H), 0.21-0.17 (m, 4H).

Example 5

2-[(1R)-1-cyclobutylethyl]-6-isopropyl-phenol (Compound 5)

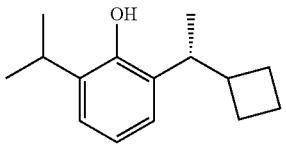 [SMILES: CC(C)c1cccc([C@H](C)C2CCC2)c1O]

Example 6

2-[(1S)-1-cyclobutylethyl]-6-isopropyl-phenol (Compound 6)

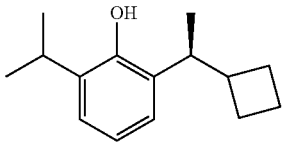 [SMILES: CC(C)c1cccc([C@@H](C)C2CCC2)c1O]

2-(1-cyclobutylethyl)-6-isopropylphenol (Compound 3) (800 mg) was used for separation under the following conditions: Apparatus: Agilent 1260/LH-Y-J0371(4-1); Chromatography: CHIRALPAK AD-H (4.6 mm×250 mmL, 5 μm), No.: AD-H-44B; Mobile phase: n-hexane; Flow rate: 1.0 ml/min; Back pressure: 100 bar; Column temperature: 35° C.; Wavelength: 210 nm; Duration: 10 min. Two optical isomers were obtained after separation: Peak 1 (retention time: 12.93 s, 340 mg, a light yellow liquid, ee %=99%), Peak 2 (retention time: 15.55 s, 360 mg, a light yellow liquid, ee %=99%).

Peak 1: MS m/z (ESI): 217.1 [M−1].

$^1$H NMR (400 MHz, CDCl$_3$): δ 7.05 (dd, 1H), 6.96 (dd, 1H), 6.88 (t, 1H), 4.78 (s, 1H), 3.22-3.12 (m, 1H), 2.99-2.92 (m, 1H), 2.63-2.53 (m, 1H), 2.19-2.13 (m, 1H), 1.93-1.73 (m, 4H), 1.65-1.56 (m, 1H), 1.28 (d, 6H), 1.16 (d, 3H).

Peak 2: MS m/z (ESI): 217.1 [M−1].

$^1$HNMR (400 MHz, CDCl3): δ 7.05 (dd, 1H), δ 6.96 (dd, 1H), 6.88 (t, 1H), 4.75 (s, 1H), 3.20-3.12 (m, 1H), 2.99-2.91 (m, 1H), 2.59-2.57 (m, 1H), 2.17-2.16 (m, 1H), 1.88-1.81 (m, 4H), 1.65-1.56 (m, 1H), 1.28 (d, 6H), 1.16 (d, 3H).

Example 7

2-[(1R)-1-cyclopropylethyl]-6-isopropyl-phenol (Compound 7)

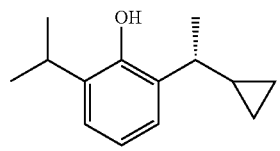

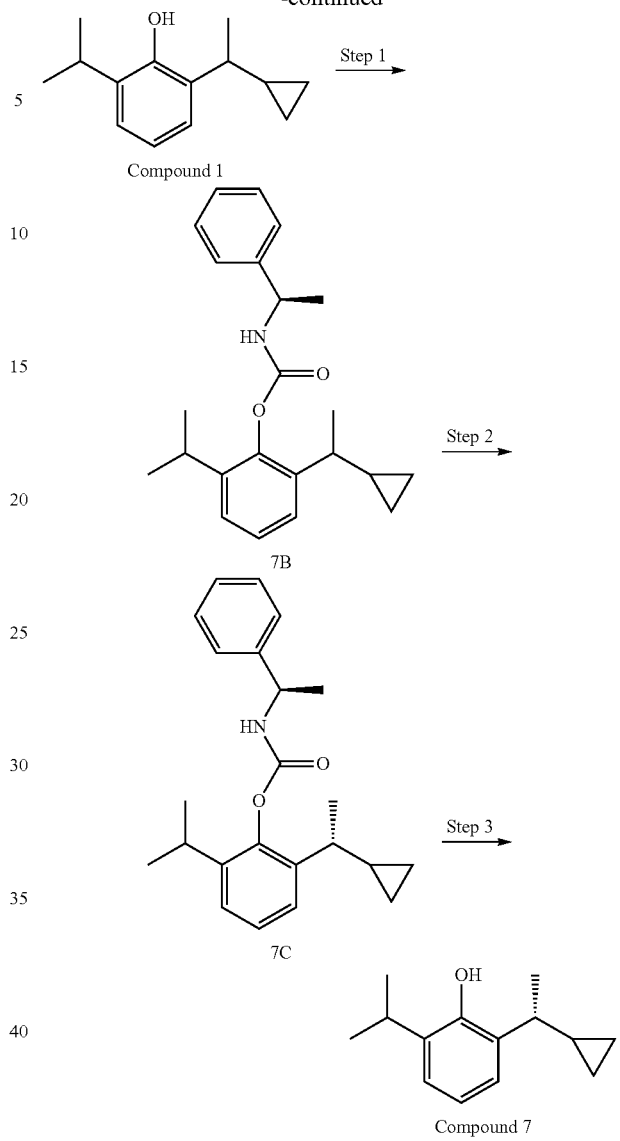

Step 1: [2-[(1-cyclopropylethyl)]-6-isopropyl-phenyl] N-[(1R)-1-phenylethyl] Carbamate (7B)

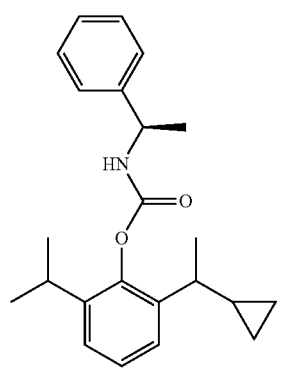 [SMILES: CC(C)c1cccc(C(C)C2CC2)c1OC(=O)N[C@H](C)c1ccccc1]

2-(1-cyclopropylethyl)-6-isopropylphenol (Compound 1) (150 g, 0.71 mol) and tetrahydrofuran (750 ml) were added to a reaction flask, triethylamine (208 g, 2.06 mol) was added dropwise, followed by thorough stirring, then (1R)-1-phenethylisocyanate (162 g, 1.10 mol) was added, the mixture was heated to 63° C. and stirred overnight, and then the reaction was stopped. The reaction solution was cooled to room temperature, and the filtrate was concentrated under reduced pressure. The residue was dissolved in ethyl acetate (260 ml) and filtered. The filtrate was concentrated under reduced pressure to give the white solid target product [2-[(1-cyclopropylethyl)]-6-isopropyl-phenyl] N-[(1R)-1-phenylethyl] carbamate (7B) (270.00 g).

MS m/z (ESI): 352.5[M+1].

¹HNMR (400 MHz, CDCl₃): δ 7.37~7.11 (m, 8H), 5.27~5.06 (m, 1H), 4.94~4.87 (m, 1H), 3.00~2.98 (m, 1H), 2.11~2.07 (m, 1H), 1.55 (d, 3H), 1.23~1.13 (m, 9H), 0.90~0.98 (m, 1H), 0.44~0.44 (m, 1H), 0.26~0.36 (m, 1H), 0.01~0.12 (m, 2H).

Step 2: [2-[(1R)-1-cyclopropylethyl]-6-isopropyl-phenyl]N-[(1R)-1-phenylethyl]carbamate (7C)

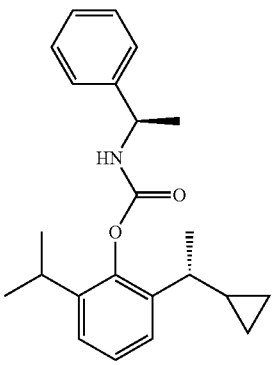 [SMILES: CC(C)c1cccc([C@H](C)C2CC2)c1OC(=O)N[C@H](C)c1ccccc1]

[2-[(1-cyclopropylethyl)]-6-isopropyl-phenyl] N-[(1R)-1-phenylethyl] carbamate (7B) (270 g, the crude product) was re-crystallized 5 times in n-hexane, and filtered to give the white powdery target product [2-[(1R)-1-cyclopropyl-ethyl]-6-isopropyl-phenyl]N-[(1R)-1-phenylethyl]carbamate (7C) (60 g, yield: 23.26%, chiral-HPLC: 99.7%).

¹H NMR (400 MHz, CDCl₃) δ 7.46-7.08 (m, 8H), 5.28 (d, 1H), 4.90 (m, 1H), 3.12-2.87 (m, 1H), 2.06 (d, 1H), 1.55 (d, 3H), 1.32-0.88 (m, 10H), 0.49 (s, 1H), 0.31 (s, 1H), 0.18-0.03 (m, 2H).

Step 3: 2-[(1R)-1-cyclopropylethyl]-6-isopropyl-phenol

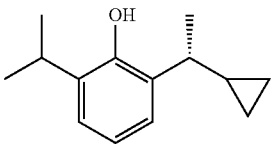

[2-[(1R)-1-cyclopropylethyl]-6-isopropyl-phenyl]N-[(1R)-1-phenylethyl]carbamate (7C) (60 g, 170.71 mmol) was dissolved in tetrahydrofuran (600 ml), and a 1M solution of sodium hydroxide (290 mL, 290 mmol) was added thereto. Under nitrogen protection, the mixture was heated to 70° C. to carry out 4-h reaction, and then allowed to settle and partition. The organic layer was collected, and the aqueous layer was adjusted to pH=7 with 1 M hydrochloric acid. The reaction mixture was extracted with ethyl acetate (250 mL×3), and the organic phases were combined, washed with saturated brine (300 mL×2), dried over anhydrous sodium sulfate, filtered, and the filtrate was concentrated under reduced pressure. The residue was purified by silica gel column chromatography (petroleum ether/ethyl acetate (v/v)=100:1) to give the light yellow liquid target product 2-[(1R)-1-cyclopropylethyl]-6-isopropyl-phenol (Compound 7) (32.3 g, yield: 92.29%, HPLC: 98.43%, chiral-HPLC: 99.79%).

MS m/z (ESI): 203.1 [M−1].

¹HNMR (400 MHz, CDCl₃): δ 7.14 (dd, 1H), 7.08 (dd, 1H), 6.91 (t, 1H), 4.93 (s, 1H), 3.22~3.14 (m, 1H), 2.55~2.48 (m, 1H), 1.33 (d, 6H), 1.28 (d, 3H), 1.10~1.05 (m, 1H), 0.60~0.58 (m, 1H), 0.49~0.46 (m, 1H), 0.25~0.18 (m, 2H).

Example 8

2-[(1S)-1-cyclopropylethyl]-6-isopropyl-phenol (Compound 8)

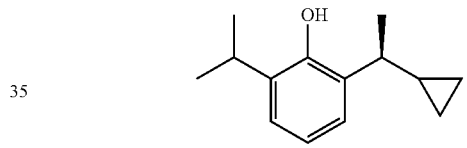

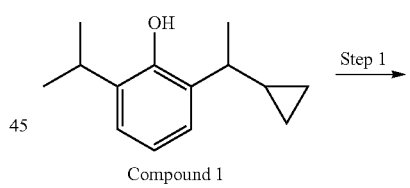

Compound 1

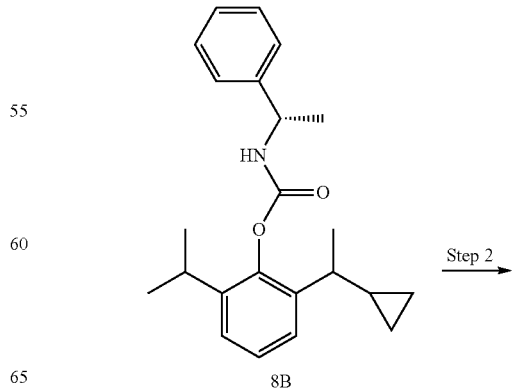

8B

Step 2: [2-[(1S)-1-cyclopropylethyl]-6-isopropyl-phenyl] N-[(1S)-1-phenylethyl]carbamate (8C)

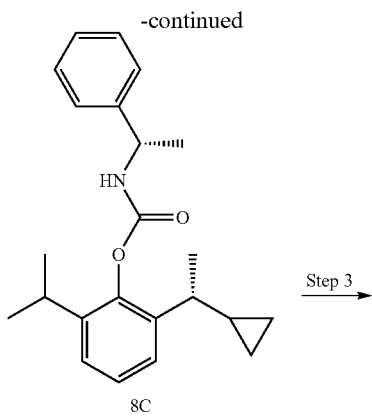

8C

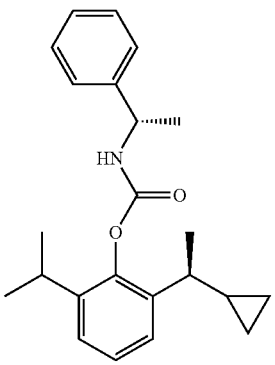

The [2-[1-cyclopropylethyl)]-6-isopropyl-phenyl] N-[(1S)-1-phenylethyl]carbamate (8B) (80.00 g) obtained in the above step was re-crystallized 4 times in n-hexane and filtered, and the filter cake was oven-dried to give the white powdery target product [2-[(1S)-1-cyclopropylethyl]-6-isopropyl-phenyl] N-[(1S)-1-phenylethyl]carbamate (8C) (39 g, yield: 54.93%, HPLC: 97.62%, chiral-HPLC: 99.84%).

Compound 1 is a raceme having only one chiral center, and can only be separated into two isomers, i.e. Compounds 7 and 8. Compound 8C have two chiral centers, one of which is introduced by (S)-(−)-1-phenethylisocyanate, and the chiral carbon atom to which cyclopropyl is attached has the same chirality as Compound 8 and therefore has a S configuration.

Step 3: 2-[(1S)-1-cyclopropylethyl]-6-isopropyl-phenol (Compound 8)

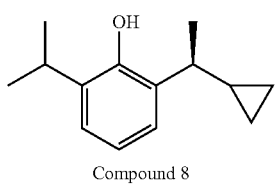

Compound 8

Step 1: [2-[1-cyclopropylethyl)]-6-isopropyl-phenyl] N-[(1S)-1-phenylethyl]carbamate (8B)

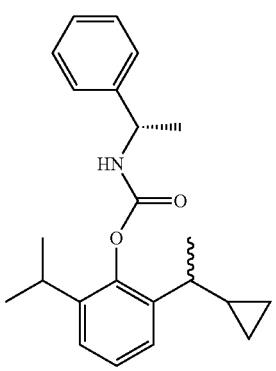 [SMILES: CC(C)c1cccc(C(C)C2CC2)c1OC(=O)N[C@@H](C)c1ccccc1]

2-(1-cyclopropylethyl)-6-isopropylphenol (Compound 1) (42.00 g, 205.57 mmol) and tetrahydrofuran (200 ml) were added to a reaction flask, triethylamine (58.00 g, 573.18 mmol) was added dropwise, followed by thorough stirring, then (S)-(−)-1-phenethylisocyanate (45.00 g, 308.36 mmol) was added, the mixture was heated to 63° C. and stirred for 6 h. The reaction solution was concentrated under reduced pressure, dissolved in ethyl acetate (200 ml), and suction-filtered under reduced pressure. The filtrate was concentrated under reduced pressure to give the white solid target product [2-[1-cyclopropylethyl)]-6-isopropyl-phenyl] N-[(1S)-1-phenylethyl]carbamate (8B) (80.00 g).

MS m/z (ESI): 352.5[M+1].

$^1$HNMR (400 MHz, CDCl$_3$): δ 7.38~7.11 (m, 8H), 5.27~5.08 (m, 1H), 4.94~4.87 (m, 1H), 3.00~2.97 (m, 1H), 2.08 (s, 1H), 1.55 (d, 3H), 1.23~1.13 (m, 9H), 0.95 (s, 1H), 0.49 (s, 1H), 0.31 (s, 1H), 0.05 (s, 1H).

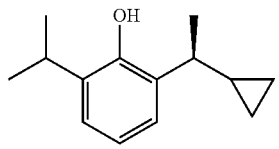

[2-[(1S)-1-cyclopropylethyl]-6-isopropyl-phenyl] N-[(1S)-1-phenylethyl]carbamate (8C) (39.00 g, 110.96 mmol) was dissolved in tetrahydrofuran (390 ml), and a 1.0 M aqueous solution of sodium hydroxide (190 mL, 190 mmol) was added thereto. Under nitrogen protection, the mixture was heated to 70° C. to carry out 4-h reaction, and then allowed to settle and partition. The organic layer was collected, and the aqueous layer was adjusted to pH=7 with 1 M hydrochloric acid. The reaction mixture was extracted with ethyl acetate (250 mL×3), and the organic phases were combined, washed with saturated brine, dried over anhydrous sodium sulfate, filtered, and the filtrate was concentrated under reduced pressure. The residue was purified by silica gel column chromatography (petroleum ether/ethyl acetate (v/v)=100:1) to give the light yellow liquid target product 2-[(1S)-1-cyclopropylethyl]-6-isopropyl-phenol (Compound 8) (17.2 g, yield: 75.80%, HPLC: 97.67%, chiral-HPLC: 99.86%). Compound 1 is a raceme having only one chiral center, and can only be separated into two isomers, i.e. Compounds 7 and 8.

MS m/z (ESI): 203.1 [M−1].

¹HNMR (400 MHz, CDCl₃): δ 7.14 (dd, 1H), 7.08 (dd, 1H), 6.93 (t, 1H), 4.93 (s, 1H), 3.22~3.15 (m, 1H), 2.55~2.48 (m, 1H), 1.32 (d, 6H), 1.28 (d, 3H), 1.10~1.04 (m, 1H), 0.60~0.58 (m, 1H), 0.49~0.46 (m, 1H), 0.25~0.18 (m, 2H).

Example 9

2-[(1S)-1-cyclopropylethyl]-6-[(1R)-1-cyclopropylethyl]phenol (Compound 9)

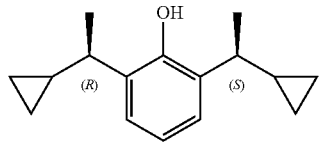

Example 10

2,6-bis[(1R)-1-cyclopropylethyl]phenol (Compound 10)

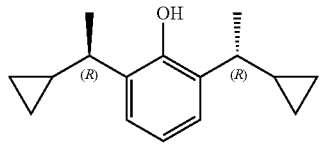

Example 11

2,6-bis[(1S)-1-cyclopropylethyl]phenol (Compound 11)

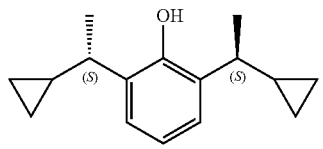

Preparation of Examples 9 to 11: 2,6-bis(1-cyclopropylethyl)phenol (Compound 4) (4.8 g, 14.2 mmol) was separated by chiral HPLC with a preparing apparatus and a chiral column (conditions: Chiral column CHIRALPAK OZ-H. Mobile phase: n-hexane/isopropanol (v/v)=100:0, flow rate 1.0 mL/min, UV=214 nm, column temperature: 35° C.). Three fractions were collected at 15.7 min, 16.8 min and 21.3 min respectively, and concentrated under reduced pressure to give Peak 1 (white solid, 710 mg, yield: 59.1%, HPLC: 96.89%, Chrial-HPLC: 97.92%), Peak 2 (yellow oil, 1.3 g, yield: 54.16%, HPLC: 97.50%, Chrial-HPLC: 99.33%), Peak 3 (white solid, 720 mg, yield: 60%, HPLC: 95.55%, Chrial-HPLC: 98.48%).

Peak 1: MS m/z (ESI): 229.2 [M−1].
1HNMR: (400 MHz, CDCl₃): δ 7.13 (d, 2H), 6.90 (t, 1H), 5.06 (s, 1H), 2.52-2.48 (m, 2H), 1.29 (d, 6H), 1.06-1.02 (m, 2H), 0.55-0.42 (m. 4H), 0.22-0.16 (m, 4H).

Peak 2: MS m/z (ESI): 229 [M−1].
1H NMR (400 MHz, CDCl₃): δ 7.13 (d, 2H), 6.89 (t, 1H), 5.04 (s, 1H), 2.54-2.47 (m, 2H), 1.30 (d, 6H), 1.06-1.03 (m, 2H), 0.53-0.42 (m. 4H), 0.20-0.15 (m, 4H).

Peak 3: MS m/z (ESI): 229.2 [M−1].
1HNMR: (400 MHz, CDCl₃): δ 7.13 (d, 2H), 6.89 (t, 1H), 5.05 (s, 1H), 2.53-2.46 (m, 2H), 1.29 (d, 6H), 1.05-1.01 (m, 2H), 0.56-0.42 (m. 4H), 0.20-0.14 (m, 4H).

Example 12

2-[(1R)-1-cyclopropylethyl]-6-sec-butyl-phenol (Compound 12)

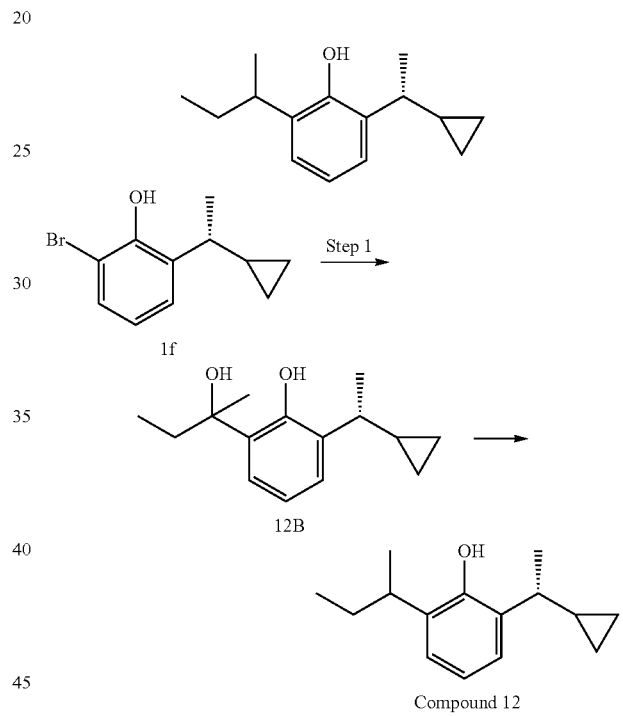

Step 1: 2-[(1R)-1-cyclopropylethyl]-6-(1-hydroxy-1-methyl-propyl)phenol (12B)

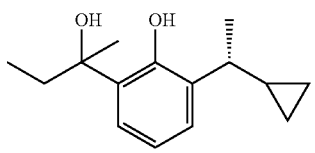 [SMILES: CCC(C)(O)c1cccc([C@H](C)C2CC2)c1O]

2-bromo-6-((1R)-1-cyclopropylethyl)phenol (1f) (10.0 g, 0.04 mol) was dissolved in dry tetrahydrofuran (50 mL). Under nitrogen protection, a 50 ml n-butyllithium solution (2.5 M in n-hexane, 0.12 mol) was added dropwise at 0° C. or lower, followed by reaction for 40 min at 0° C. or lower. Butanone (4.5 g, 0.06 mol) was added dropwise, followed by reaction for 30 min at −10° C. The mixture was then allowed to warm up to room temperature and stirred overnight. The reaction was quenched with water (20 mL) added slowly at 0-5° C., and allowed to settle and partition. The aqueous phase was extracted with ethyl acetate (40 mL×2), and the organic phases were combined, washed with saturated brine (50 mL×1), dried over anhydrous sodium sulfate for 10 min, and concentrated under reduced pressure. The residue was purified by silica gel column chromatography (eluant: petroleum ether/ethyl acetate (v/v)=100:1 to 50:1) to give light yellow oily 2-[(1R)-1-cyclopropylethyl]-6-(1-hydroxy-1-methyl-propyl)phenol (12B) (6.8 g, yield: 70%).

Step 2: 2-[(1R)-1-cyclopropylethyl]-6-sec-butyl-phenol (Compound 12)

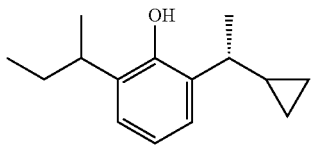 [SMILES: CCC(C)c1cccc([C@H](C)C2CC2)c1O]

2-[(1R)-1-cyclopropylethyl]-6-(1-hydroxy-1-methyl-propyl)phenol (12B) (6.0 g, 0.026 mol) was dissolved in dichloromethane (30 mL). Under nitrogen protection, triethylsilane (6.0 g, 0.05 mol) was added thereto. After cooling to −30° C. or lower, trifluoroacetic acid (11.7 g, 0.1 mol) was added dropwise. After the dropwise addition, the reaction was allowed to proceed for 3 h at 5° C. or lower. The reaction was quenched with water (30 mL), and allowed to settle and partition. The aqueous phase was extracted with dichloromethane (30 mL×2), and the organic phases were combined, to which tetrabutylammonium fluoride trihydrate (4 g, 0.013 mol) was added, followed by stirring at room temperature for 30 min. Then water (20 mL) was added, followed by stirring for 3 minutes, and the mixture was allowed to settle and partition. The aqueous phase was extracted with dichloromethane (20 mL×3), and the organic phases were combined, washed with saturated brine (30 mL×1), dried over anhydrous sodium sulfate for 10 min, and concentrated under reduced pressure. The residue was purified by silica gel column chromatography (eluant: petroleum ether/ethyl acetate (v/v)=100:1 to 50:1) to give light yellow liquid 2-[(1R)-1-cyclopropylethyl]-6-sec-butyl-phenol (Compound 12) (2.8 g, yield: 50%; HPLC: 97.43%).

1H NMR (400 MHz, CDCl3): δ 7.11 (dt, 1H), 7.01 (dd, 1H), 6.88 (t, 1H), 4.88 (br, 1H), 2.91-2.89 (m, 1H), 2.52-2.50 (m, 1H), 1.67-1.57 (m, 2H), 1.30 (d, 3H), 1.24 (d, 3H), 1.06-1.04 (m, 1H), 0.89 (t, 3H), 0.58-0.53 (m, 1H), 0.48-0.44 (m, 1H), 0.21-0.17 (m, 2H).

MS m/z (ESI): 217.3 [M−1].

Example 13

2-[(1R)-1-cyclopropylethyl]-6-[(1 S)-1-methylpropyl]phenol (Compound 13)

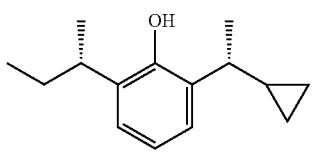 [SMILES: CC[C@H](C)c1cccc([C@H](C)C2CC2)c1O]

Example 14

2-[(1R)-1-cyclopropylethyl]-6-[(1R)-1-methylpropyl]phenol (Compound 14)

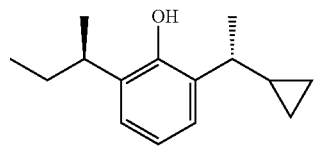 [SMILES: CC[C@@H](C)c1cccc([C@H](C)C2CC2)c1O]

Preparation of Examples 13 and 14:
2-[(1R)-1-cyclopropylethyl]-6-sec-butyl-phenol (Compound 12) (1 g) was used for separation under the following conditions: Apparatus: Gilson GX-281/CH-Y-C0630; Chromatography column: CHIRALPAK OJ-H (4.6 mm×150 mmL, 5 μm); Mobile phase: n-hexane:isopropanol (v:v=100:0); Flow rate: 1 ml/min; Back pressure: 100 bar; Column temperature: 35° C.; Wavelength: 210 nm; Duration: 8 min. Two optical isomers were obtained after separation: Peak 1 (0.35 g, retention time: 4.977 min, a light yellow oily substance, ee %=99%), Peak 2 (0.32 g, retention time: 5.820 min, 270 mg, a light yellow oily substance, ee %=98%).

Example 15

2-[(1S)-1-cyclopropylethyl]-6-sec-butyl-phenol (Compound 15)

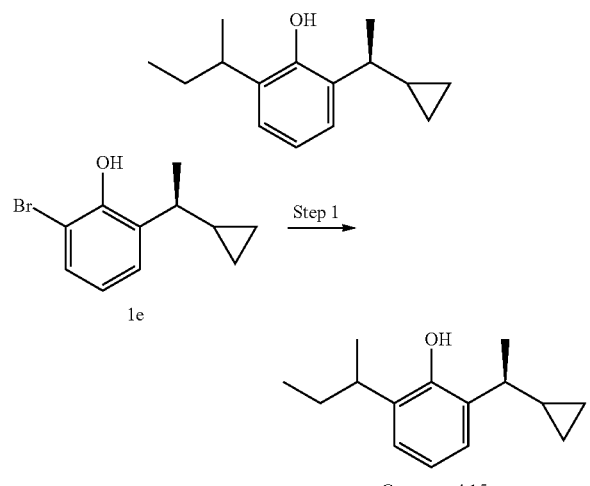

Compound 15

Compound 1e (30.0 g, 0.12 mol) was dissolved in dry tetrahydrofuran (300 mL). Under nitrogen protection, a 150 ml n-butyllithium solution (2.5 M in n-hexane, 0.36 mol) was added dropwise at 0° C. or lower, followed by reaction for 40 min at 0° C. or lower. Butanone (55.7 ml, 0.7 mol) was added dropwise, followed by reaction for 30 min at −10° C. The mixture was then allowed to warm up to room temperature and stirred overnight. The reaction was quenched with water added slowly at 0-5° C., and allowed to settle and partition. The aqueous phase was extracted with ethyl acetate (100 mL×2), and the organic phases were combined, washed with saturated brine (50 mL×1), dried over anhydrous sodium sulfate for 10 min, and concentrated under reduced pressure. The residue was purified by silica gel column chromatography (eluant: petroleum ether/ethyl acetate=100:1 to 50:1) to give a crude product (35.5 g).

33.0 g of the above crude product was dissolved, without further purification, in 165 ml dichloromethane. Under nitrogen protection, triethylsilane (32.75 g, 0.24 mol) was added thereto. After cooling to −30° C. or lower, trifluoroacetic acid (64.23 g, 0.48 mol) was added dropwise. After the addition, the reaction was allowed to proceed for 3 h at 5° C. or lower. The reaction was quenched with water (200 mL), and allowed to settle and partition into layers. The aqueous phase was extracted with dichloromethane (100 mL×2), and the organic phases were combined, to which tetrabutylammonium fluoride trihydrate (100 g, 0.28 mol) was added, followed by stirring at room temperature for 30 minutes. Then water (500 mL) was added, followed by stirring for 3 min, and the mixture was allowed to settle and partition. The aqueous phase was extracted with dichloromethane (100 mL×3), and the organic phases were combined, washed with saturated brine (200 mL×1), dried over anhydrous sodium sulfate for 10 min, and concentrated under reduced pressure. The residue was purified by silica gel column chromatography (eluant: petroleum ether/ethyl acetate (v/v)=100:1 to 50:1) to give light yellow liquid 2-[(1 S)-1-cyclopropylethyl]-6-sec-butyl-phenol (Compound 15) (10.1 g, total yield over two steps: 37%).

¹H NMR (400 MHz, CDCl₃) δ 7.09-7.12 (m, 1H), 7.00-7.02 (m, 1H), 6.89 (t, 1H), 4.88 (s, 1H), 2.87-2.93 (m, 1H), 2.46-2.56 (m, 1H), 1.55-1.69 (m, 2H), 1.29 (d, 3H), 1.24 (d, 3H), 1.02-1.08 (m, 1H), 0.89 (t, 3H), 0.53-0.58 (m, 1H), 0.43-0.49 (m, 1H), 0.16-0.23 (m, 2H).

MS m/z (ESI): 217.3 [M−1].

Example 16

2-[(1S)-1-cyclopropylethyl]-6-[(1S)-1-methylpropyl]phenol (Compound 16)

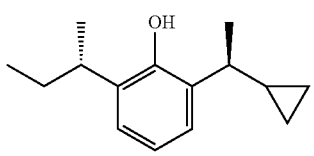 [SMILES: CC[C@H](C)c1cccc([C@@H](C)C2CC2)c1O]

Example 17

2-[(1S)-1-cyclopropylethyl]-6-[(1R)-1-methylpropyl]phenol (Compound 17)

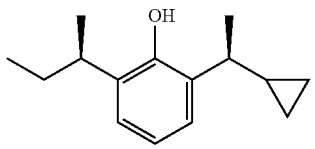 [SMILES: CC[C@@H](C)c1cccc([C@@H](C)C2CC2)c1O]

Preparation of Examples 16 and 17:

2-[(1S)-1-cyclopropylethyl]-6-sec-butyl-phenol (Compound 15) (500 mg) was used for separation under the following conditions: Apparatus: Agilent 1260/LH-Y-J0371 (4-1); Chromatography column: CHIRALPAK OJ-HS (0.46 cm I.D.×15 cm L), No: AD-H-44B; Mobile phase: n-hexane:isopropanol (v:v=100:1); Flow rate: 1.0 ml/min; Back pressure: 100 bar; Column temperature: 35° C.; Wavelength: 214 nm; Duration: 10 min. Two optical isomers were obtained after separation: Peak 1 (retention time: 3.61 min, 190 mg, a light yellow liquid, ee %=99%), Peak 2 (retention time: 4.21 min, 200 mg, a light yellow liquid, ee %=99%).

Peak 1: ¹H NMR (400 MHz, CDCl₃) δ 7.09-7.12 (m, 1H), 7.00-7.02 (m, 1H), 6.89 (t, 1H), 4.88 (s, 1H), 2.87-2.93 (m, 1H), 2.46-2.56 (m, 1H), 1.55-1.69 (m, 2H), 1.29 (d, 3H), 1.24 (d, 3H), 1.02-1.08 (m, 1H), 0.89 (t, 3H), 0.53-0.58 (m, 1H), 0.43-0.49 (m, 1H), 0.16-0.23 (m, 2H).

MS m/z (ESI): 217.3 [M−1].

Peak 2: ¹H NMR (400 MHz, CDCl₃) δ 7.09-7.12 (m, 1H), 7.00-7.02 (m, 1H), 6.89 (t, 1H), 4.88 (s, 1H), 2.87-2.93 (m, 1H), 2.46-2.56 (m, 1H), 1.55-1.69 (m, 2H), 1.29 (d, 3H), 1.24 (d, 3H), 1.02-1.08 (m, 1H), 0.89 (t, 3H), 0.53-0.58 (m, 1H), 0.43-0.49 (m, 1H), 0.16-0.23 (m, 2H).

MS m/z (ESI): 217.3 [M−1].

Example 18

[[2-[(1R)-1-cyclopropylethyl]-6-isopropyl-phenoxy]methyl-sodiooxy-phosphoryl]oxy sodium (Compound 18)

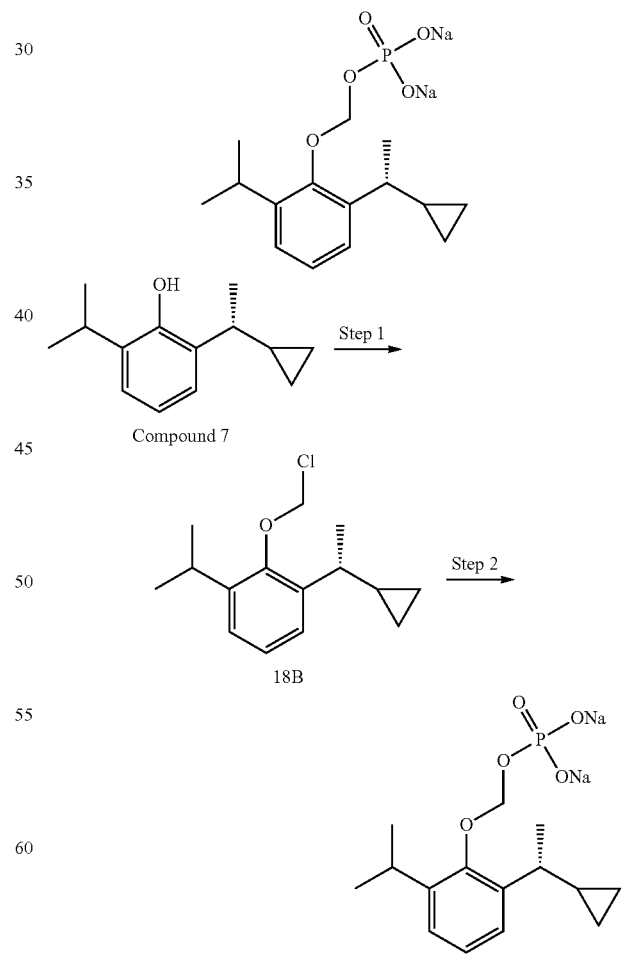

Step 1: 2-(chloromethoxy)-1-[(1R)-1-cyclopropyl-ethyl]-3-isopropyl-benzene (18B)

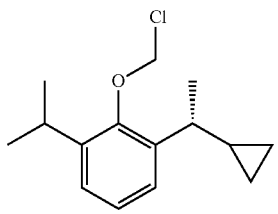 [SMILES: CC(C)c1cccc([C@H](C)C2CC2)c1OCCl]

2-[(1R)-1-cyclopropylethyl]-6-isopropyl-phenol (Compound 7) (20.0 g, 0.098 mol), tetrahydrofuran (100 mL) and sodium hydroxide (7.84 g, 0.196 mol) were added to a reaction flask, and heated to reflux for 30 min. Then bromochloromethane (380 g, 2.94 mol) was added thereto, followed by reaction at 70° C. for 2 h, and then the stirring was stopped. The reaction solution was suction-filtered, and the filtrate was concentrated under reduced pressure. The residue was purified by silica gel column chromatography (petroleum ether) to give colorless liquid 2-(chloromethoxy)-1-[(1R)-1-cyclopropylethyl]-3-isopropyl-benzene (18B) as a crude product, which was directly used for the next reaction step.

$^1$H NMR (300 MHz, CDCl$_3$): δ 7.26-7.24 (m, 1H), 7.21-7.14 (m, 2H), 5.70 (s, 2H), 3.34-3.28 (m, 1H), 2.59-2.52 (m, 1H), 1.28 (d, 3H), 1.23 (dd, 6H), 0.95-0.93 (m, 1H), 0.56-0.54 (m, 1H), 0.35-0.33 (m, 1H), 0.24-0.15 (m, 2H).

Step 2: [[2-[(1R)-1-cyclopropylethyl]-6-isopropyl-phenoxy]methyl-sodiooxy-phosphoryl]oxy sodium (Compound 18)

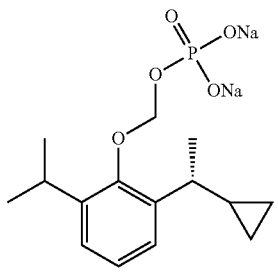

Phosphoric acid (62.7 g, 0.64 mol), triethylamine (80.9 g, 0.80 mol) and acetonitrile (400 mL) were added to a reaction flask, heated to 65° C., and stirred for 30 min. Then 2-(chloromethoxy)-1-[(1R)-1-cyclopropylethyl]-3-isopropyl-benzene (18B) (20.0 g, 0.08 mol) was added. The mixture was heated to 75° C., stirred for 3 h, concentrated under reduced pressure, then dissolved in water (200 mL), and adjusted to pH=1 with a 10% hydrochloric acid solution. The mixture was extracted with tert-butyl methyl ether (200 mL×3), and washed with saturated brine (100 mL×1). The organic phases were combined and concentrated under reduced pressure. Water (100 mL) was added to the residue, and the pH was adjusted to about 10~11 with a sodium hydroxide solution (NaOH: w/w=20%). The resultant was washed with tert-butyl methyl ether (100 mL×3) until the organic layer was colorless. Isopropanol (300 mL) was added to the residue, and the mixture was concentrated under reduced pressure to obtain a residue, which was made into a slurry with acetonitrile (70 mL) while heated to 50° C., and the hot slurry was suction-filtered to give white solid [[2-[(1R)-1-cyclopropylethyl]-6-isopropyl-phenoxy] methyl-sodiooxy-phosphoryl]oxy sodium (Compound 18) (20.0 g, yield: 70%, HPLC: 97.6%).

$^1$H NMR (400 MHz, D$_2$O): δ 7.41-7.38 (m, 1H), 7.31-7.26 (m, 2H), 5.23-5.17 (m, 2H), 3.47-3.44 (m, 1H), 2.63-2.59 (m, 1H), 1.30 (d, 3H), 1.22 (dd, 6H), 1.04-1.01 (m, 1H), 0.57-0.53 (m, 1H), 0.34-0.29 (m, 2H), 0.14-0.12 (m, 1H).

MS m/z (ESI): 313.2 [M−46+1].

Example 19

Verification of the Absolute Configuration of Compound 7

1. Single-Crystal X-Ray Diffraction Assay of [2-[(1R)-1-cyclopropylethyl]-6-isopropyl-phenyl] N-[(1R)-1-phenylethyl]carbamate (7C)

[2-[(1R)-1-cyclopropylethyl]-6-isopropyl-phenyl]N-[(1R)-1-phenylethyl]carbamate (7C) was dissolved in methanol, the mixture was clarified upon heating and allowed to settle for several days to precipitate single crystals, which were suction-filtered, washed, and dried for the single-crystal assay.

Colorless single-crystal flakes of 0.30 mm×0.20 mm×0.20 mm in size were selected and adhered to a glass mesh. The crystal for diffraction was triclinic system, the space group is P1, and the lattice parameters are: a=5.3665(3), b=10.3493(11), c=18.750(2) Å, α=97.598(9)°, β=96.660(7)°, γ=90.165(6)°, the unit cell volume V=1025.11(17) Å$^3$, and the asymmetric cell number Z=2. The diffraction intensity data were collected in an Xcalibur four-circle single-crystal diffractometer at 293.15K with a MoKα ray (λ=0.7107, Ray tube voltage: 50 kv, Tube current: 40 ma), with a distance D between the crystal and the CCD detector=45 mm and a scanning mode of 2θ (6.32°<θ<52.744°). 8385 diffraction points in total were collected (−6≤h≤6, −12≤k≤12, −21≤l≤23), including 5645 independent diffraction points [Rint=0.0372, Rsigma=0.0588]. Collection and retrieval of the crystal diffraction intensity data were performed with the software CrysAlisPro equipped with the diffractometer. The resolving of crystal structure was performed by Olex2 and SHEIXS-13 (the direct method), and the coordinates of all atoms and anisotropic parameters were refined by SHEIXL-13 (the partial least square method). For the final crystal structure data, Residual factor R$_1$=0.0850, wR$_2$=0.2088 [I>=2σ(I)], R$_1$=0.1115, wR$_2$=0.2405 [all data], S=1.064, with 480 refined parameters and 3 constraint conditions.

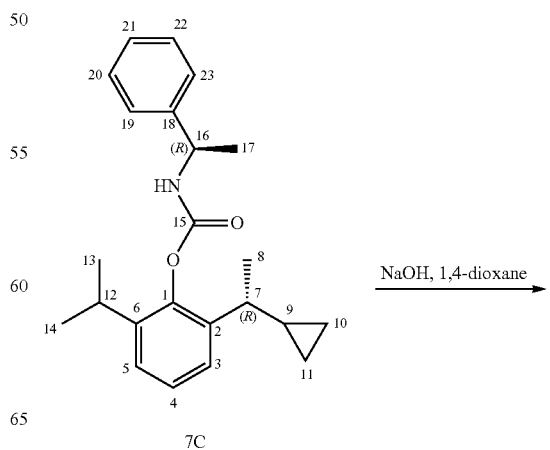

7C

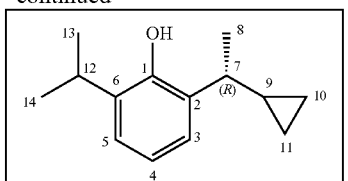

Compound 7

The carbon atom No. 16 of Compound 7C has its absolute configuration introduced by the known (R)-(+)-1-phenethylisocyanate, and therefore its absolute configuration is the known R configuration. The single-crystal X-ray diffraction pattern (FIG. 1) shows that the absolute configuration of C-7 is the same as C-16, and thus is also the R configuration. It is confirmed by the absolute configuration of Compound 7C that the absolute configuration of C-7 Compound 7 is the R configuration.

2. Chirality Retention Assay

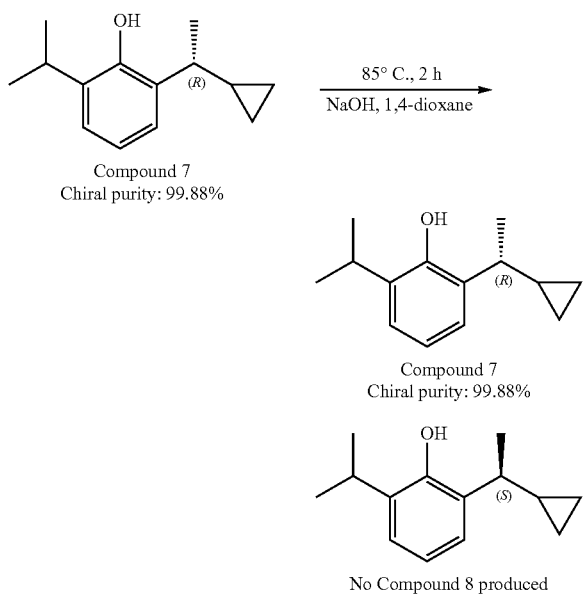

Compound 7C needs to undergo alkaline hydrolysis to produce Compound 7. A chirality retention assay was performed and confirmed that during the alkaline hydrolysis Compound 7C had not undergone absolute configuration transition at C-7.

Assay Procedure:

Compound 7 having a chiral purity of 99.88%, an aqueous solution of sodium hydroxide, and 1,4-dioxane were heated at 85° C. for 2 hours (this is a more drastic condition than that of hydrolysis of Compound 7C). Then the chiral purity was measured again, and confirmed that the chiral purity of Compound 7 was still 99.88%, the same as before the assay. The result demonstrates that the absolute configuration of C-7 in Compound 7C is the same as that of C-7 in the final product Compound 7.

Example 20

Prescription

| | |
|---|---|
| Compound 7 | 5 g |
| Soybean oil | 50 g |
| Medium-chain triglyceride | 50 g |
| Egg-yolk lecithin | 12 g |
| Glycerol | 22.5 g |
| Sodium oleate | 0.3 g |
| Sodium hydroxide | appropriate amount |
| Water for injection, added up to | 1000 ml |

Under nitrogen protection, soybean oil for injection (from AVIC (Tieling) Pharmaceutical Co. Ltd.) and medium chain triglyceride (from AVIC (Tieling) Pharmaceutical Co. Ltd.) were mixed and heated to about 50° C., Egg-yolk lecithin (from Lipoid GmbH, Germany) and Compound 7 were added thereto under high-speed stirring until uniform, and the temperature was controlled at 55° C. to 60° C. to obtain an oil phase; glycerol for injection (from Hunan ER-KANG Pharmaceutical Co. Ltd.) and sodium oleate were added to an appropriate amount of water for injection and mixed, the pH of the aqueous phase was adjusted to 10.0, and the temperature was controlled at 55° C. to 60° C. to obtain an aqueous phase. Under high-speed stirring (with a high-shear mixing emulsifying machine, from IKA), the oil phase was added to the aqueous phase to make an initial emulsion, which was continuously homogenized with a high pressure homogenizer (GEA Niro) until the emulsion particles met the requirements under examination. Then the emulsion was filtered, sealed in a container under nitrogen, sterilized in a steam autoclave, and cooled. After passing the test, an emulsion for injection of Compound 7 was obtained.

Example 21

Prescription

| | |
|---|---|
| Compound 7 | 10 g |
| Soybean oil | 100 g |
| Egg-yolk lecithin | 12 g |
| Glycerol | 22.5 g |
| Sodium oleate | 0.3 g |
| Sodium hydroxide | appropriate amount |
| Water for injection, added up to | 1000 ml |

Under nitrogen protection, soybean oil for injection (from AVIC (Tieling) Pharmaceutical Co. Ltd.) was heated to about 50° C., refined Egg-yolk lecithin (from Lipoid GmbH, Germany) and Compound 7 were added thereto under high-speed stirring until uniform, and the temperature was controlled at 60° C. to 65° C. to obtain an oil phase; glycerol for injection (from Hunan ER-KANG Pharmaceutical Co. Ltd.) and sodium oleate were added to an appropriate amount of water for injection and mixed, the pH of the aqueous phase was adjusted to 9.5, and the temperature was controlled at 60° C. to 65° C. to obtain an aqueous phase. Under high-speed stirring (with a high-shear mixing emulsifying machine, from IKA), the oil phase was added to the aqueous phase to make an initial emulsion, which was continuously homogenized with a high pressure homogenizer until the emulsion particles met the requirements under examination. Then the emulsion was filtered, sealed in a container under nitrogen, sterilized in a steam autoclave, and cooled. After passing the test, an emulsion for injection of Compound 7 was obtained.

Example 22

Prescription

| Compound 7 | 10 g |
|---|---|
| Soybean oil | 50 g |
| Medium-chain triglyceride | 50 g |
| Egg-yolk lecithin | 12 g |
| Glycerol | 22.5 g |
| Oleic acid | 0.3 g |
| Sodium hydroxide | appropriate amount |
| Water for injection, added up to | 1000 ml |

Under nitrogen protection, soybean oil for injection (from AVIC (Tieling) Pharmaceutical Co. Ltd.) and medium chain triglyceride (from AVIC (Tieling) Pharmaceutical Co. Ltd.) were mixed and heated to about 50° C., Egg-yolk lecithin (from Lipoid GmbH, Germany), Compound 7, and oleic acid were added thereto under high-speed stirring until uniform, and the temperature was controlled at 65° C. to 70° C. to obtain an oil phase; glycerol for injection (from Hunan ER-KANG Pharmaceutical Co. Ltd.) was added to an appropriate amount of water for injection and mixed, the pH of the aqueous phase was adjusted to 10.5, and the temperature was controlled at 65° C. to 70° C. to obtain an aqueous phase. Under high-speed stirring (with a high-shear mixing emulsifying machine, from IKA), the oil phase was added to the aqueous phase to make an initial emulsion, which was continuously homogenized with a high pressure homogenizer (GEA Niro) until the emulsion particles met the requirements under examination. Then the emulsion was filtered, sealed in a container under nitrogen, sterilized in a steam autoclave, and cooled. After passing the test, an emulsion for injection of Compound 7 was obtained.

Example 23

Prescription

| Compound 7 | 2 g |
|---|---|
| Soybean oil | 50 g |
| Medium-chain triglyceride | 50 g |
| Egg-yolk lecithin | 12 g |
| Glycerol | 22.5 g |
| Sodium hydroxide | appropriate amount |
| Water for injection, added up to | 1000 ml |

Under nitrogen protection, soybean oil for injection (from AVIC (Tieling) Pharmaceutical Co. Ltd.) and medium chain triglyceride (from AVIC (Tieling) Pharmaceutical Co. Ltd.) were mixed and heated to about 50° C., Egg-yolk lecithin (from Lipoid GmbH, Germany) and Compound 7 were added thereto under high-speed stirring until uniform, and the temperature was controlled at 70° C. to 75° C. to obtain an oil phase; glycerol for injection (from Hunan ER-KANG Pharmaceutical Co. Ltd.) was added to an appropriate amount of water for injection and mixed, the pH of the aqueous phase was adjusted to 11.0, and the temperature was controlled at 70° C. to 75° C. to obtain an aqueous phase. Under high-speed stirring (with a high-shear mixing emulsifying machine, from IKA), the oil phase was added to the aqueous phase to make an initial emulsion, which was continuously homogenized with a high pressure homogenizer (GEA Niro) until the emulsion particles met the requirements under examination. Then the emulsion was filtered, sealed in a container under nitrogen, sterilized in a steam autoclave, and cooled. After passing the test, an emulsion for injection of Compound 7 was obtained.

Example 24

Prescription

| Compound 7 | 5 g |
|---|---|
| Soybean oil | 50 g |
| Medium-chain triglyceride | 50 g |
| Egg-yolk lecithin | 6 g |
| Glycerol | 22.5 g |
| Sodium oleate | 0.3 g |
| Sodium hydroxide | appropriate amount |
| Water for injection, added up to | 1000 ml |

Under nitrogen protection, soybean oil for injection (from AVIC (Tieling) Pharmaceutical Co. Ltd.) and medium chain triglyceride (from AVIC (Tieling) Pharmaceutical Co. Ltd.) were mixed and heated to about 50° C., Egg-yolk lecithin (from Lipoid GmbH, Germany) and Compound 7 were added thereto under high-speed stirring until uniform, and the temperature was controlled at 70° C. to 75° C. to obtain an oil phase; glycerol for injection (from Hunan ER-KANG Pharmaceutical Co. Ltd.) and sodium oleate were added to an appropriate amount of water for injection and mixed, the pH of the aqueous phase was adjusted to 10.0, and the temperature was controlled at 70° C. to 75° C. to obtain an aqueous phase. Under high-speed stirring (with a high-shear mixing emulsifying machine, from IKA), the oil phase was added to the aqueous phase to make an initial emulsion, which was continuously homogenized with a high pressure homogenizer (GEA Niro) until the emulsion particles met the requirements under examination. Then the emulsion was filtered, sealed in a container under nitrogen, sterilized in a steam autoclave, and cooled. After passing the test, an emulsion for injection of Compound 7 was obtained.

Example 25

Prescription

| Compound 7 | 20 g |
|---|---|
| Soybean oil | 100 g |
| Medium-chain triglyceride | 100 g |
| Egg-yolk lecithin | 12 g |
| Glycerol | 22.5 g |
| Sodium oleate | 0.3 g |
| Sodium hydroxide | appropriate amount |
| Water for injection, added up to | 1000 ml |

Under nitrogen protection, soybean oil for injection (from AVIC (Tieling) Pharmaceutical Co. Ltd.) and medium chain triglyceride (from AVIC (Tieling) Pharmaceutical Co. Ltd.) were mixed and heated to about 50° C., Egg-yolk lecithin (from Lipoid GmbH, Germany) and Compound 7 were added thereto under high-speed stirring until uniform, and the temperature was controlled at 55° C. to 60° C. to obtain an oil phase; glycerol for injection (from Hunan ER-KANG Pharmaceutical Co. Ltd.) and sodium oleate were added to an appropriate amount of water for injection and mixed, the pH of the aqueous phase was adjusted to 10.5, and the temperature was controlled at 55° C. to 60° C. to obtain an aqueous phase. Under high-speed stirring (with a high-shear mixing emulsifying machine, from IKA), the oil phase was added to the aqueous phase to make an initial emulsion, which was continuously homogenized with a high pressure homogenizer (GEA Niro) until the emulsion particles met the requirements under examination. Then the emulsion was filtered, sealed in a container under nitrogen, sterilized in a steam autoclave, and cooled. After passing the test, an emulsion for injection of Compound 7 was obtained.

Example 26

Prescription

| Compound 7 | 30 g |
|---|---|
| Soybean oil | 150 g |
| Medium-chain triglyceride | 150 g |
| Egg-yolk lecithin | 12 g |
| Glycerol | 25 g |
| Sodium oleate | 0.3 g |
| Sodium hydroxide | appropriate amount |
| Water for injection, added up to | 1000 ml |

Under nitrogen protection, soybean oil for injection (from AVIC (Tieling) Pharmaceutical Co. Ltd.) and medium chain triglyceride (from AVIC (Tieling) Pharmaceutical Co. Ltd.) were mixed and heated to about 50° C., Egg-yolk lecithin (from Lipoid GmbH, Germany) and Compound 7 were added thereto under high-speed stirring until uniform, and the temperature was controlled at 55° C. to 60° C. to obtain an oil phase; glycerol for injection (from Hunan ER-KANG Pharmaceutical Co. Ltd.) and sodium oleate were added to an appropriate amount of water for injection and mixed, the pH of the aqueous phase was adjusted to 11.0, and the temperature was controlled at 55° C. to 60° C. to obtain an aqueous phase. Under high-speed stirring (with a high-shear mixing emulsifying machine, from IKA), the oil phase was added to the aqueous phase to make an initial emulsion, which was continuously homogenized with a high pressure homogenizer (GEA Niro) until the emulsion particles met the requirements under examination. Then the emulsion was filtered, sealed in a container under nitrogen, sterilized in a steam autoclave, and cooled. After passing the test, an emulsion for injection of Compound 7 was obtained.

Example 27

Prescription

| Compound 7 | 10 g |
|---|---|
| Soybean oil | 50 g |
| Medium-chain triglyceride | 50 g |
| Egg-yolk lecithin | 12 g |
| Glycerol | 22.5 g |
| Oleic acid | 0.6 g |
| Sodium hydroxide | appropriate amount |
| Water for injection, added up to | 1000 ml |

Under nitrogen protection, soybean oil for injection (from AVIC (Tieling) Pharmaceutical Co. Ltd.) and medium chain triglyceride (from AVIC (Tieling) Pharmaceutical Co. Ltd.) were mixed and heated to about 50° C., Egg-yolk lecithin (from Lipoid GmbH, Germany), Compound 7, and oleic acid were added thereto under high-speed stirring until uniform, and the temperature was controlled at 60° C. to 65° C. to obtain an oil phase; glycerol for injection (from Hunan ER-KANG Pharmaceutical Co. Ltd.) was added to an appropriate amount of water for injection and mixed, the pH of the aqueous phase was adjusted to 11.0, and the temperature was controlled at 60° C. to 65° C. to obtain an aqueous phase. Under high-speed stirring (with a high-shear mixing emulsifying machine, from IKA), the oil phase was added to the aqueous phase to make an initial emulsion, which was continuously homogenized with a high pressure homogenizer (GEA Niro) until the emulsion particles met the requirements under examination. Then the emulsion was filtered, sealed in a container under nitrogen, sterilized in a steam autoclave, and cooled. After passing the test, an emulsion for injection of Compound 7 was obtained.

Example 28

Prescription

| Compound 7 | 10 g |
|---|---|
| Soybean oil | 50 g |
| Medium-chain triglyceride | 50 g |
| Egg-yolk lecithin | 18 g |
| Glycerol | 22.5 g |
| Sodium oleate | 1 g |
| Sodium hydroxide | appropriate amount |
| Water for injection, added up to | 1000 ml |

Under nitrogen protection, soybean oil for injection (from AVIC (Tieling) Pharmaceutical Co. Ltd.) and medium chain triglyceride (from AVIC (Tieling) Pharmaceutical Co. Ltd.) were mixed and heated to about 50° C., Egg-yolk lecithin (from Lipoid GmbH, Germany) and Compound 7 were added thereto under high-speed stirring until uniform, and the temperature was controlled at 70° C. to 75° C. to obtain an oil phase; glycerol for injection (from Hunan ER-KANG Pharmaceutical Co. Ltd.) and sodium oleate were added to an appropriate amount of water for injection and mixed, the pH of the aqueous phase was adjusted to 10.0, and the temperature was controlled at 70° C. to 75° C. to obtain an aqueous phase. Under high-speed stirring (with a high-shear mixing emulsifying machine, from IKA), the oil phase was added to the aqueous phase to make an initial emulsion, which was continuously homogenized with a high pressure homogenizer (GEA Niro) until the emulsion particles met the requirements under examination. Then the emulsion was filtered, sealed in a container under nitrogen, sterilized in a steam autoclave, and cooled. After passing the test, an emulsion for injection of Compound 7 was obtained.

Example 29

Prescription

| Compound 7 | 10 g |
|---|---|
| Solutol HS 15 | 60 g |
| Ethanol | 50 g |
| Sodium hydroxide or hydrochloric acid | appropriate amount |
| Water for injection, added up to | 1000 ml |

Prescribed amounts of Compound 7, Solutol HS 15 (from BASF, Germany), and ethanol (from Hunan ER-KANG Pharmaceutical Co. Ltd.), at a temperature controlled at 50°

C. to 55° C., were dissolved and thoroughly mixed to obtain Mixed solution (1). Under stirring, the Mixed solution (1) was slowly added to a volume of water for rejection which was 50% of the total water volume required for the formulation, followed by thorough stirring to obtain a clear solution. Injection needle-compatible activated carbon was added at 0.1 w/v %, followed by stirring for 15 min to allow adsorption, then the carbon was removed by filtration, the pH was adjusted to 6.5, and a volume of water for injection was added to make up the total volume required for the formulation, followed by thorough stirring. The mixture was filtered through a 0.22 μm filter, and sealed in a container under nitrogen. After autoclaving (121° C. for 12 min), the formulation as an aqueous solution was obtained.

Example 30

Prescription

| | |
|---|---|
| Compound 7 | 10 g |
| Solutol HS 15 | 60 g |
| Ethanol | 50 g |
| BHA | 0.1 |
| BHT | 0.1 |
| EDTA-2Na | 0.1 |
| Sodium hydroxide or hydrochloric acid | appropriate amount |
| Water for injection, added up to | 1000 ml |

Prescribed amounts of Compound 7, Solutol HS 15 (from BASF, Germany), ethanol (from Hunan ER-KANG Pharmaceutical Co. Ltd.), BHA (from Sichuan Haisco Pharmaceutical Co., Ltd.) and BHT (from Sichuan Haisco Pharmaceutical Co., Ltd.), at a temperature controlled at 60° C. to 65° C., were dissolved and thoroughly mixed to obtain Mixed solution (1). A prescribed amount of EDTA-2Na was added to a volume of water for rejection which was 60% of the total water volume required for the formulation, and dissolved under stirring, followed by thorough mixing to obtain Mixed solution (2). Under stirring, (2) was slowly added to (1), followed by thorough stirring to obtain a clear solution. Injection needle-compatible activated carbon was added at 0.1 w/v %, followed by stirring for 15 min to allow adsorption, then the carbon was removed by filtration, the pH was adjusted to 7.5, and a volume of water for injection was added to make up the total volume required for the formulation, followed by thorough stirring. The mixture was filtered through a 0.22 μm filter, and sealed in a container under nitrogen. After autoclaving (121° C. for 12 min), the formulation as an aqueous solution was obtained.

Example 31

Prescription

| | |
|---|---|
| Compound 7 | 10 g |
| Solutol HS 15 | 60 g |
| Propylene glycol | 100 g |
| BHA | 0.1 |
| BHT | 0.1 |
| EDTA-2Na | 0.1 |
| Sodium hydroxide or hydrochloric acid | appropriate amount |
| Water for injection, added up to | 1000 ml |

Prescribed amounts of Compound 7, Solutol HS 15 (from BASF, Germany), BHA (from Sichuan Haisco Pharmaceutical Co., Ltd.) and BHT (from Sichuan Haisco Pharmaceutical Co., Ltd.), at a temperature controlled at 70° C. to 75° C., were dissolved and thoroughly mixed to obtain Mixed solution (1). Prescribed amounts of EDTA-2Na and propylene glycol (from Hunan ER-KANG Pharmaceutical Co. Ltd.) were added to a volume of water for rejection which was 70% of the total water volume required for the formulation, and dissolved under stirring, followed by thorough mixing to obtain Mixed solution (2). Under stirring, (2) was slowly added to (1), followed by thorough stirring to obtain a clear solution. Injection needle-compatible activated carbon was added at 0.1 w/v %, followed by stirring for 15 min to allow adsorption, then the carbon was removed by filtration, the pH was adjusted to 8.5, and a volume of water for injection was added to make up the total volume required for the formulation, followed by thorough stirring. The mixture was filtered through a 0.22 μm filter, and sealed in a container under nitrogen. After autoclaving (121° C. for 12 min), the formulation as an aqueous solution was obtained.

Example 32

Prescription

| | |
|---|---|
| Compound 7 | 20 g |
| Solutol HS 15 | 80 g |
| Propylene glycol | 100 g |
| BHA | 0.1 |
| BHT | 0.1 |
| Sodium hydroxide or hydrochloric acid | appropriate amount |
| Water for injection, added up to | 1000 ml |

Prescribed amounts of Compound 7, Solutol HS 15 (from BASF, Germany), BHA (from Sichuan Haisco Pharmaceutical Co., Ltd.) and BHT (from Sichuan Haisco Pharmaceutical Co., Ltd.), at a temperature controlled at 75° C. to 80° C., were dissolved and thoroughly mixed to obtain Mixed solution (1). A prescribed amount of propylene glycol (from Hunan ER-KANG Pharmaceutical Co. Ltd.) were added to a volume of water for rejection which was 80% of the total water volume required for the formulation, and dissolved under stirring, followed by thorough mixing to obtain Mixed solution (2). Under stirring, (2) was slowly added to (1), followed by thorough stirring to obtain a clear solution. Injection needle-compatible activated carbon was added at 0.1 w/v %, followed by stirring for 15 min to allow adsorption, then the carbon was removed by filtration, the pH was adjusted to 8.5, and a volume of water for injection was added to make up the total volume required for the formulation, followed by thorough stirring. The mixture was filtered through a 0.22 Lm filter, and sealed in a container under nitrogen. After autoclaving (121° C. for 12 min), the formulation as an aqueous solution was obtained.

Example 33

Prescription

| | |
|---|---|
| Compound 7 | 5 g |
| Solutol HS 15 | 50 g |
| Propylene glycol | 100 g |
| EDTA-2Na | 0.1 |
| Sodium hydroxide or hydrochloric acid | appropriate amount |
| Water for injection, added up to | 1000 ml |

Prescribed amounts of Compound 7 and Solutol HS 15 (from BASF, Germany), at a temperature controlled at 50° C. to 55° C., were dissolved and thoroughly mixed to obtain Mixed solution (1). Prescribed amounts of EDTA-2Na and propylene glycol (from Hunan ER-KANG Pharmaceutical Co. Ltd.) were added to a volume of water for rejection which was 60% of the total water volume required for the formulation, and dissolved under stirring, followed by thorough mixing to obtain Mixed solution (2). Under stirring, (2) was slowly added to (1), followed by thorough stirring to obtain a clear solution. Injection needle-compatible activated carbon was added at 0.1 w/v %, followed by stirring for 15 min to allow adsorption, then the carbon was removed by filtration, the pH was adjusted to 5.5, and a volume of water for injection was added to make up the total volume required for the formulation, followed by thorough stirring. The mixture was filtered through a 0.22 μm filter, and sealed in a container under nitrogen. After autoclaving (121° C. for 12 min), the formulation as an aqueous solution was obtained.

Example 34

Prescription

| | |
|---|---|
| Compound 7 | 10 g |
| Tween-80 | 50 g |
| Tween-20 | 5 g |
| Ethanol | 100 g |
| BHA | 0.1 |
| BHT | 0.1 |
| EDTA-2Na | 0.1 |
| Sodium hydroxide or hydrochloric acid | appropriate amount |
| Water for injection, added up to | 1000 ml |

Prescribed amounts of Compound 7, Tween-80 (from Nanjing Well Chemical Co. Ltd.), Tween-20 (from Nanjing Well Chemical Co. Ltd.), BHA (from Sichuan Haisco Pharmaceutical Co., Ltd.), BHT (from Sichuan Haisco Pharmaceutical Co., Ltd.), and ethanol (from Hunan ER-KANG Pharmaceutical Co. Ltd.), at a temperature controlled at 40° C. to 45° C., were thoroughly mixed to obtain Mixed solution (1). A prescribed amount of EDTA-2Na was added to a volume of water for rejection which was 70% of the total water volume required for the formulation, and dissolved under stirring, followed by thorough mixing to obtain Mixed solution (2). Under stirring, (2) was slowly added to (1), followed by thorough stirring to obtain a clear solution.

Injection needle-compatible activated carbon was added at 0.1 w/v %, followed by stirring for 15 min to allow adsorption, then the carbon was removed by filtration, the pH was adjusted to 4.5, and a volume of water for injection was added to make up the total volume required for the formulation, followed by thorough stirring. The mixture was filtered through a 0.22 μm filter, and sealed in a container under nitrogen. After autoclaving (121° C. for 8 min), the formulation as an aqueous solution was obtained.

Example 35

Prescription

| | |
|---|---|
| Compound 7 | 20 g |
| Tween-80 | 80 g |
| Tween-20 | 5 g |
| Ethanol | 100 g |
| BHA | 0.1 |
| BHT | 0.1 |
| Sodium hydroxide or hydrochloric acid | appropriate amount |
| Water for injection, added up to | 1000 ml |

Prescribed amounts of Compound 7, Tween-80 (from Nanjing Well Chemical Co. Ltd.), Tween-20 (from Nanjing Well Chemical Co. Ltd.), BHA (from Sichuan Haisco Pharmaceutical Co., Ltd.), BHT (from Sichuan Haisco Pharmaceutical Co., Ltd.), and ethanol (from Hunan ER-KANG Pharmaceutical Co. Ltd.), at a temperature controlled at 30° C. to 35° C., were thoroughly mixed to obtain Mixed solution (1). (1) was added to a volume of water for rejection which was 65% of the total water volume required for the formulation, and dissolved under stirring, followed by thorough mixing to obtain Mixed solution (2). Under stirring, (2) was slowly added to (1), followed by thorough stirring to obtain a clear solution. Injection needle-compatible activated carbon was added at 0.1 w/v %, followed by stirring for 15 min to allow adsorption, then the carbon was removed by filtration, the pH was adjusted to 9.5, and a volume of water for injection was added to make up the total volume required for the formulation, followed by thorough stirring. The mixture was filtered through a 0.22 μm filter, and sealed in a container under nitrogen. After autoclaving (121° C. for 8 min), the formulation as an aqueous solution was obtained.

Example 36

Prescription

| | |
|---|---|
| Compound 7 | 0.1 g |
| Tween-80 | 1 g |
| Ethanol | 1 g |
| BHA | 0.1 |
| BHT | 0.1 |
| EDTA-2Na | 0.1 |
| Sodium hydroxide or hydrochloric acid | appropriate amount |
| Water for injection, added up to | 1000 ml |

Prescribed amounts of Compound 7, Tween-80 (from Nanjing Well Chemical Co. Ltd.), BHA (from Sichuan Haisco Pharmaceutical Co., Ltd.), BHT (from Sichuan Haisco Pharmaceutical Co., Ltd.), and ethanol (from Hunan ER-KANG Pharmaceutical Co. Ltd.), at a temperature controlled at 55° C. to 60° C., were thoroughly mixed to obtain Mixed solution (1). A prescribed amount of EDTA-2Na was added to a volume of water for rejection which was 75% of the total water volume required for the formulation, and dissolved under stirring, followed by thorough mixing to obtain Mixed solution (2). Under stirring, (1) was slowly added to (2), followed by thorough stirring to obtain a clear solution. Injection needle-compatible activated carbon was added at 0.1 w/v %, followed by stirring for 15 min to allow adsorption, then the carbon was removed by filtration, the pH was adjusted to 8.5, and a volume of water for injection was added to make up the total volume required for the formulation, followed by thorough stirring. The mixture was filtered through a 0.22 μm filter, and sealed in a container under nitrogen.

After autoclaving (121° C. for 12 min), the formulation as an aqueous solution was obtained.

Example 37

Prescription

| | |
|---|---|
| Compound 7 | 10 g |
| Tween-80 | 50 g |
| Tween-20 | 5 g |
| Propylene glycol | 100 g |
| EDTA-2Na | 0.1 |
| Sodium hydroxide or hydrochloric acid | appropriate amount |
| Water for injection, added up to | 1000 ml |

Prescribed amounts of Compound 7, Tween-80 (from Nanjing Well Chemical Co. Ltd.), Tween-20 (from Nanjing Well Chemical Co. Ltd.), and ethanol (from Hunan ER-KANG Pharmaceutical Co. Ltd.), at a temperature controlled at 30° C. to 35° C., were thoroughly mixed to obtain Mixed solution (1). Prescribed amounts of EDTA-2Na and propylene glycol (from Hunan ER-KANG Pharmaceutical Co. Ltd.) were added to a volume of water for rejection which was 55% of the total water volume required for the formulation, and dissolved under stirring, followed by thorough mixing to obtain Mixed solution (2). Under stirring, (1) was slowly added to (2), followed by thorough stirring to obtain a clear solution. Injection needle-compatible activated carbon was added at 0.1 w/v %, followed by stirring for 15 min to allow adsorption, then the carbon was removed by filtration, the pH was adjusted to 7.0, and a volume of water for injection was added to make up the total volume required for the formulation, followed by thorough stirring. The mixture was filtered through a 0.22 μm filter, and sealed in a container under nitrogen. After autoclaving (121° C. for 12 min), the formulation as an aqueous solution was obtained.

Example 38

Prescription

| | |
|---|---|
| Compound 7 | 30 g |
| Solutol HS 15 | 200 g |
| Propylene glycol | 300 g |
| BHA | 0.1 |
| BHT | 0.1 |
| Sodium hydroxide or hydrochloric acid | appropriate amount |
| Water for injection, added up to | 1000 ml |

Prescribed amounts of Compound 7, Solutol HS 15 (from BASF, Germany), Tween-80 (from Nanjing Well Chemical Co. Ltd.), BHA (from Sichuan Haisco Pharmaceutical Co., Ltd.), BHT (from Sichuan Haisco Pharmaceutical Co., Ltd.), and ethanol (from Hunan ER-KANG Pharmaceutical Co. Ltd.), at a temperature controlled at 55° C. to 60° C., were thoroughly mixed to obtain Mixed solution (1). A prescribed amount of propylene glycol (from Hunan ER-KANG Pharmaceutical Co.

Ltd.) were added to a volume of water for rejection which was 80% of the total water volume required for the formulation, and dissolved under stirring, followed by thorough mixing to obtain Mixed solution (2). Under stirring, (1) was slowly added to (2), followed by thorough stirring to obtain a clear solution. Injection needle-compatible activated carbon was added at 0.1 w/v %, followed by stirring for 15 min to allow adsorption, then the carbon was removed by filtration, the pH was adjusted to 8.5, and a volume of water for injection was added to make up the total volume required for the formulation, followed by thorough stirring. The mixture was filtered through a 0.22 μm filter, and sealed in a container under nitrogen. After autoclaving (121° C. for 12 min), the formulation as an aqueous solution was obtained.

Example 39

Prescription

| | |
|---|---|
| Compound 7 | 20 g |
| Solutol HS 15 | 80 g |
| Ethanol | 30 g |
| Mannitol | 160 g |
| Sodium hydroxide or hydrochloric acid | appropriate amount |
| Water for injection, added up to | 1000 ml |

Prescribed amounts of Compound 7, Solutol HS 15 (from BASF, Germany), and ethanol (from Hunan ER-KANG Pharmaceutical Co. Ltd.), at a temperature controlled at 50° C. to 55° C., were dissolved and thoroughly mixed to obtain Mixed solution (1).

A prescribed amount of mannitol (from Guangxi Nanning Chemical Pharmaceutical Co. Ltd.) was added to a volume of water for rejection which was 60% of the total water volume required for the formulation, to obtain Mixed solution (2).

Under stirring, (2) was slowly added to (1), followed by thorough stirring to obtain a clear solution. Injection needle-compatible activated carbon was added at 0.1 w/v %, followed by stirring for 15 min to allow adsorption, then the carbon was removed by filtration, the pH was adjusted to 8, and a volume of water for injection was added to make up the total volume required for the formulation, followed by thorough stirring. The mixture was filtered through a 0.22 μm filter, and then fed into a 30 ml penicillin bottle at 10 ml/bottle. The bottle was loosely plugged, and pre-frozen in a lyophilizer. The partition board was cooled to a temperature of −35° C. or lower which was maintained for 2 h. Then the chamber was cooled to −50° C. or lower and vacuumed to 20 Pa or lower. The limited leakage valve was open to allow the temperature to rise to −5° C. over 5 h which was maintained for further 10 h, then rise to 10° C. over 4 h which was maintained until the temperature of the product reached 0° C. or higher, and rise to 35° C. over 3 h which was maintained until the temperature of the product reached 25° C. or higher. Then the limited leakage valve was closed, and the temperature was maintained for 2 h. The plug is tightened up by charging $N_2$ in a vacuum, and the bottle is taken out of the lyophilizer and capped by pressing.

Example 40

Prescription

| | |
|---|---|
| Compound 7 | 10 g |
| Solutol HS 15 | 60 g |
| Ethanol | 15 g |
| Mannitol | 120 |
| BHA | 0.1 |
| BHT | 0.1 |
| Sodium hydroxide or hydrochloric acid | appropriate amount |
| Water for injection, added up to | 1000 ml |

Prescribed amounts of Compound 7, Solutol HS 15 (from BASF, Germany), ethanol (from Hunan ER-KANG Pharmaceutical Co. Ltd.), BHA (from Sichuan Haisco Pharmaceutical Co., Ltd.) and BHT (from Sichuan Haisco Pharmaceutical Co., Ltd.), at a temperature controlled at 60° C. to 65° C., were dissolved and thoroughly mixed to obtain Mixed solution (1). A prescribed amount of mannitol (from Guangxi Nanning Chemical Pharmaceutical Co. Ltd.) was added to a volume of water for rejection which was 70% of the total water volume required for the formulation, to obtain Mixed solution (2). Under stirring, (2) was slowly added to (1), followed by thorough stirring to obtain a clear solution. Injection needle-compatible activated carbon was added at 0.1 w/v %, followed by stirring for 15 min to allow adsorption, then the carbon was removed by filtration, the pH was adjusted to 8.0, and a volume of water for injection was added to make up the total volume required for the formulation, followed by thorough stirring. The mixture was filtered through a 0.22 μm filter, and then fed into a 30 ml penicillin bottle at 10 ml/bottle. The bottle was loosely plugged, and pre-frozen in a lyophilizer.

The partition board was cooled to a temperature of −35° C. or lower which was maintained for 2 h. Then the chamber was cooled to −50° C. or lower and vacuumed to 20 Pa or lower. The limited leakage valve was open to allow the temperature to rise to −5° C. over 5 h which was maintained for further 10 h, then rise to 10° C. over 4 h which was maintained until the temperature of the product reached 0° C. or higher, and rise to 35° C. over 3 h which was maintained until the temperature of the product reached 25° C. or higher. Then the limited leakage valve was closed, and the temperature was maintained for 2 h.

The plug is tightened up by charging $N_2$ in a vacuum, and the bottle is taken out of the lyophilizer and capped by pressing.

Example 41

Prescription

| | |
|---|---|
| Compound 7 | 2 g |
| Tween-80 | 10 g |
| Tween-20 | 1 g |
| Ethanol | 2 g |
| Mannitol | 80 |
| Sodium hydroxide or hydrochloric acid | appropriate amount |
| Water for injection, added up to | 1000 ml |

Prescribed amounts of Compound 7, Tween-80 (from Nanjing Well Chemical Co. Ltd.), Tween-20 (from Nanjing Well Chemical Co. Ltd.), and ethanol (from Hunan ER-KANG Pharmaceutical Co. Ltd.), at a temperature controlled at 40° C. to 45° C., were thoroughly mixed to obtain Mixed solution (1). A prescribed amount of mannitol (from Guangxi Nanning Chemical Pharmaceutical Co. Ltd.) was added to a volume of water for rejection which was 75% of the total water volume required for the formulation, dissolved, and thoroughly mixed to obtain Mixed solution (2). Under stirring, (2) was slowly added to (1), followed by thorough stirring to obtain a clear solution. Injection needle-compatible activated carbon was added at 0.1 w/v %, followed by stirring for 15 min to allow adsorption, then the carbon was removed by filtration, the pH was adjusted to 6.0, and a volume of water for injection was added to make up the total volume required for the formulation, followed by thorough stirring. The mixture was filtered through a 0.22 μm filter, and then fed into a 30 ml penicillin bottle at 10 ml/bottle. The bottle was loosely plugged, and pre-frozen in a lyophilizer.

The partition board was cooled to a temperature of −35° C. or lower which was maintained for 2 h. Then the chamber was cooled to −50° C. or lower and vacuumed to 20 Pa or lower. The limited leakage valve was open to allow the temperature to rise to −5° C. over 5 h which was maintained for further 10 h, then rise to 10° C. over 4 h which was maintained until the temperature of the product reached 0° C. or higher, and rise to 35° C. over 3 h which was maintained until the temperature of the product reached 25° C. or higher. Then the limited leakage valve was closed, and the temperature was maintained for 2 h.

The plug is tightened up by charging $N_2$ in a vacuum, and the bottle is taken out of the lyophilizer and capped by pressing.

Example 42

Prescription

| | |
|---|---|
| Compound 7 | 0.2 g |
| Tween-80 | 1 g |
| Ethanol | 1 g |
| Mannitol | 80 g |
| EDTA-2Na | 0.1 |
| Sodium hydroxide or hydrochloric acid | appropriate amount |
| Water for injection, added up to | 1000 ml |

Prescribed amounts of Compound 7, Tween-80 (from Nanjing Well Chemical Co. Ltd.), Tween-20 (from Nanjing Well Chemical Co. Ltd.), and ethanol (from Hunan ER-KANG Pharmaceutical Co. Ltd.), at a temperature controlled at 55° C. to 60° C., were thoroughly mixed to obtain Mixed solution (1). Prescribed amounts of mannitol (from Guangxi Nanning Chemical Pharmaceutical Co. Ltd.) and EDTA-2Na were added to a volume of water for rejection which was 65% of the total water volume required for the formulation, dissolved, and thoroughly mixed to obtain Mixed solution (2). Under stirring, (2) was slowly added to (1), followed by thorough stirring to obtain a clear solution. Injection needle-compatible activated carbon was added at 0.1 w/v %, followed by stirring for 15 min to allow adsorption, then the carbon was removed by filtration, the pH was adjusted to 7.5, and a volume of water for injection was added to make up the total volume required for the formulation, followed by thorough stirring. The mixture was filtered through a 0.22 μm filter, and then fed into a 20 ml penicillin bottle at 5 ml/bottle. The bottle was loosely plugged, and pre-frozen in a lyophilizer.

The partition board was cooled to a temperature of −35° C. or lower which was maintained for 1 h to 2 h. Then the chamber was cooled to −50° C. or lower and vacuumed to 20 Pa or lower. The limited leakage valve was open to allow the temperature to rise to −5° C. over 4 h which was maintained for further 6 h, then rise to 10° C. over 4 h which was maintained until the temperature of the product reached 0° C. or higher, and rise to 35° C. over 3 h which was maintained until the temperature of the product reached 25° C. or higher. Then the limited leakage valve was closed, and the temperature was maintained for 2 h.

The plug is tightened up by charging $N_2$ in a vacuum, and the bottle is taken out of the lyophilizer and capped by pressing.

Example 43

Prescription

| | |
|---|---|
| Compound 10 (or Compound 9) | 11 g |
| Soybean oil | 50 g |
| Medium-chain triglyceride | 50 g |
| Egg-yolk lecithin | 12 g |
| Glycerol | 22.5 g |
| Sodium oleate | 0.3 g |
| Sodium hydroxide | appropriate amount |
| Water for injection, added up to | 1000 ml |

Under nitrogen protection, soybean oil for injection (from AVIC (Tieling) Pharmaceutical Co. Ltd.) and medium chain triglyceride (from AVIC (Tieling) Pharmaceutical Co. Ltd.) were mixed and heated to about 50° C., Egg-yolk lecithin (from Lipoid GmbH, Germany) and Compound 10 (or Compound 9) were added thereto under high-speed stirring until uniform, and the temperature was controlled at 70° C. to 75° C. to obtain an oil phase; glycerol for injection (from Hunan ER-KANG Pharmaceutical Co. Ltd.) and sodium oleate were added to an appropriate amount of water for injection and mixed, the pH of the aqueous phase was adjusted to 10.0, and the temperature was controlled at 70° C. to 75° C. to obtain an aqueous phase. Under high-speed stirring (with a high-shear mixing emulsifying machine, from IKA), the oil phase was added to the aqueous phase to make an initial emulsion, which was continuously homogenized with a high pressure homogenizer (GEA Niro) until the emulsion particles met the requirements under examination. Then the emulsion was filtered, sealed in a container under nitrogen, sterilized in a steam autoclave, and cooled. After passing the test, an emulsion for injection of Compound 10 (or Compound 9) was obtained.

Example 44

Prescription

| | |
|---|---|
| Compound 2 | 10.5 g |
| Soybean oil | 50 g |
| Medium-chain triglyceride | 50 g |
| Egg-yolk lecithin | 12 g |
| Glycerol | 22.5 g |
| Sodium oleate | 0.3 g |
| Sodium hydroxide | appropriate amount |
| Water for injection, added up to | 1000 ml |

Under nitrogen protection, soybean oil for injection (from AVIC (Tieling) Pharmaceutical Co. Ltd.) and medium chain triglyceride (from AVIC (Tieling) Pharmaceutical Co. Ltd.) were mixed and heated to about 50° C., Egg-yolk lecithin (from Lipoid GmbH, Germany) and Compound 2 were added thereto under high-speed stirring until uniform, and the temperature was controlled at 55° C. to 60° C. to obtain an oil phase; glycerol for injection (from Hunan ER-KANG Pharmaceutical Co. Ltd.) and sodium oleate were added to an appropriate amount of water for injection and mixed, the pH of the aqueous phase was adjusted to 9.0, and the temperature was controlled at 55° C. to 60° C. to obtain an aqueous phase. Under high-speed stirring (with a high-shear mixing emulsifying machine, from IKA), the oil phase was added to the aqueous phase to make an initial emulsion, which was continuously homogenized with a high pressure homogenizer (GEA Niro) until the emulsion particles met the requirements under examination. Then the emulsion was filtered, sealed in a container under nitrogen, sterilized in a steam autoclave, and cooled. After passing the test, an emulsion for injection of Compound 2 was obtained.

Example 45

Prescription

| | |
|---|---|
| Compound 10 (or Compound 9) | 11 g |
| Solutol HS 15 | 60 g |
| Ethanol | 50 g |
| Sodium hydroxide or hydrochloric acid | appropriate amount |
| Water for injection, added up to | 1000 ml |

Prescribed amounts of Compound 10 (or Compound 9), Solutol HS 15 (from BASF, Germany), and ethanol (from Hunan ER-KANG Pharmaceutical Co. Ltd.), at a temperature controlled at 60° C. to 65° C., were dissolved and thoroughly mixed to obtain Mixed solution (1). Under stirring, the Mixed solution (1) was slowly added to a volume of water for rejection which was 70% of the total water volume required for the formulation, followed by thorough stirring to obtain a clear solution. Injection needle-compatible activated carbon was added at 0.1 w/v %, followed by stirring for 15 min to allow adsorption, then the carbon was removed by filtration, the pH was adjusted to 7, and a volume of water for injection was added to make up the total volume required for the formulation, followed by thorough stirring. The mixture was filtered through a 0.22 μm filter, and sealed in a container under nitrogen. After autoclaving (121° C. for 12 min), the formulation as an aqueous solution was obtained.

Example 46

Prescription

| | |
|---|---|
| Compound 2 | 10 g |
| Solutol HS 15 | 60 g |
| Ethanol | 50 g |
| Sodium hydroxide or hydrochloric acid | appropriate amount |
| Water for injection, added up to | 1000 ml |

Prescribed amounts of Compound 2, Solutol HS 15 (from BASF, Germany), and ethanol (from Hunan ER-KANG Pharmaceutical Co. Ltd.), at a temperature controlled at 75° C. to 80° C., were dissolved and thoroughly mixed to obtain Mixed solution (1). Under stirring, the Mixed solution (1) was slowly added to a volume of water for rejection which was 60% of the total water volume required for the formulation, followed by thorough stirring to obtain a clear solution. Injection needle-compatible activated carbon was added at 0.1 w/v %, followed by stirring for 15 min to allow adsorption, then the carbon was removed by filtration, the pH was adjusted to 9.5, and a volume of water for injection was added to make up the total volume required for the formulation, followed by thorough stirring. The mixture was filtered through a 0.22 μm filter, and sealed in a container under nitrogen. After autoclaving (121° C. for 12 min), the formulation as an aqueous solution was obtained.

Example 47

Prescription

| | |
|---|---|
| Compound 10 (or Compound 9) | 11 g |
| Tween-80 | 50 g |
| Tween-20 | 5 g |
| Ethanol | 30 g |
| Mannitol | 120 |
| Sodium hydroxide or hydrochloric acid | appropriate amount |
| Water for injection, added up to | 1000 ml |

Prescribed amounts of Compound 10 (or Compound 9), Tween-80 (from Nanjing Well Chemical Co. Ltd.), Tween-20 (from Nanjing Well Chemical Co. Ltd.), and ethanol (from Hunan ER-KANG Pharmaceutical Co. Ltd.), at a temperature controlled at 30° C. to 35° C., were thoroughly mixed to obtain Mixed solution (1). A prescribed amount of mannitol (from Guangxi Nanning Chemical Pharmaceutical Co. Ltd.) was added to a volume of water for rejection which was 65% of the total water volume required for the formulation, dissolved, and thoroughly mixed to obtain Mixed solution (2). Under stirring, (2) was slowly added to (1), followed by thorough stirring to obtain a clear solution. Injection needle-compatible activated carbon was added at 0.1 w/v %, followed by stirring for 15 min to allow adsorption, then the carbon was removed by filtration, the pH was adjusted to 8.5, and a volume of water for injection was added to make up the total volume required for the formulation, followed by thorough stirring. The mixture was filtered through a 0.22 µm filter, and then fed into a 30 ml penicillin bottle at 10 ml/bottle. The bottle was loosely plugged, and pre-frozen in a lyophilizer.

The partition board was cooled to a temperature of −35° C. or lower which was maintained for 2 h. Then the chamber was cooled to −50° C. or lower and vacuumed to 20 Pa or lower. The limited leakage valve was open to allow the temperature to rise to −5° C. over 5 h which was maintained for further 10 h, then rise to 10° C. over 4 h which was maintained until the temperature of the product reached 0° C. or higher, and rise to 35° C. over 3 h which was maintained until the temperature of the product reached 25° C. or higher. Then the limited leakage valve was closed, and the temperature was maintained for 2 h.

Example 48

Prescription

| | |
|---|---|
| Compound 2 | 10.5 g |
| Tween-80 | 50 g |
| Tween-20 | 5 g |
| Ethanol | 20 g |
| Mannitol | 120 |
| Sodium hydroxide or hydrochloric acid | appropriate amount |
| Water for injection, added up to | 1000 ml |

Prescribed amounts of Compound 2, Tween-80 (from Nanjing Well Chemical Co. Ltd.), Tween-20 (from Nanjing Well Chemical Co. Ltd.), and ethanol (from Hunan ER-KANG Pharmaceutical Co. Ltd.), at a temperature controlled at 35° C. to 40° C., were thoroughly mixed to obtain Mixed solution (1). A prescribed amount of mannitol (from Guangxi Nanning Chemical Pharmaceutical Co. Ltd.) were added to a volume of water for rejection which was 50% of the total water volume required for the formulation, dissolved, and thoroughly mixed to obtain Mixed solution (2). Under stirring, (2) was slowly added to (1), followed by thorough stirring to obtain a clear solution. Injection needle-compatible activated carbon was added at 0.1 w/v %, followed by stirring for 15 min to allow adsorption, then the carbon was removed by filtration, the pH was adjusted to 4.5, and a volume of water for injection was added to make up the total volume required for the formulation, followed by thorough stirring. The mixture was filtered through a 0.22 µm filter, and then fed into a 30 ml penicillin bottle at 10 ml/bottle. The bottle was loosely plugged, and pre-frozen in a lyophilizer.

The partition board was cooled to a temperature of −35° C. or lower which was maintained for 2 h. Then the chamber was cooled to −50° C. or lower and vacuumed to 20 Pa or lower. The limited leakage valve was open to allow the temperature to rise to −5° C. over 5 h which was maintained for further 10 h, then rise to 10° C. over 4 h which was maintained until the temperature of the product reached 0° C. or higher, and rise to 35° C. over 3 h which was maintained until the temperature of the product reached 25° C. or higher. Then the limited leakage valve was closed, and the temperature was maintained for 2 h.

Example 49

Prescription

| | |
|---|---|
| Compound 7 | 0.5 g |
| Soybean oil | 25 g |
| Medium-chain triglyceride | 25 g |
| Egg-yolk lecithin | 12 g |
| Glycerol | 22.5 g |
| Sodium oleate | 0.1 g |
| Sodium hydroxide | appropriate amount |
| Water for injection, added up to | 1000 ml |

Under nitrogen protection, soybean oil for injection (from AVIC (Tieling) Pharmaceutical Co. Ltd.) and medium chain triglyceride (from AVIC (Tieling) Pharmaceutical Co. Ltd.) were mixed and heated to about 50° C., Egg-yolk lecithin (from Lipoid GmbH, Germany) and Compound 7 were added thereto under high-speed stirring until uniform, and the temperature was controlled at 60° C. to 65° C. to obtain an oil phase; glycerol for injection (from Hunan ER-KANG Pharmaceutical Co. Ltd.) and sodium oleate were added to an appropriate amount of water for injection and mixed, the pH of the aqueous phase was adjusted to 9.5, and the temperature was controlled at 60° C. to 65° C. to obtain an aqueous phase. Under high-speed stirring (with a high-shear mixing emulsifying machine, from IKA), the oil phase was added to the aqueous phase to make an initial emulsion, which was continuously homogenized with a high pressure homogenizer (GEA Niro) until the emulsion particles met the requirements under examination. Then the emulsion was filtered, sealed in a container under nitrogen, sterilized in a steam autoclave, and cooled. After passing the test, an emulsion for injection of Compound 7 was obtained.

Example 50

Prescription

| | |
|---|---|
| Compound 7 | 0.1 g |
| Soybean oil | 25 g |
| Medium-chain triglyceride | 25 g |
| Egg-yolk lecithin | 6 g |
| Glycerol | 20 g |
| Sodium hydroxide | appropriate amount |
| Water for injection, added up to | 1000 ml |

Under nitrogen protection, soybean oil for injection (from AVIC (Tieling) Pharmaceutical Co. Ltd.) and medium chain triglyceride (from AVIC (Tieling) Pharmaceutical Co. Ltd.) were mixed and heated to about 50° C., Egg-yolk lecithin (from Lipoid GmbH, Germany) and Compound 7 were added thereto under high-speed stirring until uniform, and the temperature was controlled at 65° C. to 70° C. to obtain an oil phase; glycerol for injection (from Hunan ER-KANG Pharmaceutical Co. Ltd.) was added to an appropriate amount of water for injection and mixed, the pH of the aqueous phase was adjusted to 11.0, and the temperature was controlled at 65° C. to 70° C. to obtain an aqueous phase. Under high-speed stirring (with a high-shear mixing emulsifying machine, from IKA), the oil phase was added to the aqueous phase to make an initial emulsion, which was continuously homogenized with a high pressure homogenizer (GEA Niro) until the emulsion particles met the requirements under examination. Then the emulsion was filtered, sealed in a container under nitrogen, sterilized in a steam autoclave, and cooled. After passing the test, an emulsion for injection of Compound 7 was obtained.

Example 51

Prescription

| | |
|---|---|
| Compound 9 | 0.5 g |
| Soybean oil | 25 g |
| Medium-chain triglyceride | 25 g |
| Egg-yolk lecithin | 12 g |
| Glycerol | 22.5 g |
| Sodium oleate | 0.3 g |
| Sodium hydroxide | appropriate amount |
| Water for injection, added up to | 1000 ml |

Under nitrogen protection, soybean oil for injection (from AVIC (Tieling) Pharmaceutical Co. Ltd.) and medium chain triglyceride (from AVIC (Tieling) Pharmaceutical Co. Ltd.) were mixed and heated to about 50° C., Egg-yolk lecithin (from Lipoid GmbH, Germany) and Compound 9 were added thereto under high-speed stirring until uniform, and the temperature was controlled at 60° C. to 65° C. to obtain an oil phase; glycerol for injection (from Hunan ER-KANG Pharmaceutical Co. Ltd.) and sodium oleate were added to an appropriate amount of water for injection and mixed, the pH of the aqueous phase was adjusted to 9.5, and the temperature was controlled at 60° C. to 65° C. to obtain an aqueous phase. Under high-speed stirring (with a high-shear mixing emulsifying machine, from IKA), the oil phase was added to the aqueous phase to make an initial emulsion, which was continuously homogenized with a high pressure homogenizer (GEA Niro) until the emulsion particles met the requirements under examination. Then the emulsion was filtered, sealed in a container under nitrogen, sterilized in a steam autoclave, and cooled. After passing the test, an emulsion for injection of Compound 9 was obtained.

Example 52

Prescription:

| | |
|---|---|
| Compound 2 | 0.3 g |
| Soybean oil | 30 g |
| Medium-chain triglyceride | 30 g |
| Egg-yolk lecithin | 12 g |
| Glycerol | 22.5 g |
| Sodium oleate | 0.3 g |
| Sodium hydroxide | appropriate amount |
| Water for injection, added up to | 1000 ml |

Under nitrogen protection, soybean oil for injection (from AVIC (Tieling) Pharmaceutical Co. Ltd.) and medium chain triglyceride (from AVIC (Tieling) Pharmaceutical Co. Ltd.) were mixed and heated to about 50° C., Egg-yolk lecithin (from Lipoid GmbH, Germany) and Compound 2 were added thereto under high-speed stirring until uniform, and the temperature was controlled at 60° C. to 65° C. to obtain an oil phase; glycerol for injection (from Hunan ER-KANG Pharmaceutical Co. Ltd.) and sodium oleate were added to an appropriate amount of water for injection and mixed, the pH of the aqueous phase was adjusted to 9.0, and the temperature was controlled at 60° C. to 65° C. to obtain an aqueous phase. Under high-speed stirring (with a high-shear mixing emulsifying machine, from IKA), the oil phase was added to the aqueous phase to make an initial emulsion, which was continuously homogenized with a high pressure homogenizer (GEA Niro) until the emulsion particles met the requirements under examination. Then the emulsion was filtered, sealed in a container under nitrogen, sterilized in a steam autoclave, and cooled. After passing the test, an emulsion for injection of Compound 2 was obtained.

Example 53

Prescription

| | |
|---|---|
| Compound 10 | 1 g |
| Solutol HS 15 | 60 g |
| Ethanol | 10 g |
| Sodium hydroxide or hydrochloric acid | appropriate amount |
| Water for injection, added up to | 1000 ml |

Prescribed amounts of Compound 10, Solutol HS 15 (from BASF, Germany), and ethanol (from Hunan ER-KANG Pharmaceutical Co. Ltd.), at a temperature controlled at 55° C. to 60° C., were dissolved and thoroughly mixed to obtain Mixed solution (1). Under stirring, the Mixed solution (1) was slowly added to a volume of water for rejection which was 60% of the total water volume required for the formulation, followed by thorough stirring to obtain a clear solution. Injection needle-compatible activated carbon was added at 0.1 w/v %, followed by stirring for 15 min to allow adsorption, then the carbon was removed by filtration, the pH was adjusted to 8.5, and a volume of water for injection was added to make up the total volume required for the formulation, followed by thorough stirring. The mixture was filtered through a 0.22 μm filter, and sealed in a container under nitrogen. After autoclaving (121° C. for 12 min), the formulation as an aqueous solution was obtained.

Example 54

Prescription

| | |
|---|---|
| Compound 9 | 1 g |
| Solutol HS 15 | 60 g |
| Ethanol | 10 g |
| Sodium hydroxide or hydrochloric acid | appropriate amount |
| Water for injection, added up to | 1000 ml |

Prescribed amounts of Compound 9, Solutol HS 15 (from BASF, Germany), and ethanol (from Hunan ER-KANG Pharmaceutical Co. Ltd.), at a temperature controlled at 55° C. to 60° C., were dissolved and thoroughly mixed to obtain Mixed solution (1). Under stirring, the Mixed solution (1) was slowly added to a volume of water for rejection which was 60% of the total water volume required for the formulation, followed by thorough stirring to obtain a clear solution. Injection needle-compatible activated carbon was added at 0.1 w/v %, followed by stirring for 15 min to allow adsorption, then the carbon was removed by filtration, the pH was adjusted to 8.5, and a volume of water for injection was added to make up the total volume required for the formulation, followed by thorough stirring. The mixture was filtered through a 0.22 μm filter, and sealed in a container under nitrogen. After autoclaving (121° C. for 12 min), the formulation as an aqueous solution was obtained.

Example 55

Prescription

| | |
|---|---|
| Compound 2 | 0.5 g |
| Solutol HS 15 | 60 g |
| Ethanol | 5 g |
| Sodium hydroxide or hydrochloric acid | appropriate amount |
| Water for injection, added up to | 1000 ml |

Prescribed amounts of Compound 2, Solutol HS 15 (from BASF, Germany), and ethanol (from Hunan ER-KANG Pharmaceutical Co. Ltd.), at a temperature controlled at 70° C. to 75° C., were dissolved and thoroughly mixed to obtain Mixed solution (1). Under stirring, the Mixed solution (1) was slowly added to a volume of water for rejection which was 65% of the total water volume required for the formulation, followed by thorough stirring to obtain a clear solution. Injection needle-compatible activated carbon was added at 0.1 w/v %, followed by stirring for 15 min to allow adsorption, then the carbon was removed by filtration, the pH was adjusted to 8.5, and a volume of water for injection was added to make up the total volume required for the formulation, followed by thorough stirring. The mixture was filtered through a 0.22 μm filter, and sealed in a container under nitrogen. After autoclaving (121° C. for 12 min), the formulation as an aqueous solution was obtained.

Example 56

Prescription

| | |
|---|---|
| Compound 10 (or Compound 9) | 0.5 g |
| Tween-80 | 50 g |
| Tween-20 | 5 g |
| Glycerol | 20 g |
| Mannitol | 80 |
| Sodium hydroxide or hydrochloric acid | appropriate amount |
| Water for injection, added up to | 1000 ml |

Prescribed amounts of Compound 10 (or Compound 9), Tween-80 (from Nanjing Well Chemical Co. Ltd.), Tween-20 (from Nanjing Well Chemical Co. Ltd.), and glycerol (from Hunan ER-KANG Pharmaceutical Co. Ltd.), at a temperature controlled at 45° C. to 50° C., were thoroughly mixed to obtain Mixed solution (1). A prescribed amount of mannitol was added to a volume of water for rejection which was 70% of the total water volume required for the formulation, and dissolved under stirring, followed by thorough mixing to obtain Mixed solution (2). Under stirring, (2) was slowly added to (1), followed by thorough stirring to obtain a clear solution. Injection needle-compatible activated carbon was added at 0.1 w/v %, followed by stirring for 15 min to allow adsorption, then the carbon was removed by filtration, the pH was adjusted to 7.5, and a volume of water for injection was added to make up the total volume required for the formulation, followed by thorough stirring. The mixture was filtered through a 0.22 μm filter, and then fed into a 30 ml penicillin bottle at 10 ml/bottle. The bottle was loosely plugged, and pre-frozen in a lyophilizer.

The partition board was cooled to a temperature of −35° C. or lower which was maintained for 2 h. Then the chamber was cooled to −50° C. or lower and vacuumed to 20 Pa or lower. The limited leakage valve was open to allow the temperature to rise to −5° C. over 5 h which was maintained for further 10 h, then rise to 10° C. over 4 h which was maintained until the temperature of the product reached 0° C. or higher, and rise to 35° C. over 3 h which was maintained until the temperature of the product reached 25° C. or higher. Then the limited leakage valve was closed, and the temperature was maintained for 2 h.

Example 57

Prescription

| | |
|---|---|
| Compound 2 | 0.1 g |
| Tween-80 | 50 g |
| Tween-20 | 5 g |
| Propylene glycol | 5 g |
| Mannitol | 120 |
| Sodium hydroxide or hydrochloric acid | appropriate amount |
| Water for injection, added up to | 1000 ml |

Prescribed amounts of Compound 2, Tween-80 (from Nanjing Well Chemical Co. Ltd.), Tween-20 (from Nanjing Well Chemical Co. Ltd.), and propylene glycol (from Hunan ER-KANG Pharmaceutical Co. Ltd.), at a temperature controlled at 55° C. to 60° C., were thoroughly mixed to obtain Mixed solution (1). A prescribed amount of mannitol (from Guangxi Nanning Chemical Pharmaceutical Co. Ltd.) were added to a volume of water for rejection which was 55% of the total water volume required for the formulation, dissolved, and thoroughly mixed to obtain Mixed solution (2). Under stirring, (2) was slowly added to (1), followed by thorough stirring to obtain a clear solution. Injection needle-compatible activated carbon was added at 0.1 w/v %, followed by stirring for 15 min to allow adsorption, then the carbon was removed by filtration, the pH was adjusted to 6.5, and a volume of water for injection was added to make up the total volume required for the formulation, followed by thorough stirring. The mixture was filtered through a 0.22 μm filter, and then fed into a 30 ml penicillin bottle at 10 ml/bottle. The bottle was loosely plugged, and pre-frozen in a lyophilizer.

The partition board was cooled to a temperature of −35° C. or lower which was maintained for 2 h. Then the chamber was cooled to −50° C. or lower and vacuumed to 20 Pa or lower. The limited leakage valve was open to allow the temperature to rise to −5° C. over 5 h which was maintained for further 10 h, then rise to 10° C. over 4 h which was maintained until the temperature of the product reached 0° C. or higher, and rise to 35° C. over 3 h which was maintained until the temperature of the product reached 25° C. or higher. Then the limited leakage valve was closed, and the temperature was maintained for 2 h.

Example 58

Prescription

| | |
|---|---|
| Compound 8 | 10 g |
| Soybean oil | 50 g |
| Medium-chain triglyceride | 50 g |
| Egg-yolk lecithin | 12 g |
| Glycerol | 22.5 g |
| Sodium oleate | 0.3 g |
| Sodium hydroxide | appropriate amount |
| Water for injection, added up to | 1000 ml |

Under nitrogen protection, soybean oil for injection (from AVIC (Tieling) Pharmaceutical Co. Ltd.) and medium chain triglyceride (from AVIC (Tieling) Pharmaceutical Co. Ltd.) were mixed and heated to about 50° C., refined Egg-yolk lecithin (from Lipoid GmbH, Germany) and Compound 8 were added thereto under high-speed stirring until uniform, and the temperature was controlled at 60° C. to 65° C. to obtain an oil phase; glycerol for injection (from Hunan ER-KANG Pharmaceutical Co. Ltd.) and sodium oleate were added to an appropriate amount of water for injection and mixed, the pH of the aqueous phase was adjusted to 10.5, and the temperature was controlled at 60° C. to 65° C. to obtain an aqueous phase. Under high-speed stirring (with a high-shear mixing emulsifying machine, from IKA), the oil phase was added to the aqueous phase to make an initial emulsion, which was continuously homogenized with a high pressure homogenizer until the emulsion particles met the requirements under examination. Then the emulsion was filtered, sealed in a container under nitrogen, sterilized in a steam autoclave, and cooled. After passing the test, an emulsion for injection of Compound 8 was obtained.

Example 59

Prescription

| | |
|---|---|
| Compound 10 | 10 g |
| Solutol HS 15 | 60 g |
| Ethanol | 15 g |
| Mannitol | 120 g |
| BHA | 0.1 |
| BHT | 0.1 |
| Sodium hydroxide or hydrochloric acid | appropriate amount |
| Water for injection, added up to | 1000 ml |

Prescribed amounts of Compound 10, Solutol HS 15 (from BASF, Germany), ethanol (from Hunan ER-KANG Pharmaceutical Co. Ltd.), BHA (from Sichuan Haisco Pharmaceutical Co., Ltd.) and BHT (from Sichuan Haisco Pharmaceutical Co., Ltd.), at a temperature controlled at 60° C. to 65° C., were dissolved and thoroughly mixed to obtain Mixed solution (1).

A prescribed amount of mannitol (from Guangxi Nanning Chemical Pharmaceutical Co. Ltd.) was added to a volume of water for rejection which was 60% of the total water volume required for the formulation, to obtain Mixed solution (2).

Under stirring, (2) was slowly added to (1), followed by thorough stirring to obtain a clear solution. Injection needle-compatible activated carbon was added at 0.1 w/v %, followed by stirring for 15 min to allow adsorption, then the carbon was removed by filtration, the pH was adjusted to 6.3, and a volume of water for injection was added to make up the total volume required for the formulation, followed by thorough stirring. The mixture was filtered through a 0.22 μm filter, and then fed into a 30 ml penicillin bottle at 10 ml/bottle. The bottle was loosely plugged, and pre-frozen in a lyophilizer.

The partition board was cooled to a temperature of −35° C. or lower which was maintained for 2 h. Then the chamber was cooled to −50° C. or lower and vacuumed to 20 Pa or lower. The limited leakage valve was open to allow the temperature to rise to −5° C. over 5 h which was maintained for further 10 h, then rise to 10° C. over 4 h which was maintained until the temperature of the product reached 0° C. or higher, and rise to 35° C. over 3 h which was maintained until the temperature of the product reached 25° C. or higher. Then the limited leakage valve was closed, and the temperature was maintained for 2 h. The plug is tightened up by charging $N_2$ in a vacuum, and the bottle is taken out of the lyophilizer and capped by pressing.

Example 60

Prescription

| | |
|---|---|
| Compound 13 | 0.2 g |
| Tween-80 | 2 g |
| Ethanol | 1 g |
| Mannitol | 80 g |
| Sodium hydroxide or hydrochloric acid | appropriate amount |
| Water for injection, added up to | 1000 ml |

Prescribed amounts of Compound 13, Tween-80 (from Nanjing Well Chemical Co. Ltd.), and ethanol (from Hunan ER-KANG Pharmaceutical Co. Ltd.), at a temperature controlled at 65° C. to 70° C., were dissolved and thoroughly mixed to obtain Mixed solution (1).

A prescribed amount of mannitol (from Guangxi Nanning Chemical Pharmaceutical Co. Ltd.) was added to a volume of water for rejection which was 60% of the total water volume required for the formulation, to obtain Mixed solution (2).

Under stirring, (2) was slowly added to (1), followed by thorough stirring to obtain a clear solution. Injection needle-compatible activated carbon was added at 0.1 w/v %, followed by stirring for 15 min to allow adsorption, then the carbon was removed by filtration, the pH was adjusted to 7.0, and a volume of water for injection was added to make up the total volume required for the formulation, followed by thorough stirring. The mixture was filtered through a 0.22 μm filter, and then fed into a 30 ml penicillin bottle at 10 ml/bottle. The bottle was loosely plugged, and pre-frozen in a lyophilizer.

The partition board was cooled to a temperature of −35° C. or lower which was maintained for 2 h. Then the chamber was cooled to −50° C. or lower and vacuumed to 20 Pa or lower. The limited leakage valve was open to allow the temperature to rise to −5° C. over 5 h which was maintained for further 8 h, then rise to 10° C. over 4 h which was maintained until the temperature of the product reached 0° C. or higher, and rise to 35° C. over 3 h which was maintained until the temperature of the product reached 25° C. or higher. Then the limited leakage valve was closed, and the temperature was maintained for 2 h. The plug is tightened up by charging $N_2$ in a vacuum, and the bottle is taken out of the lyophilizer and capped by pressing.

Example 61

Prescription

| | |
|---|---|
| Compound 16 | 20 g |
| Solutol HS 15 | 80 g |
| Propylene glycol | 30 g |
| Mannitol | 160 g |
| EDTA-2Na | 0.1 g |
| Sodium hydroxide or hydrochloric acid | appropriate amount |
| Water for injection, added up to | 1000 ml |

Prescribed amounts of Compound 16 and Solutol HS 15 (from BASF, Germany), at a temperature controlled at 75° C. to 80° C., were dissolved and thoroughly mixed to obtain Mixed solution (1).

Prescribed amounts of propylene glycol (from Hunan ER-KANG Pharmaceutical Co. Ltd.), mannitol (from Guangxi Nanning Chemical Pharmaceutical Co. Ltd.), and EDTA-2Na were added to a volume of water for rejection which was 60% of the total water volume required for the formulation, to obtain Mixed solution (2).

Under stirring, (2) was slowly added to (1), followed by thorough stirring to obtain a clear solution. Injection needle-compatible activated carbon was added at 0.1 w/v %, followed by stirring for 15 min to allow adsorption, then the carbon was removed by filtration, the pH was adjusted to 5.4, and a volume of water for injection was added to make up the total volume required for the formulation, followed by thorough stirring. The mixture was filtered through a 0.22 μm filter, and then fed into a 30 ml penicillin bottle at 10 ml/bottle. The bottle was loosely plugged, and pre-frozen in a lyophilizer.

The partition board was cooled to a temperature of −35° C. or lower which was maintained for 2 h. Then the chamber was cooled to −50° C. or lower and vacuumed to 20 Pa or lower. The limited leakage valve was open to allow the temperature to rise to −5° C. over 5 h which was maintained for further 12 h, then rise to 10° C. over 5 h which was maintained until the temperature of the product reached 0° C. or higher, and rise to 35° C. over 3 h which was maintained until the temperature of the product reached 25° C. or higher. Then the limited leakage valve was closed, and the temperature was maintained for 2 h. The plug is tightened up by charging $N_2$ in a vacuum, and the bottle is taken out of the lyophilizer and capped by pressing.

Example 62

Prescription

| | |
|---|---|
| Compound 14 | 10 g |
| Tween-80 | 60 g |
| Tween-20 | 6 g |
| Ethanol | 15 g |
| Mannitol | 120 g |
| BHA | 0.1 |
| BHT | 0.1 |
| Sodium hydroxide or hydrochloric acid | appropriate amount |
| Water for injection, added up to | 1000 ml |

Prescribed amounts of Compound 14, Tween-80 (from Nanjing Well Chemical Co. Ltd.), Tween-20 (from Nanjing Well Chemical Co. Ltd.), ethanol (from Hunan ER-KANG Pharmaceutical Co. Ltd.), BHA (from Sichuan Haisco Pharmaceutical Co., Ltd.), and BHT (from Sichuan Haisco Pharmaceutical Co., Ltd.), at a temperature controlled at 60° C. to 65° C., were thoroughly mixed to obtain Mixed solution (1).

A prescribed amount of mannitol (from Guangxi Nanning Chemical Pharmaceutical Co. Ltd.) was added to a volume of water for rejection which was 60% of the total water volume required for the formulation, to obtain Mixed solution (2).

Under stirring, (2) was slowly added to (1), followed by thorough stirring to obtain a clear solution. Injection needle-compatible activated carbon was added at 0.1 w/v %, followed by stirring for 15 min to allow adsorption, then the carbon was removed by filtration, the pH was adjusted to 6.8, and a volume of water for injection was added to make up the total volume required for the formulation, followed by thorough stirring. The mixture was filtered through a 0.22 Lm filter, and then fed into a 30 ml penicillin bottle at 10 ml/bottle. The bottle was loosely plugged, and pre-frozen in a lyophilizer.

The partition board was cooled to a temperature of −35° C. or lower which was maintained for 2 h. Then the chamber was cooled to −50° C. or lower and vacuumed to 20 Pa or lower. The limited leakage valve was open to allow the temperature to rise to −5° C. over 5 h which was maintained for further 10 h, then rise to 10° C. over 4 h which was maintained until the temperature of the product reached 0° C. or higher, and rise to 35° C. over 3 h which was maintained until the temperature of the product reached 25° C. or higher. Then the limited leakage valve was closed, and the temperature was maintained for 2 h. The plug is tightened up by charging N₂ in a vacuum, and the bottle is taken out of the lyophilizer and capped by pressing.

Example 63

Prescription

| | |
|---|---|
| Compound 5 | 10 g |
| Solutol HS 15 | 60 g |
| Propylene glycol | 10 g |
| Mannitol | 120 g |
| BHA | 0.1 |
| BHT | 0.1 |
| Sodium hydroxide or hydrochloric acid | appropriate amount |
| Water for injection, added up to | 1000 ml |

Prescribed amounts of Compound 5, Solutol HS 15 (from BASF, Germany), BHA (from Sichuan Haisco Pharmaceutical Co., Ltd.) and BHT (from Sichuan Haisco Pharmaceutical Co., Ltd.), at a temperature controlled at 65° C. to 70° C., were dissolved and thoroughly mixed to obtain Mixed solution (1).

Prescribed amounts of propylene glycol (from Hunan ER-KANG Pharmaceutical Co. Ltd.) and mannitol (from Guangxi Nanning Chemical Pharmaceutical Co. Ltd.) were added to a volume of water for rejection which was 60% of the total water volume required for the formulation, to obtain Mixed solution (2).

Under stirring, (2) was slowly added to (1), followed by thorough stirring to obtain a clear solution. Injection needle-compatible activated carbon was added at 0.1 w/v %, followed by stirring for 15 min to allow adsorption, then the carbon was removed by filtration, the pH was adjusted to 5.5, and a volume of water for injection was added to make up the total volume required for the formulation, followed by thorough stirring. The mixture was filtered through a 0.22 μm filter, and then fed into a 30 ml penicillin bottle at 10 ml/bottle. The bottle was loosely plugged, and pre-frozen in a lyophilizer.

The partition board was cooled to a temperature of −35° C. or lower which was maintained for 2 h. Then the chamber was cooled to −50° C. or lower and vacuumed to 20 Pa or lower. The limited leakage valve was open to allow the temperature to rise to −8° C. over 4 h which was maintained for further 10 h, then rise to 5° C. over 6 h which was maintained until the temperature of the product reached 0° C. or higher, and rise to 35° C. over 3 h which was maintained until the temperature of the product reached 25° C. or higher. Then the limited leakage valve was closed, and the temperature was maintained for 2 h. The plug is tightened up by charging N₂ in a vacuum, and the bottle is taken out of the lyophilizer and capped by pressing.

Example 64

Prescription

| | |
|---|---|
| Compound 6 | 15 g |
| Solutol HS 15 | 70 g |
| Propylene glycol | 15 g |
| Mannitol | 120 g |
| BHA | 0.1 |
| BHT | 0.1 |
| Sodium hydroxide or hydrochloric acid | appropriate amount |
| Water for injection, added up to | 1000 ml |

Prescribed amounts of Compound 6, Solutol HS 15 (from BASF, Germany), BHA (from Sichuan Haisco Pharmaceutical Co., Ltd.) and BHT (from Sichuan Haisco Pharmaceutical Co., Ltd.), at a temperature controlled at 65° C. to 70° C., were dissolved and thoroughly mixed to obtain Mixed solution (1).

Prescribed amounts of propylene glycol (from Hunan ER-KANG Pharmaceutical Co. Ltd.) and mannitol (from Guangxi Nanning Chemical Pharmaceutical Co. Ltd.) were added to a volume of water for rejection which was 60% of the total water volume required for the formulation, to obtain Mixed solution (2).

Under stirring, (2) was slowly added to (1), followed by thorough stirring to obtain a clear solution. Injection needle-compatible activated carbon was added at 0.1 w/v %, followed by stirring for 15 min to allow adsorption, then the carbon was removed by filtration, the pH was adjusted to 7.8, and a volume of water for injection was added to make up the total volume required for the formulation, followed by thorough stirring. The mixture was filtered through a 0.22 μm filter, and then fed into a 30 ml penicillin bottle at 10 ml/bottle. The bottle was loosely plugged, and pre-frozen in a lyophilizer.

The partition board was cooled to a temperature of −35° C. or lower which was maintained for 2 h. Then the chamber was cooled to −50° C. or lower and vacuumed to 20 Pa or lower. The limited leakage valve was open to allow the temperature to rise to −8° C. over 4 h which was maintained for further 10 h, then rise to 5° C. over 6 h which was maintained until the temperature of the product reached 0° C. or higher, and rise to 35° C. over 3 h which was maintained until the temperature of the product reached 25° C. or higher. Then the limited leakage valve was closed, and the temperature was maintained for 2 h. The plug is tightened up by charging N₂ in a vacuum, and the bottle is taken out of the lyophilizer and capped by pressing.

The samples of the following examples were prepared according to the method of Examples 20 to 27.

| Ingredients | Example 65 | Example 66 | Example 67 | Example 68 | Example 69 |
|---|---|---|---|---|---|
| Active ingredient | 2 g<br>Compound 5 | 10 g<br>Compound 10 | 20 g<br>Compound 5 | 20 g<br>Compound 13 | 2 g<br>Compound 16 |
| Soybean oil | 50 g | — | 100 g | 100 g | 50 g |
| Medium-chain triglyceride | 50 g | 100 g | 100 g | 100 g | — |
| Egg-yolk lecithin | 6 g | 12 g | 12 g | 12 g | 6 g |
| Glycerol | 22.5 g | 22.5 g | 25 g | 25 g | 22.5 g |
| Oleic acid | — | — | 0.4 g | — | — |
| Sodium oleate | — | 0.3 g | — | 0.3 g | — |

-continued

| Ingredients | Example 65 | Example 66 | Example 67 | Example 68 | Example 69 |
|---|---|---|---|---|---|
| Sodium hydroxide | Aqueous phase pH adjusted to 10.8 | Aqueous phase pH adjusted to 9.6 | Aqueous phase pH adjusted to 9.7 | Aqueous phase pH adjusted to 10.4 | Aqueous phase pH adjusted to 10.2 |
| Water for injection, added up to | 1000 ml | 1000 ml | 1000 ml | 1000 ml | 1000 ml |

The samples of the following examples were prepared according to the method of Examples 28 to 35.

| Ingredients | Example 70 | Example 65 | Example 71 | Example 72 | Example 73 |
|---|---|---|---|---|---|
| Active ingredient | 0.1 g Compound 14 | 20 g Compound 6 | 30 g Compound 9 | 10 g Compound 17 | 5 g Compound 11 |
| Solutol HS 15 | — | 80 g | 200 g | — | 50 g |
| Tween-80 | 1 g | — | — | 50 g | — |
| Tween-20 | — | — | — | 5 g | — |
| Ethanol | 1 g | — | — | 100 g | — |
| Propylene glycol | — | 100 g | 300 g | — | 100 g |
| BHA | 0.1 | 0.1 | 0.2 | — | — |
| BHT | 0.1 | 0.1 | 0.1 | — | — |
| EDTA-2Na | — | 0.1 | — | 0.2 | 0.1 |
| Sodium hydroxide or hydrochloric acid | pH adjusted to 5.5 | pH adjusted to 6.7 | pH adjusted to 8.2 | pH adjusted to 5.9 | pH adjusted to 7.5 |
| Water for injection, added up to | 1000 ml | 1000 ml | 1000 ml | 1000 ml | 1000 ml |

Example 74

Measurement of the Free API Concentration in the Aqueous Phase of the Formulations According to the Present Invention A propofol fat emulsion (a commercial product) and a compound according to the present invention were each placed in a Millipore Ultra-4 ultrafiltration tube (Cut-off molecular weight: 3000) and centrifuged for 15 min at 25° C. The lower aqueous layer was taken for concentration measurement which was performed in triplicate, and the results were averaged and shown in Table 1.

Table 1. Results of the Free API Concentration in the Aqueous Phase of the

| Compound | Free API concentration in the aqueous phase, μg/mL |
|---|---|
| Propofol fat emulsion (10 mg/mL) | 2.20 |
| Example 21 (10 mg/mL) | 0.95 |

Conclusion: The aqueous phase concentration of the Example was 2 to 3 times lower than that of the propofol fat emulsion, and is expected to reduce pain during injection and improve patient compliance.

Example 75

Stability Test of Formulations According to the Present Invention

Example 19 was left at 30° C.±2° C., RH 65%+5% for 6 months, and then tested. The results are shown in Table 2.

TABLE 2

| Results of stability test of formulations according to the present invention | | |
|---|---|---|
| Time (months) | 0 | 6 |
| Appearance | White uniform emulsion | White uniform emulsion |
| pH | 8.28 | 7.66 |
| Average particle diameter (nm) | 227.6 | 214.8 |
| Isomer (%) | 0.10 | 0.10 |
| Unknown most abundant impurity (%) | Not detected | Not detected |
| Total impurities (%) | 0.27 | 0.32 |
| Content (%) | 103.60 | 100.55 |

Example 76

Biological Experiments

1. Righting Reflex Experiment on Mice

SPF-grade ICR mice (SCXY(Sichuan)-2008-24, Chengdu Dashuo Bioscience&Tech Co. Ltd.), each weighing 18 to 22 g, half male and half female, were used. A well-established mouse anesthesia model was used to study the general anesthetic effect of the test compounds (Ratnakumari Lingamaneni, et al., (2001) Anesthesiology, 2001, 94, 1050-7). Indicators such as median effective dose ($ED_{50}$), median lethal dose ($LD_{50}$), therapeutic index (TI, i.e. $LD_{50}/ED_{50}$), safety index (SI, i.e. $LD_5/ED_{95}$), anesthesia induction time, anesthesia maintenance time, and maximum tolerated dose (MTD) were used to evaluate the effect and safety of anesthesia. A desired concentration of the compound to be tested was formulated with a solvent of 10% DMSO, 15% solutol HS15 and 75% saline, for further use. After adapting to the laboratory environment, laboratory animals were fasted for 12 hours. On the next day, administration was carried out at 10 mg/kg body weight. Upon intravenous injection, the time of loss of the righting reflex was recorded. The period from finishing of drug administration until loss of the righting reflex was recorded as the anesthesia induction time, and the period from loss of the righting reflex until recovery of the righting reflex was recorded as the anesthesia maintenance time. The anesthesia induction time and the anesthesia maintenance time were used to indicate how strong an anesthetic effect was. Meanwhile, the dose required to cause a 7-min anesthesia ($HD_7$) was measured and used to evaluate relative efficacy.

The experimental results are shown in Tables 3 and 4.

TABLE 3

Data from righting reflex experiment on mice

| Compound No. | $ED_{50}$ (mg/kg) | $LD_{50}$ (mg/kg) | TI | SI | Anesthesia induction time (s) | Anesthesia maintenance time (s) | MTD (mg/kg) |
| --- | --- | --- | --- | --- | --- | --- | --- |
| Propofol | 11.7 | 31.3 | 2.7 | 1.5 | <15.0 s | 652.5 | 20.0 |
| 1 | 3.7 | 22.7 | 6.1 | 1.7 | <15.0 s | 660.4 | 10.0 |
| 2 | 4.5 | 38.1 | 8.4 | 2.6 | <15.0 s | 901.7 | 25.0 |
| 3 | 7.1 | 40.0 | 5.7 | 2.7 | <15.0 s | 958.0 | 30.0 |
| 4 | 3.6 | 20.0 | 5.5 | 3.0 | <15.0 s | 554.4 | 10.0 |
| 5 | 6.6 | 38.2 | 5.8 | 3.7 | <15.0 s | 2235.6 | 35.0 |
| 6 | 46.1 | 107.3 | 2.3 | 1.1 | <15.0 s | 485.8 | 70.0 |
| 7 | 1.5 | 9.9 | 6.7 | 4.1 | <15.0 s | 631.9 | 6.0 |
| 8 | 5.8 | 43.6 | 7.5 | 3.5 | <15.0 s | 1031.6 | 20.0 |
| 10 | 1.5 | 6.3 | 4.1 | 3.8 | <15.0 s | 754.4 | 5.0 |
| 11 | 15.7 | 150.0 | 9.6 | 4.4 | <15.0 s | 1207.7 | 90.0 |
| 13 | 2.0 | 14.3 | 7.1 | 4.6 | <15.0 s | 1048.0 | 10.0 |
| 14 | 1.3 | 8.3 | 6.4 | 2.4 | <15.0 s | 690.0 | 4.0 |
| 16 | 5.3 | 36.8 | 6.9 | 3.0 | <15.0 s | 885.9 | 15.0 |
| 17 | 10.1 | 65.4 | 6.4 | 3.7 | <15.0 s | 1149.5 | 40.0 |

Conclusions: as compared to propofol, the compounds according to the present invention showed higher therapeutic index and safety index, and a broader therapeutic window. Most of the compounds of the present invention have an $ED_{50}$ value less than that of propofol, indicating that these test compounds have a lower minimum effective dose and higher activity than propofol.

TABLE 4

Comparison of $HD_7$ between the test compounds and propofol.

| Compound No. | $HD_7$ (mg/kg) |
| --- | --- |
| Propofol | 14.0 |
| 1 | 6.0 |
| 2 | 4.0 |
| 4 | 7.0 |
| 7 | 3.5 |
| 9 | 2.5 |
| 13 | 4.0 |
| 14 | 2.5 |
| 16 | 8.0 |

Conclusions: the compounds according to the present invention require a significantly lower dose of propofol to produce the same anesthetic effect.

2. Righting Reflex Experiment on Mice with Prodrugs

SPF-grade ICR mice (SCXY(Sichuan)-2008-24, Chengdu Dashuo Bioscience&Tech Co. Ltd.), each weighing 18 to 22 g, half male and half female, were used. A well-established mouse anesthesia model was used to study the general anesthetic effect of the test compounds (Ratnakumari Lingamaneni, et al., (2001) Anesthesiology, 2001, 94, 1050-7). A desired concentration of the compound to be tested was formulated with physiological saline, for further use. After adapting to the laboratory environment, the SPF-grade ICR mice were fasted for 12 hours. On the next day, administration was carried out at 10 mg/kg body weight. Upon intravenous injection, the time of loss of the righting reflex was recorded. The period from finishing of drug administration until loss of the righting reflex was recorded as the anesthesia induction time, and the period from loss of the righting reflex until recovery of the righting reflex was recorded as the anesthesia maintenance time. The anesthesia induction time and the anesthesia maintenance time were used to indicate how strong an anesthetic effect was. Indicators such as median effective dose ($ED_{50}$), median lethal dose ($LD_{50}$), therapeutic index (TI, i.e. $LD_{50}/ED_{50}$), safety index (SI, i.e. $LD_5/ED_{95}$), anesthesia induction time, anesthesia maintenance time, and maximum tolerated dose (MTD) were used to evaluate the effect and safety of anesthesia.

The experimental results are shown in Table 5.

TABLE 5

Data from righting reflex experiment on mice with prodrugs

| Compound No. | $ED_{50}$ (mg/kg) | $LD_{50}$ (mg/kg) | TI | SI | Anesthesia induction time (s) | Anesthesia maintenance time (s) | MTD (mg/kg) |
|---|---|---|---|---|---|---|---|
| Propofol | 11.7 | 31.3 | 2.7 | 1.5 | <15.0 | 652.5 | 20.0 |
| 18 | 20.4 | 86.2 | 4.2 | 3.3 | 73.0 | 1830.2 | 60.0 |

Conclusions: in the experiment, all the prodrug compounds according to the present invention can be dissolved in physiological saline and administered, thereby preventing potential bacterial infection that could have been easily caused by use of lipid emulsion. The experimental results demonstrate that the prodrugs showed improved solubility in water, can be metabolized in vivo into the active form, and showed a strong anesthetic effect on mice.

3. Righting Reflex Experiment on Rats with Emulsion Injections of Compounds 7 and 8

Test Agents:

Emulsion injection of Compound 7 was a white uniform emulsion liquid provided according to Example 21. Emulsion injection of Compound 8 was a white uniform emulsion liquid provided according to Example 52. Emulsion injection of propofol with medium/long chain fat was the product 16FM0187 (50 ml, 0.5 g) from Fresennius Kabi GmnH, distributed by Fresenius Kabi (Beijing). A 0.9% solution of sodium chloride: M13060623, produced by Sichuan Kelun Pharmaceutical Co. Ltd.

SPF grade SD rats (SCKX (Beijing) 2012-0001, Beijing Vital River Laboratory Animal Technology Co., Ltd.), each weighing 180 to 220 g, half male and half female, were used. After having been fasted for 16 h, the SPF grade SD rats were dosed via their tail veins, wherein the doses of Emulsion injection of Compound 7 were 0.5, 0.75, 1.0, 2.0, 4.0, 6.0, 8.0, 10.0, 15.0 ml/kg, the doses of Emulsion injection of Compound 8 were 5.0, 6.0, 7.0, 10.0, 15.0, 20.0, 30.0, 40.0, 50.0, 60.0 mg/kg, and the doses of Emulsion injection of propofol with medium/long chain fat were 2.5, 5.0, 7.5, 10.0, 15.0, 20.0, 25.0, 30.0, 35.0, 40.0 mg/kg. A timer was started before the experiment, and the time of administration, the time of losing the righting reflex, the time of restoring the righting reflex, and the time till walking were recorded. Adverse effects shown by the rats after administration were also recorded.

Evaluation Indices:

Time of losing the righting reflex: the period from the finishing of the injection until the loss of the righting reflex, wherein a rat made lying on its back can maintain the lying state for a period of 60 s;

Time of maintaining the loss of the righting reflex: the period from the loss of the righting reflex until the recovery of the righting reflex, wherein a rat made lying on its back rights in less than 2 s (major index);

Time till walking: the period from the recovery of the righting reflex until occurrence of spontaneous forwarding moving and recovery of muscle tension of the limbs.

The dose required to cause 50% of the rats to lose the righting reflex ($HD_{50}$) and the dose required to effect 10-min anesthesia ($HD_{10\ min}$) were calculated from a non-linear fitting, and used to evaluate relative efficacy of compounds. The therapeutic index TI ($LD_{50}/HD_{50}$) was calculated to evaluate the safety window of compounds. The results are shown in Table 6.

TABLE 6

Efficacy and safety window of tested agents for loss of righting reflex (LORR) in rats

| Test group | $HD_{50}$ (mg/kg) | $LD_{50}$ (mg/kg) | TI | $HD_{10\ min}$ (mg/kg) |
|---|---|---|---|---|
| Emulsion injection of Compound 7 | 0.88 | 8.00 | 9.1 | 1.84 |
| Emulsion injection of Compound 8 | 5.97 | 53.67 | 9.0 | 8.90 |
| Emulsion injection of propofol with medium/long chain fat | 5.05 | 31.31 | 6.2 | 11.50 |

The results demonstrate that the Emulsion injection of Compound 7 showed better anesthetic efficacy than the Emulsion injection of Compound 8 and the Emulsion injection of propofol with medium/long chain fat, and showed a $HD_{50}$ of about ⅕ of that of the Emulsion injection of propofol with medium/long chain fat. $HD_{10\ min}$ of the Emulsion injection of Compound 7 was only ⅙ of that of the Emulsion injection of propofol with medium/long chain fat. Both the Emulsion injection of Compound 7 and the Emulsion injection of Compound 8 showed a better TI (therapeutic index) than the Emulsion injection of propofol with medium/long chain fat, indicating a better safety window.

4. Anesthetic Dose and Efficacy Experiments in Beagle Dogs

Test Agents:

Emulsion injection of Compound 7 was a white uniform emulsion liquid provided according to Example 21. Emulsion injection of propofol with medium/long chain fat was the product 16FM0187 (50 ml, 0.5 g) from Fresenius Kabi GmnH, distributed by Fresenius Kabi (Beijing). A 0.9% solution of sodium chloride: M13060623, produced by Sichuan Kelun Pharmaceutical Co. Ltd.

The experiment adopted a Latin square design. 6 normal-grade Beagle dogs (SCXK (Sichuan) 2013-24, Chengdu Dashuo Bioscience and Technology Co. Ltd.), each weighing 8 to 12 kg, half male and half female, were numbered and subjected to a 2 to 3-day cleaning period. Each Beagle dog was weighed before each experiment and given a different dose of drug in each experiment. After the experiment, each Beagle dog was sequentially given six different doses. In each experiment, each Beagle dog was fasted for 18 hours, and administered through forelimb cephalic veins (the injection took 60 to 80 seconds to finish), in which the doses of Emulsion injection of Compound 7 were 0.8 mg/kg (Low dose), 1.2 mg/kg (Medium dose), 2.5 mg/kg (High dose), and the doses of Emulsion injection of propofol with medium/long chain fat were 3.0 mg/kg (Low dose), 5.0 mg/kg (Medium dose), 10.0 mg/kg (High dose). A timer was started from 0:0 before each experiment, and the time of starting and finishing administration, the starting time of anesthesia, the starting time of waking-up, and time of starting walking were recorded in a minute:second format. And adverse effects of Beagle dogs after administration were also recorded.

Evaluation Indices:

Time needed to take effect: the period from the time of starting the injection into a Beagle dog until the time of the Beagle dog starting lowering its head and closing its eyelids;

Duration of anesthesia: the period from the time of the Beagle dog lowering its head and closing its eyelids until the time of the Beagle dog starting waking up (for example, opening the eyes, raising the head) (major index);

Time till walking: the period from the time of the Beagle dog starting waking up until the time when it can walk.

The average values and standard deviations of the Time needed to take effect, Duration of anesthesia, and the Time till walking for each dose were calculated and expressed in Average±SD. And a T-test was made for the Time needed to take effect, Duration of anesthesia, and the Time till walking under the same anesthesia degree caused by the Emulsion injection of Compound 7 and the Emulsion injection of propofol with medium/long chain fat. The results are shown in Table 7.

mg/kg (Medium dose), 2.0 mg/kg (High dose), and doses of Emulsion injection of propofol with medium/long chain fat were 3.0 mg/kg (Low dose), 5.0 mg/kg (Medium dose), 10.0 mg/kg (High dose). A timer was started before each experiment, and the time of starting and finishing administration, the starting time of anesthesia, the starting time of waking-up, and time of starting walking were recorded. And adverse effects of minipigs after administration were also recorded.

Evaluation Indices:

Time needed to take effect: the period from the time of starting injection into a minipig until the time of the minipig starting lowering its head and closing its eyelids;

Duration of anesthesia: the period from the time of the minipig lowering its head and closing its eyelids until the time of the minipig starting waking up (for example, opening the eyes, raising the head) (major index);

Time till walking: the period from the time of the minipig starting waking up until the time when it can walk.

The average values and standard deviations of the Time needed to take effect, Duration of anesthesia, and the Time till walking for each dose were calculated and expressed in Average±SD. And a T-test was made for the Time needed to take effect, Duration of anesthesia, and the Time till walking

TABLE 7

Efficacy of Emulsion injection of Compound 7 and Emulsion injection of propofol with medium/long chain fat in Beagle dogs

|  | Emulsion injection of Compound 7 | | | Emulsion injection of propofol with medium/long chain fat | | |
| --- | --- | --- | --- | --- | --- | --- |
| Dose (mg/kg) | 0.8 | 1.2 | 2.5 | 3.0 | 5.0 | 10.0 |
| Time needed to take effect (min) | 1.33 ± 0.42 | 1.04 ± 0.26 | 0.77 ± 0.35 | 1.49 ± 0.35 | 1.04 ± 0.38 | 0.64 ± 0.13 |
| Duration of anesthesia (min) | 7.09 ± 3.41 | 13.14 ± 7.02 | 28.14 ± 5.26 | 6.40 ± 3.01 | 14.29 ± 5.43 | 23.59 ± 8.93 |
| Time till walking (min) | 3.06 ± 2.43 | 2.13 ± 2.89 | 1.05 ± 0.38 | 3.17 ± 3.18 | 1.93 ± 1.91 | 2.59 ± 2.73 |

Conclusion: Both the Emulsion injection of Compound 7 and the Emulsion injection of propofol with medium/long chain fat showed a dose-dependent anesthetic effect. The Time needed to take effect, Duration of anesthesia, and the Time till walking resulting from the three doses of the Emulsion injection of Compound 7 showed no statistic difference from the three doses of the Emulsion injection of propofol with medium/long chain fat, but the Emulsion injection of Compound 7 showed a lower dose, which was about ¼ of the dose of the Emulsion injection of propofol with medium/long chain fat, required to achieve the same efficacy.

5. Anesthetic Dose and Efficacy Experiments in Minipigs

Test Agents:

Emulsion injection of Compound 7 was a white uniform emulsion liquid provided according to Example 21. Emulsion injection of propofol with medium/long chain fat was the product 16FM0187 (50 ml, 0.5 g), a white uniform emulsion liquid from Fresennius Kabi GmnH, distributed by Fresenius Kabi (Beijing), which had been stored at 25° C. or lower in darkness without being frozen. Physiological saline: M13060623, produced by Sichuan Kelun Pharmaceutical Co. Ltd.

The experiment adopted a Latin square design. Four minipigs, half male and half female, were numbered, weighed before each experiment, and each given a different dose of drug in each experiment. After the experiment, each minipig was sequentially given six different doses. Before experiment, the minipigs were fasted for 18 hours, and administered through ear auricle veins (the injection took 80 to 120 seconds to finish), in which the doses of Emulsion injection of Compound 7 were 0.6 mg/kg (Low dose), 1.0 under the same anesthesia degree caused by the Emulsion injection of Compound 7 and the Emulsion injection of propofol with medium/long chain fat. The results are shown in Table 8.

The results show that both the Emulsion injection of Compound 7 and the Emulsion injection of propofol with medium/long chain fat showed a dose-dependent anesthetic effect. The Time needed to take effect, Duration of anesthesia, and the Time till walking resulting from the three doses of the Emulsion injection of Compound 7 showed no statistic difference from the three doses of the Emulsion injection of propofol with medium/long chain fat, except that the Duration of anesthesia of the low dose (0.6 mg/kg) of Compound 7 showed a statistically significant increase as compared to the low dose (3.0 mg/kg) of propofol. Furthermore, the Emulsion injection of Compound 7 showed a lower dose, which was about ⅕ of the dose of the Emulsion injection of propofol with medium/long chain fat, as required to achieve the same efficacy.

TABLE 8

Efficacy of Emulsion injection of Compound 7 and Emulsion injection of propofol with medium/long chain fat in minipigs

| | Emulsion injection of Compound 7 | | | Emulsion injection of propofol with medium/long chain fat | | |
|---|---|---|---|---|---|---|
| Dose (mg/kg) | 0.6 | 1.0 | 2.0 | 3.0 | 5.0 | 10.0 |
| Time needed to take effect (min) | 2.15 ± 0.75 | 1.33 ± 0.38 | 0.90 ± 0.39 | 1.32 ± 0.83 | 1.44 ± 0.24 | 0.90 ± 0.10 |
| Duration of anesthesia (min) | 10.81 ± 1.47* | 19.62 ± 4.31 | 48.56 ± 7.45 | 6.59 ± 2.99* | 18.75 ± 5.29 | 40.73 ± 6.74 |
| Time till walking (min) | 3.25 ± 3.66 | 3.84 ± 5.48 | 5.12 ± 3.35 | 6.23 ± 4.31 | 8.53 ± 7.95 | 7.62 ± 6.85 |

*indicating that the duration of anesthesia of the low dose (0.6 mg/kg) of Compound 7 showed a statistically significant increase as compared to the low dose (3.0 mg/kg) of propofol, P < 0.05.

6. Preliminary Pharmacodynamic Studies with Healthy Humans

Experimental Procedure:

42 healthy male volunteers were randomized into 8 groups, and randomly administered according to the table below: Groups 1 and 2 were randomly administrated by single intravenous injections with the Emulsion injection of Compound 7 or a placebo, wherein the first subject in Groups 1 and 2 was given Compound 7 and the rest of subjects was subjected to a double-blind test; Groups 3-8 were randomly administered, in an opened manner, by single intravenous injections with the Emulsion injection of Compound 7 or the Emulsion injection of propofol with medium/long chain fat.

TABLE 9

Studies of dose of Compound 7

| Group | Number of subjects per group (Number on test drug: Number on control*) | Dose of Compound 7 (mg/kg) | Placebo (mL/kg) | Dose of propofol (mg/kg) |
|---|---|---|---|---|
| 1 | 3 (2:1) | 0.016 | 0.0016 | — |
| 2 | 3 (2:1) | 0.064 | 0.0064 | — |
| 3 | 6 (5:1) | 0.128 | — | 2.5 |
| 4 | 6 (5:1) | 0.192 | — | 2.5 |
| 5 | 6 (5:1) | 0.288 | — | 2.5 |
| 6 | 6 (5:1) | 0.432 | — | 2.5 |
| 7 | 6 (5:1) | 0.648 | — | 2.5 |
| 8 | 6 (5:1) | 0.972 | — | 2.5 |

*Number on test drug: the number of subjects who were given the Emulsion injection of Compound 7 which was produced by the method of Example 21.
Number on control: the number of subjects who were given the Emulsion injection of propofol with medium/long chain fat (Fresofol 1% MCT/LCT propofol) or a placebo, wherein the placebo was the other ingredients in the Emulsion injection of Compound 7 excluding the active ingredient, and was prepared by the same method as that for the Emulsion injection of Compound 7.

The subjects were fasted during the night for 6 hours or longer. The Emulsion injection of Compound 7 was administered by single intravenous injection. Groups 1 and 2 were administered by manual push injection for 2 to 3 seconds, and Groups 3-8 were administered by constant-rate pump injection for more than 1 min.

Pharmacodynamics Indices:

Primary indices include RASS and the tolerance to pain during injection (Verbal rating scale (VRS) was used to allow the researchers to know the pain degree of subjects); and secondary indices include cardiovascular indices and EEG (electroencephalogram) and BIS (Bispectral index) associated with the cognitive function recovery evaluation (QoR-40).

Experimental Results:

With the dose of 0.128 mg/kg of Compound 7, subjects started showing light anesthesia; and a dose of Compound 7 ⅓ to ⅕ of the dose of propofol produced the same anesthetic effect as the propofol.

The basic principle and major characteristics and advantages of the present invention have been shown and described above. A person skilled in the art should understand that the present invention is not limited to the above examples. The above Examples and descriptions in the specification only serve to explain the principle of the present invention, and various modifications and improvements can be made to the present invention without departing from the spirit and scope of the present invention, and are also within the scope of the present invention. The scope of the present invention is defined by the claims and their equivalence.

The pharmaceutical formulations according to the present invention can be produced in a large scale, are stable products having excellent safety, and can be used as anesthetics, sedatives, or the like.

That which is claimed is:

1. A pharmaceutical formulation comprising an active ingredient in an amount of 0.01 w/v % to 5 w/v %, wherein the active ingredient is a compound of general formula (I), or a stereoisomer, a pharmaceutically acceptable salt, or a prodrug thereof,

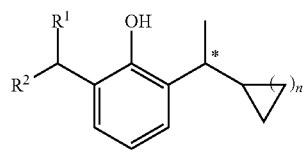

(I)

wherein $R^1$ and $R^2$ are each independently selected from a $C_{1-4}$ alkyl or a $C_{3-6}$ cycloalkyl and n is 1 or 2, and wherein the prodrug of the compound of general formula (I) is selected from compounds of general formula (II),

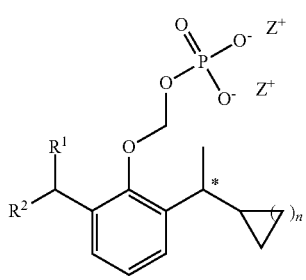

wherein Z⁺ is each independently selected from H⁺, Na⁺ or K⁺.

2. The pharmaceutical formulation according to claim 1, wherein R¹ is selected from methyl, ethyl or isopropyl, and wherein R² is selected from methyl, ethyl, isopropyl or cyclopropyl.

3. The pharmaceutical formulation according to claim 2, wherein the compound of general formula (I) is selected from

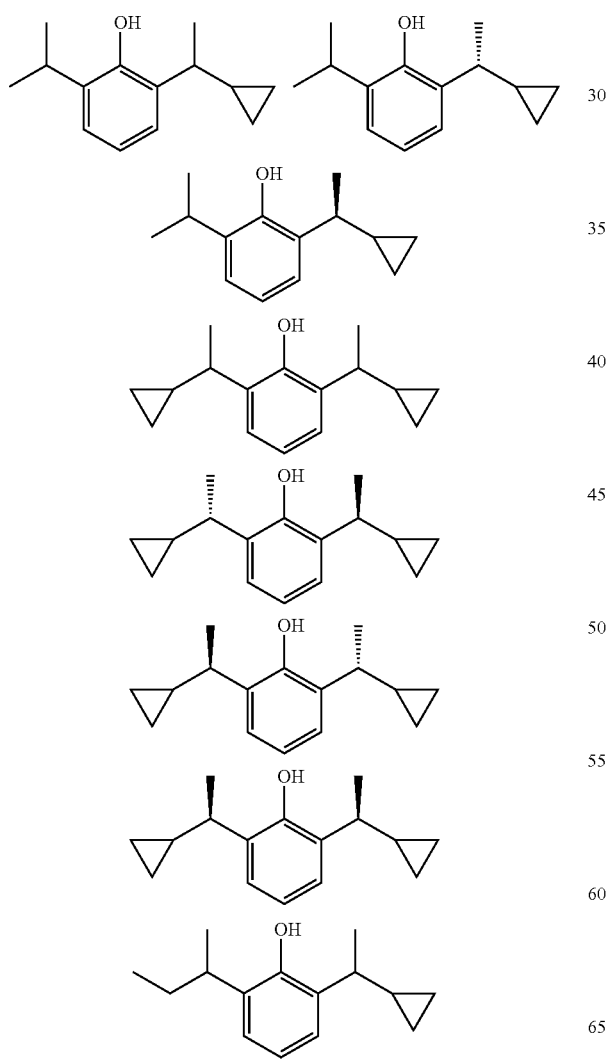

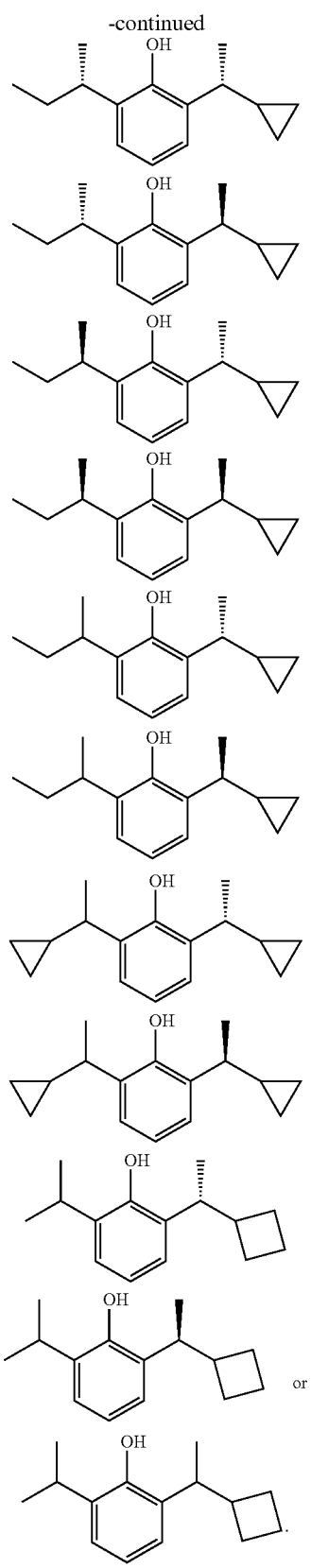

4. The pharmaceutical formulation according to claim 3, wherein the compound of general formula (I) is selected from

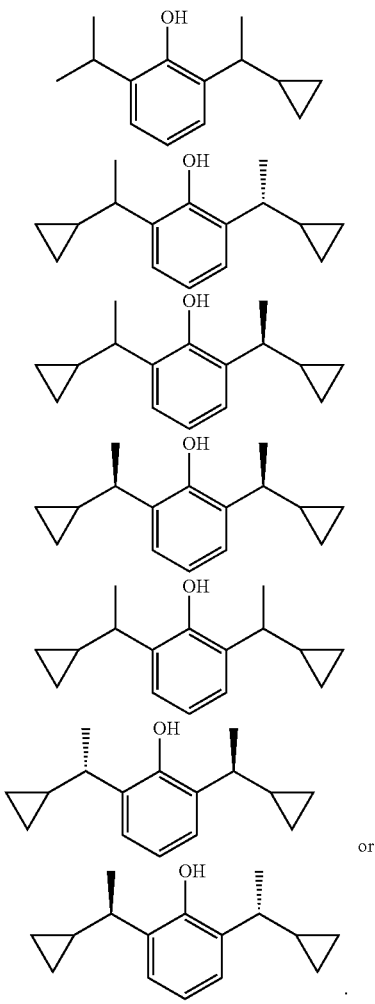

5. The pharmaceutical formulation according to claim 1, wherein the pharmaceutical formulation is an aqueous solution, further comprising:
a solubilizing agent in an amount of 0.1 w/v % to 20 w/v %; and
a co-solvent in an amount of 0 w/v % to 30 w/v %.

6. The pharmaceutical formulation according to claim 5, wherein the active ingredient is in an amount 0.05 w/v % to 3 w/v %, and wherein the pharmaceutical formulation further comprises
a solubilizing agent in an amount of 0.1 w/v % to 15 w/v %; and
a co-solvent in an amount of 0.1 w/v % to 20 w/v %.

7. The pharmaceutical formulation according to claim 6, wherein the active ingredient is in an amount of 0.1 w/v % to 2 w/v %, the solubilizing agent is in an amount of 0.2 w/v % to 10 w/v %, and the co-solvent is in an amount of 0.1 w/v % to 10 w/v %.

8. The pharmaceutical formulation according to claim 7, wherein the solubilizing agent is selected from the group consisting of one or more of Tween-80, Tween-20, PEG-35 castor oil, PEG-40 hydrogenated castor oil, PEG-15 hydroxystearate and poloxamer, and wherein the co-solvent is selected from the group consisting of one or more of ethanol, glycerol, propylene glycol and PEG.

9. The pharmaceutical formulation according to claim 1, wherein
the active ingredient is in an amount of 0.01 w/v % to 5 w/v % and wherein the pharmaceutical formulation further comprises a solubilizing agent in an amount of 0.1 w/v % to 20 w/v %;
a co-solvent in an amount of 0 w/v % to 30 w/v %; and
a filler in an amount of 1 w/v % to 30 w/v %.

10. The pharmaceutical formulation according to claim 9, wherein the active ingredient is in an amount of 0.05 w/v % to 3 w/v %,
the solubilizing agent is in an amount of 0.1 w/v % to 15 w/v %,
the co-solvent is in an amount of 0.1 w/v % to 20 w/v %, and
the filler is in an amount of 3 w/v % to 15 w/v %.

11. The pharmaceutical formulation according to claim 10, wherein the active ingredient is in an amount of 0.1 w/v % to 2 w/v %, the solubilizing agent is in an amount of 0.2 w/v % to 10 w/v %, the co-solvent is in an amount of 0.1 w/v % to 10 w/v %, and the filler is in an amount of 5 w/v % to 10 w/v %.

12. The pharmaceutical formulation according to claim 9, wherein a solution for the pharmaceutical formulation is further lyophilized after being prepared.

13. The pharmaceutical formulation according to claim 12, wherein the solubilizing agent is selected from the group consisting of one or more of Tween-80, Tween-20, PEG-35 castor oil, PEG-40 hydrogenated castor oil, PEG-15 hydroxystearate and poloxamer, wherein
the co-solvent is selected from the group consisting of one or more of ethanol, glycerol, propylene glycol and PEG, and
wherein the filler is selected from the group consisting of one or more of lactose, sucrose, glucose, mannitol, sodium dihydrophosphate, sodium phosphate, sodium chloride, disodium hydrogen phosphate, cysteine, glycine, sorbitol, calcium lactobionate, dextran and polyvinylpyrrolidone.

14. The pharmaceutical formulation according to claim 5, further comprising a pH-adjusting agent in an amount of 0 w/v % to 10 w/v %.

15. The pharmaceutical formulation according to claim 14, wherein the pH-adjusting agent is selected from the group consisting of one or more of sodium hydroxide, potassium hydroxide, triethanolamine, hydrochloric acid, phosphoric acid, and citric acid.

16. The pharmaceutical formulation according to claim 15, further comprising an iso-osmotic adjusting agent in an amount of 0 w/v % to 5 w/v %.

17. The pharmaceutical formulation according to claim 16, wherein the iso-osmotic adjusting agent is selected from the group consisting of one or more of glycerol, sorbitol, propylene glycol, polyethylene glycol, and mannitol.

18. The pharmaceutical formulation according to claim 1, wherein the pharmaceutical formulation is a fat emulsion and further comprises
an oily component in an amount of 5 w/v % to 30 w/v %; and
an emulsifying agent in an amount of 0.5 w/v % to 5 w/v %.

19. The pharmaceutical formulation according to claim 18, wherein
the active ingredient is in an amount of 0.05 w/v % to 3 w/v %,
the oily component is in an amount of 5 w/v % to 20 w/v %, and
the emulsifying agent is in an amount of 0.5 w/v % to 3 w/v %.

20. The pharmaceutical formulation according to claim 19, wherein the active ingredient is in an amount of 0.1 w/v % to 2 w/v %,
the oily component is in an amount of 5 w/v % to 15 w/v %, and
the emulsifying agent is in an amount of 0.5 w/v % to 2 w/v %.

21. The pharmaceutical formulation according to claim 20, wherein the oily component is selected from the group consisting of one or more of soybean oil, olive oil, fish oil, linseed oil, medium chain triglycerides, and structural triglycerides, and wherein the emulsifying agent is selected from the group consisting of one or more of poloxamer, Tween-80, PEG-15 hydroxyl stearate, PEG-35 castor oil, PEG-40 hydrogenated castor oil, egg-yolk lecithin, and soybean lecithin.

22. The pharmaceutical formulation according to claim 21, further comprising a co-emulsifying agent in an amount of 0 to 0.2 w/v %.

23. The pharmaceutical formulation according to claim 22, wherein the co-emulsifying agent is selected from the group consisting of one or more of oleic acid and sodium oleate.

24. The pharmaceutical formulation according to claim 23, further comprising an iso-osmotic adjusting agent in an amount of 0 w/v % to 5 w/v %.

25. The pharmaceutical formulation according to claim 24, wherein the iso-osmotic adjusting agent is selected from the group consisting of one or more of glycerol, sorbitol, propylene glycol, polyethylene glycol, and mannitol.

26. The pharmaceutical formulation according to claim 25, wherein the active ingredient is in an amount of 0.1 w/v % to 2 w/v %, and wherein the pharmaceutical formulation further comprises:
one of, or a mixture in any ratio of both of, soybean oil and medium chain triglycerides, in an amount of 5 w/v % to 15 w/v %;
egg-yolk lecithin in an amount of 0.5 w/v % to 2 w/v %;
glycerol in an amount of 0 w/v % to 5 w/v %; and
sodium oleate in an amount of 0 w/v % to 0.2 w/v %.

27. The pharmaceutical formulation according to claim 26, wherein the pharmaceutical formulation has a pH selected from the group consisting of 3.0 to 10.0, 4.0 to 9.0, and 6.0 to 9.0.

28. A method for inducing or maintaining general anesthesia or sedation in a mammal, comprising administering to the mammal an effective dose of a compound of general formula (I), or a stereoisomer, a pharmaceutically acceptable salt, or a prodrug thereof, wherein the effective dose is a loading dose and/or a maintenance dose, wherein the loading dose of the compound of general formula (I) is 0.01 mg/kg to 15.0 mg/kg, the maintenance dose of the compound of general formula (I) is 0.01 mg/(kg·h) to 20.0 mg/(kg·h), and the loading dose of the prodrug of the compound of general formula (I) is 0.1 mg/kg to 30.0 mg/kg,

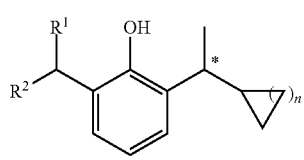
(I)

wherein $R^1$ and $R^2$ are each independently selected from a $C_{1-4}$ alkyl or a $C_{3-6}$ cycloalkyl and n is 1 or 2, and wherein the prodrug of the compound of general formula (I) is selected from compounds of general formula (II),

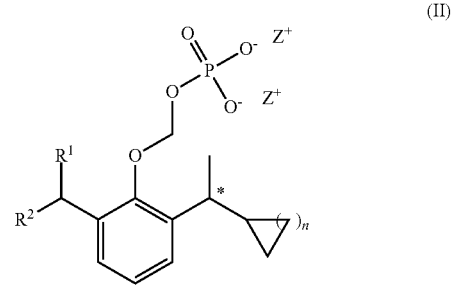
(II)

wherein $Z^+$ is each independently selected from $H^+$, $Na^+$ or $K^+$.

29. The method according to claim 28, wherein $R^1$ is selected from methyl, ethyl or isopropyl, and wherein $R^2$ is selected from methyl, ethyl, isopropyl or cyclopropyl.

30. The method according to claim 29, wherein the compound of general formula (I) is selected from

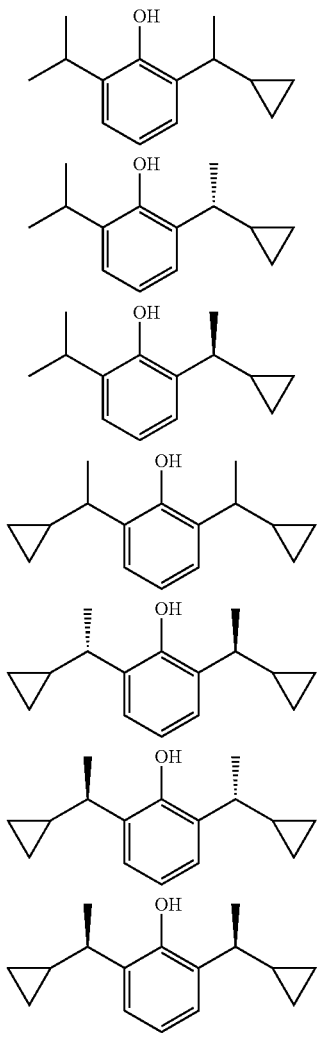

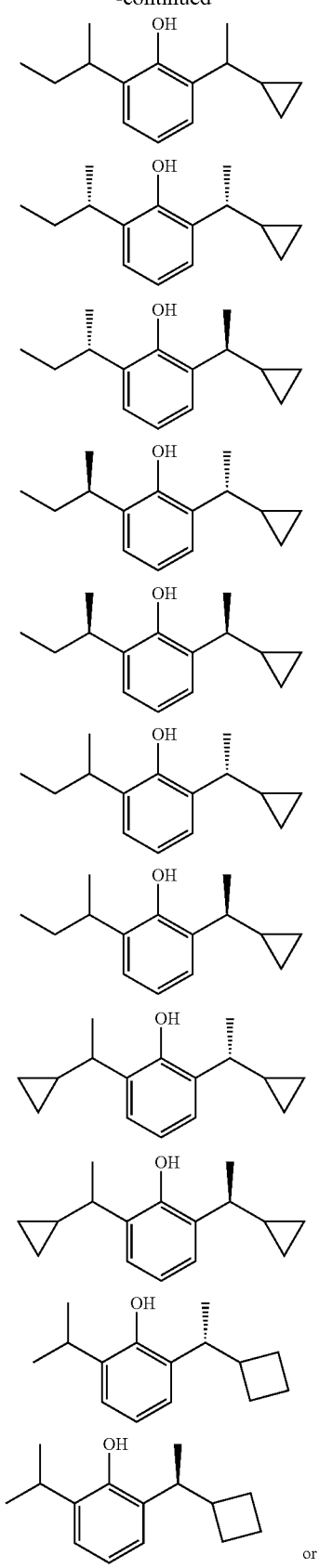

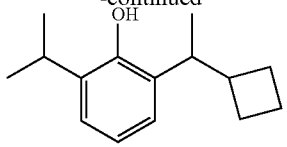

31. The method according to claim 28, wherein
the loading dose of the compound of general formula (I) is selected from a range of 0.05 mg/kg to 10.0 mg/kg, a range of 0.1 mg/kg to 10.0 mg/kg, a range of 0.1 mg/kg to 5.0 mg/kg, a range of 0.1 mg/kg to 2.0 mg/kg, or a range of 0.1 mg/kg to 1.0 mg/kg,
the loading dose of the prodrug of the compound of general formula (I) is selected from a range of 0.5 mg/kg to 15.0 mg/kg, a range of 1.0 mg/kg to 12.0 mg/kg, a range of 1.0 mg/kg to 10.0 mg/kg, a range of 1.0 mg/kg to 8.0 mg/kg, a range of 1.0 mg/kg to 6.0 mg/kg, or a range of 1.0 mg/kg to 5.0 mg/kg, and
the maintenance dose of the compound of general formula (I) is selected from a range of 0.01 mg/(kg·h) to 10.0 mg/(kg·h), a range of 0.02 mg/(kg·h) to 6.0 mg/(kg·h), a range of 0.05 mg/(kg·h) to 4.0 mg/(kg·h), a range of 0.1 mg/(kg·h) to 4.0 mg/(kg·h), a range of 0.1 mg/(kg·h) to 2.0 mg/(kg·h), or a range of 0.1 mg/(kg·h) to 1.0 mg/(kg·h).

32. The method according to claim 28, wherein the loading dose of the compound of general formula (I) or a prodrug thereof is administered over a period not longer than 10 min.

33. The method according to claim 32, wherein the loading dose of the compound of general formula (I) or a prodrug thereof is administered over a period not longer than 2 min.

34. The method according to claim 28, wherein the administering is performed by one or more of single administration, multiple administrations, continuous administration, and target-controlled infusion.

35. The method according to claim 28, wherein the administering is performed by a route selected from intravenous injection, intra-arterial injection, intramuscular injection, transdermal, buccal, parenteral intraperitoneal, rectal, transbuccal, intranasal, inhalation, topical, subcutaneous, intra-adipose, intra-articular, intraperitoneal, and intrathecal administrations.

36. The method according to claim 35, wherein the administering is performed by intravenous injection.

37. The method according to claim 28, further comprising:
concomitantly administering to the mammal one or more additional active ingredients other than the compound of general formula (I), wherein the additional active ingredients are selected from drugs having sedative hypnotic activity or anesthetic adjuvant drugs.

38. The method according to claim 37, wherein the additional active ingredients are selected from a γ-aminobutyric acid receptor agonist, a γ-aminobutyric acid receptor activator, an M-receptor antagonist, a $N_2$-receptor antagonist, 5-hydroxytryptophan 3 receptor antagonist, a $Na^+$ channel antagonist, or an opioid receptor agonist.

39. The method according to claim 38, wherein the additional active ingredients are selected from intravenous anesthetics, inhalation anesthetics, or anesthetic adjuvant agents.

40. The method according to claim 39, wherein the intravenous anesthetics are selected from propofol, fospropofol sodium, midazolam, ketamine, thiopental sodium, sodium oxybate, or etomidate, including pharmaceutically acceptable salts thereof;

the inhalation anesthetics are selected from sevoflurane, isoflurane, enflurane, desflurane, methoxyflurane, or nitrous oxide; and the anesthetic adjuvant agents are selected from sedative hypnotics, anticholinergics, muscle relaxants, antiemetics, local anesthetics, or analgesics.

41. The method according to claim 40, wherein the sedative hypnotics are selected from diazepam, flu-azepam, chlordiazepoxide, estazolam, clonazepam, glutethimide, meprobamate, buspirone, midazolam, dexmedetomidine, droperidol, promethazine, chlorpromazine, barbital, phenobarbital, pentobarbital, amobarbital, secobarbital or thiopental sodium, including pharmaceutically acceptable salts thereof;

the anticholinergics are selected from atropine or scopolamine, including pharmaceutically acceptable salts thereof;

the muscle relaxants are selected from vecuronium bromide, rocuronium bromide, pancuronium bromide, pipecuronium bromide, mivacurium chloride, atracurium or succinylcholine, including pharmaceutically acceptable salts thereof;

the antiemetics are selected from tropisetron, palonosetron, granisetron, dolasetron, scopolamine, cyclizine or metoclopramide, including pharmaceutically acceptable salts;

the local anesthetics are selected from lidocaine, ropivacaine, prilocaine, bupivacaine, articaine or dyclonine, including their pharmaceutically acceptable salts; and the analgesics are selected from fentanyl, remifentanil, sufentanil, alfentanil, morphine, pethidine, dezocine, butorphanol, oxycodone or nefopam, including their pharmaceutically acceptable salts.

42. A pharmaceutical composition provided as a liquid formulation or a lyophilized formulation, wherein the liquid formulation or lyophilized formulation comprises a compound of general formula (I), or a stereoisomer, a pharmaceutically acceptable salt, or a prodrug thereof, at a concentration in the liquid formulation or in a solution to be lyophilized into the lyophilized formulation of 0.1 mg/mL to 50.0 mg/mL,

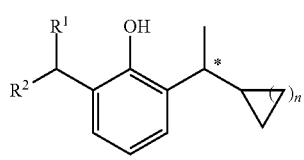

(I)

wherein $R^1$ and $R^2$ are each independently selected from a $C_{1-4}$ alkyl or a $C_{3-6}$ cycloalkyl and n is 1 or 2, and wherein the prodrug of the compound of general formula (I) is selected from compounds of general formula (II),

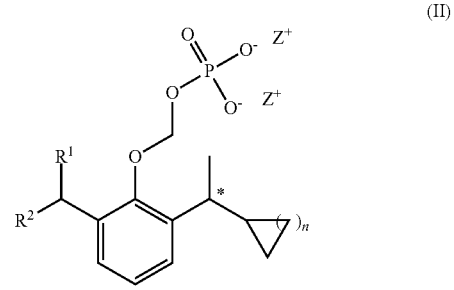

(II)

wherein $Z^+$ is each independently selected from $H^+$, $Na^+$ or $K^+$.

43. The pharmaceutical composition according to claim 42, wherein the concentration is selected from a range of 0.1 mg/mL to 40.0 mg/mL, a range of 0.5 mg/mL to 30.0 mg/mL, a range of 1.0 mg/mL to 20.0 mg/mL, or a range of 5.0 mg/mL to 20.0 mg/mL.

44. The pharmaceutical composition according to claim 42 or 43, wherein the liquid formulation or lyophilized formulation further comprises one or more additional active ingredients other than the compound of general formula (I), wherein the additional active ingredients are selected from drugs having sedative hypnotic activity or anesthetic adjuvant drugs.

45. The pharmaceutical composition according to claim 44, wherein the additional active ingredients are selected from a γ-aminobutyric acid receptor agonist, a γ-aminobutyric acid receptor activator, an M-receptor antagonist, a $N_2$-receptor antagonist, 5-hydroxytryptophan 3 receptor antagonist, a $Na^+$ channel antagonist, or an opium receptor agonist.

46. The pharmaceutical composition according to claim 44, wherein the additional active ingredients are selected from intravenous anesthetics or anesthetic adjuvant agents.

47. The pharmaceutical composition according to claim 46, wherein the intravenous anesthetics are selected from propofol, fospropofol sodium, midazolam, ketamine, thiopental sodium, sodium oxybate, or etomidate, including their pharmaceutically acceptable salts; and the anesthetic adjuvant agents are selected from sedative hypnotics, anticholinergics, muscle relaxants, antiemetics, local anesthetics, or analgesics.

48. The pharmaceutical composition according to claim 47, wherein the sedative hypnotics are selected form diazepam, flu-azepam, chlordiazepoxide, estazolam, clonazepam, glutethimide, meprobamate, buspirone, midazolam, dexmedetomidine, droperidol, promethazine, chlorpromazine, barbital, phenobarbital, pentobarbital, amobarbital, secobarbital or thiopental sodium, including their pharmaceutically acceptable salts;

the anticholinergics are selected from atropine or scopolamine, including their pharmaceutically acceptable salts;

the muscle relaxants are selected from vecuronium bromide, rocuronium bromide, pancuronium bromide, pipecuronium bromide, mivacurium chloride, atracurium or succinylcholine, including their pharmaceutically acceptable salts thereof;

the antiemetics are selected from tropisetron, palonosetron, granisetron, dolasetron, scopolamine, cyclizine or metoclopramide, including pharmaceutically acceptable salts thereof;

the local anesthetics are selected from lidocaine, ropivacaine, prilocaine, bupivacaine, articaine or dyclonine, including pharmaceutically acceptable salts thereof; and the analgesics are selected from fentanyl, remifentanil, sufentanil, alfentanil, morphine, pethidine, dezocine, butorphanol, oxycodone or nefopam, including pharmaceutically acceptable salts thereof.

49. The pharmaceutical composition according to claim 42, wherein the liquid formulation or lyophilized formulation is suitable for administration by intravenous injection.

50. The pharmaceutical composition according to claim 42, wherein the liquid formulation is an aqueous solution suitable for intravenous injection, or a fat emulsion suitable for intravenous injection.

51. A kit comprising: a single dose or multiple doses of the pharmaceutical composition according to claim 42, and a package insert showing information in one or more forms, wherein the information is selected from one or more indications for administration of the pharmaceutical composition, storage information and dosing information of the pharmaceutical composition, and instructions about how to administer the pharmaceutical composition.

52. An article comprising: a single dose or multiple doses of the pharmaceutical composition according to claim 42, and a packaging material.

53. The article according to claim 52, wherein the packaging material comprises one or more containers for accommodating the single dose or multiple doses of the pharmaceutical composition.

54. The article according to claim 52, wherein the one or more containers comprise one or more tags, and wherein the one or more tags show one or more of:

one or more indications for administration of the pharmaceutical composition, storage information, dosing information, and/or instructions about how to administer the pharmaceutical composition.

\* \* \* \* \*